(12) United States Patent
Goebel et al.

(10) Patent No.: US 8,999,460 B2
(45) Date of Patent: Apr. 7, 2015

(54) COMPOUNDS AND LIQUID-CRYSTALLINE MEDIUM

(75) Inventors: Mark Goebel, Darmstadt (DE); Rocco Fortte, Frankfurt am Main (DE); Detlef Pauluth, Ober-Ramstadt (DE)

(73) Assignee: MERCK PATENT GmbH, Darmstadt (DE)

(*) Notice: Subject to any disclaimer, the term of this patent is extended or adjusted under 35 U.S.C. 154(b) by 38 days.

(21) Appl. No.: 13/451,749

(22) Filed: Apr. 20, 2012

(65) Prior Publication Data

US 2012/0268706 A1 Oct. 25, 2012

(30) Foreign Application Priority Data

Apr. 21, 2011 (DE) .......................... 10 2011 018 629
Jun. 1, 2011 (DE) .......................... 10 2011 103 024

(51) Int. Cl.
 *C09K 19/54* (2006.01)
 *C09K 19/30* (2006.01)
 *C09K 19/12* (2006.01)
 *C09K 19/34* (2006.01)
 *C09K 19/44* (2006.01)

(52) U.S. Cl.
 CPC ............ *C09K 19/54* (2013.01); *C09K 19/3483* (2013.01); *C09K 19/44* (2013.01); *C09K 19/3098* (2013.01); *C09K 2019/123* (2013.01); *C09K 2019/3004* (2013.01); *C09K 2019/301* (2013.01); *C09K 2019/3016* (2013.01); *C09K 2019/3027* (2013.01)
 USPC .................... 428/1.1; 252/299.01; 252/299.5; 252/299.63; 252/299.66

(58) Field of Classification Search
 USPC ............... 252/299.01, 299.5, 299.63, 299.66; 428/1.1; 546/188, 194, 221, 242
 See application file for complete search history.

(56) References Cited

U.S. PATENT DOCUMENTS

| 6,958,176 | B2 | 10/2005 | Li et al. | |
|---|---|---|---|---|
| 8,084,522 | B2 * | 12/2011 | Rinker | ............................ 524/99 |
| 2004/0085490 | A1 | 5/2004 | Li et al. | |
| 2006/0011886 | A1 | 1/2006 | Li et al. | |
| 2009/0253745 | A1 | 10/2009 | Mata et al. | |
| 2010/0304284 | A1 * | 12/2010 | Rinker | ............................... 430/7 |
| 2011/0101270 | A1 * | 5/2011 | Manabe et al. | .......... 252/299.62 |
| 2013/0131052 | A1 | 5/2013 | Matier et al. | |

FOREIGN PATENT DOCUMENTS

| CN | 1653125 A | 5/2013 |
|---|---|---|
| EP | 1 184 442 A1 | 3/2002 |
| JP | 2002234996 A | 8/2002 |
| JP | 04920974 B2 | 2/2012 |
| WO | 2008105552 A1 | 9/2008 |
| WO | 2009115186 | 9/2009 |
| WO | 2009070693 A2 | 10/2009 |
| WO | 2009129911 | 10/2009 |

OTHER PUBLICATIONS

Y. Ohkatsu, "Search for Unified Action Mechanism of Hindered Amine Light Stabilizers," Journal of the Japan Petroleum Institute, vol. 51, No. 4 (2008) pp. 191-204.
P. Mieville et al., "Scavenging Free Radicals to Preserve Enhancement and Extend Relaxation Times in NMR Using Dynamic Nuclear Polarization", Angew. Chem., vol. 122 (2010) pp. 6318-6321.
M. Inoue et al., "Recent Measurement of Liquid Crystal Material Characteristics", LCT7-1 Invited, IDW '06 pp. 647-650.
English translation of Chinese Office Action, dated Jan. 16, 201, issued in corresponding Chiniese application No. CN 201210114137.0.
"Reaction sequence in hydrogenation of unsaturated nitroxyl radicals on group VIII metals", Bulletin of Acad. of Sci. of USSR, vol. 24, Issue 6, Jun. 1975, pp. 1248-1253.
Litvin, E.F. et al., "Sequence of reactions during hydrogenation of unsaturated nitroxyl radicals on Group VIII metals", 1975:496041 CAPLUS (1975).

* cited by examiner

*Primary Examiner* — Shean C Wu
(74) *Attorney, Agent, or Firm* — Millen, White, Zelano & Branigan, P.C.

(57) ABSTRACT

The invention relates to compounds of the formula I, and to a liquid-crystalline medium, preferably having a nematic phase and negative dielectric anisotropy, which comprises one or more compounds of formula I, defined herein, for use in an electro-optical display, particularly in an active-matrix display based on the VA, ECB, PALO, FFS or IPS effect, and to the use of the compounds of the formula I for the stabilization of a liquid-crystalline medium which comprises one or more compounds of the formula II and one or more compounds of the formulae III-1 to III-4, defined herein.

24 Claims, No Drawings

COMPOUNDS AND LIQUID-CRYSTALLINE MEDIUM

The present invention relates to novel compounds, in particular for use in liquid-crystal media, but also to the use of these liquid-crystal media in liquid-crystal displays, and to these liquid-crystal displays, particularly liquid-crystal displays which use the ECB (electrically controlled birefringence) effect with dielectrically negative liquid crystals in a homeotropic initial alignment. The liquid-crystal media according to the invention are distinguished by a particularly short response time in the displays according to the invention at the same time as a high voltage holding ratio (VHR or also just HR for short).

The principle of electrically controlled birefringence, the ECB effect or DAP (deformation of aligned phases) effect, was described for the first time in 1971 (M. F. Schieckel and K. Fahrenschon, "Deformation of nematic liquid crystals with vertical orientation in electrical fields", Appl. Phys. Lett. 19 (1971), 3912). Papers by J. F. Kahn (Appl. Phys. Lett. 20 (1972), 1193) and G. Labrunie and J. Robert (J. Appl. Phys. 44 (1973), 4869) followed.

The papers by J. Robert and F. Clerc (SID 80 Digest Techn. Papers (1980), 30), J. Duchene (Displays 7 (1986), 3) and H. Schad (SID 82 Digest Techn. Papers (1982), 244) have shown that liquid-crystalline phases must have high values for the ratio between the elastic constants $K_3/K_1$, high values for the optical anisotropy $\Delta n$ and values for the dielectric anisotropy $\Delta\varepsilon$ of $\leq -0.5$ in order to be suitable for use for high-information display elements based on the ECB effect. Electro-optical display elements based on the ECB effect have a homeotropic edge alignment (VA technology=vertically aligned). Dielectrically negative liquid-crystal media can also be used in displays which use the so-called IPS (in-plane switching) effect.

Industrial application of this effect in electro-optical display elements requires LC phases which have to meet a multiplicity of requirements. Particularly important here are chemical resistance to moisture, air and physical influences, such as heat, radiation in the infrared, visible and ultraviolet regions, and direct and alternating electric fields.

Furthermore, LC phases which can be used industrially are required to have a liquid-crystalline mesophase in a suitable temperature range and low viscosity.

None of the series of compounds having a liquid-crystalline mesophase that have been disclosed hitherto includes a single compound which meets all these requirements. Mixtures of two to 25, preferably three to 18, compounds are therefore generally prepared in order to obtain substances which can be used as LC phases.

Matrix liquid-crystal displays (MLC displays) are known. Non-linear elements which can be used for individual switching of the individual pixels are, for example, active elements (i.e. transistors). The term "active matrix" is then used, where in general use is made of thin-film transistors (TFTs), which are generally arranged on a glass plate as substrate.

A distinction is made between two technologies: TFTs comprising compound semiconductors, such as, for example, CdSe, or TFTs based on polycrystalline and, inter alia, amorphous silicon. The latter technology currently has the greatest commercial importance worldwide.

The TFT matrix is applied to the inside of one glass plate of the display, while the other glass plate carries the transparent counterelectrode on its inside. Compared with the size of the pixel electrode, the TFT is very small and has virtually no adverse effect on the image. This technology can also be extended to fully color-capable displays, in which a mosaic of red, green and blue filters is arranged in such a way that a filter element is located opposite each switchable pixel.

The TFT displays most used hitherto usually operate with crossed polarizers in transmission and are backlit. For TV applications, IPS cells or ECB (or VAN) cells are used, whereas monitors usually use IPS cells or TN (twisted nematic) cells, and notebooks, laptops and mobile applications usually use TN cells.

The term MLC displays here encompasses any matrix display having integrated non-linear elements, i.e., besides the active matrix, also displays with passive elements, such as varistors or diodes (MIM=metal-insulator-metal).

MLC displays of this type are particularly suitable for TV applications, monitors and notebooks or for displays with a high information density, for example in automobile manufacture or aircraft construction. Besides problems regarding the angle dependence of the contrast and the response times, difficulties also arise in MLC displays due to insufficiently high specific resistance of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210-288 Matrix LCD Controlled by Double Stage Diode Rings, pp. 141 ff., Paris; STROMER, M., Proc. Eurodisplay 84, September 1984: Design of Thin Film Transistors for Matrix Addressing of Television Liquid Crystal Displays, pp. 145 ff., Paris]. With decreasing resistance, the contrast of an MLC display deteriorates. Since the specific resistance of the liquid-crystal mixture generally drops over the life of an MLC display owing to interaction with the inside surfaces of the display, a high (initial) resistance is very important for displays that have to have acceptable resistance values over a long operating period.

Displays which use the ECB effect have become established as so-called VAN (vertically aligned nematic) displays, besides IPS displays (for example: Yeo, S. D., Paper 15.3: "An LC Display for the TV Application", SID 2004 International Symposium, Digest of Technical Papers, XXXV, Book II, pp. 758 and 759) and the long-known TN displays, as one of the three more recent types of liquid-crystal display that are currently the most important, in particular for television applications.

The most important designs that should be mentioned are: MVA (multidomain vertical alignment, for example: Yoshide, H. et al., Paper 3.1: "MVA LCD for Notebook or Mobile PCs . . . ", SID 2004 International Symposium, Digest of Technical Papers, XXXV, Book I, pp. 6 to 9, and Liu, C. T. et al., Paper 15.1: "A 46-inch TFT-LCD HDTV Technology . . . ", SID 2004 International Symposium, Digest of Technical Papers, XXXV, Book II, pp. 750 to 753), PVA (patterned vertical alignment, for example: Kim, Sang Soo, Paper 15.4: "Super PVA Sets New State-of-the-Art for LCD-TV", SID 2004 International Symposium, Digest of Technical Papers, XXXV, Book II, pp. 760 to 763) and ASV (advanced super view, for example: Shigeta, Mitzuhiro and Fukuoka, Hirofumi, Paper 15.2: "Development of High Quality LCDTV", SID 2004 International Symposium, Digest of Technical Papers, XXXV, Book II, pp. 754 to 757).

In general form, the technologies are compared, for example, in Souk, Jun, SID Seminar 2004, Seminar M-6: "Recent Advances in LCD Technology", Seminar Lecture Notes, M-6/1 to M-6/26, and Miller, Ian, SID Seminar 2004, Seminar M-7: "LCD-Television", Seminar Lecture Notes, M-7/1 to M-7/32. Although the response times of modern ECB displays have already been significantly improved by addressing methods with overdrive, for example: Kim, Hyeon Kyeong et al., Paper 9.1: "A 57-in. Wide UXGA TFT-LCD for HDTV Application", SID 2004 International Symposium, Digest of Technical Papers, XXXV, Book I, pp. 106 to 109, the achievement of video-compatible response times, in particular in the switching of grey shades, is still a problem which has not yet been solved to a satisfactory extent.

ECB displays, like ASV displays, use liquid-crystalline media having negative dielectric anisotropy (Δ∈), whereas TN and to date all conventional IPS displays use liquid-crystalline media having positive dielectric anisotropy.

In liquid-crystal displays of this type, the liquid crystals are used as dielectrics, whose optical properties change reversibly on application of an electrical voltage.

Since in displays in general, i.e. also in displays in accordance with these mentioned effects, the operating voltage should be as low as possible, use is made of liquid-crystal media which are generally predominantly composed of liquid-crystal compounds, all of which have the same sign of the dielectric anisotropy and have the highest possible value of the dielectric anisotropy. In general, at most relatively small proportions of neutral compounds and if possible no compounds having a sign of the dielectric anisotropy which is opposite to that of the medium are employed. In the case of liquid-crystal media having negative dielectric anisotropy for ECB displays, predominantly compounds having negative dielectric anisotropy are thus employed. The liquid-crystal media employed generally consist predominantly and usually even essentially of liquid-crystal compounds having negative dielectric anisotropy.

In the media used in accordance with the present application, at most significant amounts of dielectrically neutral liquid-crystal compounds and generally only very small amounts of dielectrically positive compounds or even none at all are typically employed, since in general the liquid-crystal displays are intended to have the lowest possible addressing voltages.

For many practical applications in liquid-crystal displays, the known liquid-crystal media are not sufficiently stable. In particular, their stability to irradiation with UV, but also even with conventional backlighting, results in an impairment, in particular, of the electrical properties. Thus, for example, the conductivity increases significantly.

The use of so-called "hindered amine light stabilizers", HALS for short, has already been proposed for the stabilization of liquid-crystal mixtures.

Nematic liquid-crystal mixtures having negative dielectric anisotropy which comprise a small amount of TINUVIN®770, a compound of the formula

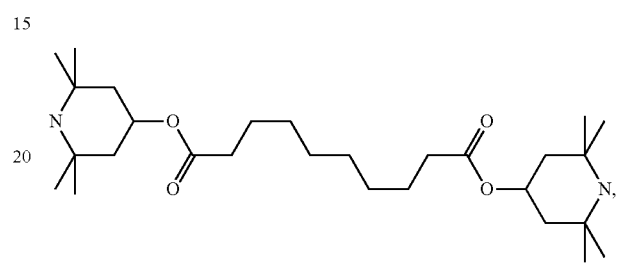

as stabilizers, are proposed, for example, in WO 2009/129911 A1. However, the corresponding liquid-crystal mixtures do not have adequate properties for some practical applications. Inter alia, they are not sufficiently stable to irradiation using typical CCFL (Cold Cathode Fluorescent Lamp) backlighting.

Similar liquid-crystal mixtures are also known, for example, from EP 2 182 046 A1, WO 2008/009417 A1, WO 2009/021671 A1 and WO 2009/115186 A1. However, the use of stabilizers is not indicated therein.

According to the disclosure therein, these liquid-crystal mixtures may optionally also comprise stabilizers of various types, such as, for example, phenols and sterically hindered amines (hindered amine light stabilizers, HALS for short). However, these liquid-crystal mixtures are characterized by relatively high threshold voltages and by at best moderate stabilities. In particular, their voltage holding ratio drops after exposure. In addition, a yellowish discoloration often arises.

The use of various stabilizers in liquid-crystalline media is described, for example, in JP (S)55-023169 (A), JP(H)05-117324 (A), WO 02/18515 A1 and JP(H) 09-291282 (A).

TINUVIN®123, a compound of the formula

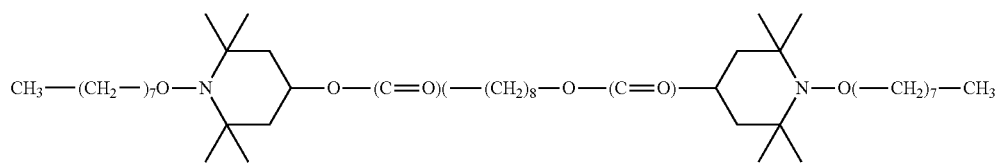

has also been proposed for stabilization purposes.

Mesogenic compounds containing one or two HALS units are disclosed in EP 1 784 442 A1.

HALS with various substituents on the nitrogen atom are compared with respect to their $pK_B$ values in Ohkatsu, Y., *J. of Japan Petroleum Institute*, 51, 2008, pages 191-204. The following types of structural formulae are disclosed here.

| Type | Active group of the stabilizer |
|---|---|
| "HALS" | RO—⬡—N—H |
| "R-HALS" or "NR-HALS" | RO—⬡—N—R |
| "NOR-HALS" | RO—⬡—N—OR |

The compound TEMPOL, of the following formula:

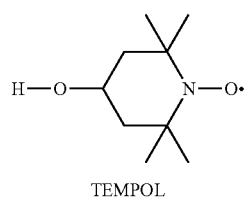

TEMPOL is known; it is mentioned, for example, in Miéville, P. et al., Angew. Chem. 2010, 122, pages 6318-6321. It is commercially available from various manufacturers and is employed, for example, as polymerization inhibitor and, in particular in combination with UV absorbers, as light or UV protection in formulations for precursors of polyolefins, polystyrenes, polyamides, coatings and PVC.

The liquid-crystal media of the prior art having correspondingly low addressing voltages have relatively low electrical resistance values or a low VHR and often result in undesired flicker and/or inadequate transmission in the displays. In addition, they are not sufficiently stable to heating and/or UV exposure, at least if they have correspondingly high polarity, as is necessary for low addressing voltages.

On the other hand, the addressing voltage of the displays of the prior art which have a high VHR is often too high, in particular for displays which are not connected directly or not continuously to the power supply network, such as, for example, displays for mobile applications.

In addition, the phase range of the liquid-crystal mixture must be sufficiently broad for the intended application of the display.

The response times of the liquid-crystal media in the displays must be improved, i.e. reduced. This is particularly important for displays for television or multimedia applications. In order to improve the response times, it has repeatedly been proposed in the past to optimize the rotational viscosity of the liquid-crystal media ($\gamma_1$), i.e. to achieve media having the lowest possible rotational viscosity. However, the results achieved here are inadequate for many applications and therefore make it appear desirable to find further optimization approaches.

Adequate stability of the media to extreme loads, in particular to UV exposure and heating, is very particularly important. In particular in the case of applications in displays in mobile equipment, such as, for example, mobile telephones, this may be crucial.

The disadvantage of the MLC displays disclosed hitherto is due to their comparatively low contrast, the relatively high viewing-angle dependence and the difficulty in producing grey shades in these displays, as well as their inadequate VHR and their inadequate lifetime.

There thus continues to be a great demand for MLC displays having very high specific resistance at the same time as a large working-temperature range, short response times and a low threshold voltage, with the aid of which various grey shades can be produced and which have, in particular, a good and stable VHR.

The invention has an object of providing MLC displays, not only for monitor and TV applications, but also for mobile telephones and navigation systems, which are based on the ECB or IPS effect, do not have the disadvantages indicated above, or only do so to a lesser extent, and at the same time have very high specific resistance values. In particular, it must be ensured for mobile telephones and navigation systems that they also work at extremely high and extremely low temperatures.

Upon further study of the specification and appended claims, other objects and advantages of the invention will become apparent.

Surprisingly, it has been found that it is possible to achieve liquid-crystal displays which have, in particular in ECB displays, a low threshold voltage with short response times and at the same time a sufficiently broad nematic phase, favorable, relatively low birefringence ($\Delta n$), good stability to decomposition by heating and by UV exposure, and a stable, high VHR if use is made in these display elements of nematic liquid-crystal mixtures which comprise at least one compound of the formula I and in each case at least one compound of the formula II, preferably of the sub-formula II-1, and optionally at least one compound selected from the group of the compounds of the formulae III-1 to III-4, preferably of the formula III-2.

Media of this type can be used, in particular, for electro-optical displays having active-matrix addressing based on the ECB effect and for IPS (in-plane switching) displays.

The invention thus relates to a liquid-crystalline medium based on a mixture of polar compounds which comprises at least one compound of the formula I and one or more compounds of the formula II and preferably in addition one or more compounds selected from the group of the compounds of the formulae III-1 to III-4.

The mixtures according to the invention exhibit very broad nematic phase ranges with clearing points $\geq 70°$ C., very favorable values for the capacitive threshold, relatively high values for the holding ratio and at the same time good low-temperature stabilities at $-20°$ C. and $-30°$ C., as well as very low rotational viscosities. The mixtures according to the invention are furthermore distinguished by a good ratio of clearing point and rotational viscosity and by a high negative dielectric anisotropy.

Surprisingly, it has now been found that it is possible to achieve liquid-crystalline media having a suitably high Δε, a suitable phase range and Δn which do not have the disadvantages of the prior-art materials, or at least only do so to a considerably reduced extent.

Surprisingly, it has been found here that the compounds of the formula I, even when used alone without additional heat stabilizers, result in considerable, in many cases adequate, stabilization of liquid-crystal mixtures both to UV exposure and also to heating. This is the case, in particular, in most cases in which the parameter $R^{11}$ in the compounds of the formula I used denotes O•. The compounds of the formula I in which $R^{11}$ denotes O• are therefore particularly preferred, and the use of precisely these compounds in the liquid-crystal mixtures is particularly preferred.

However, adequate stabilization of liquid-crystal mixtures both against UV exposure and against heating can also be achieved, in particular, if one or more further compounds, preferably phenolic stabilizers, are present in the liquid-crystal mixture in addition to the compound of the formula I, or the compounds of the formula I. These further compounds are suitable as heat stabilizers.

The invention thus relates to compounds of the formula I, and to a liquid-crystalline medium having a nematic phase and negative dielectric anisotropy which comprises
a) one or more compounds of the formula I, preferably in a concentration in the range from 1 ppm to 1000 ppm, preferably in the range from 1 ppm to 500 ppm, particularly preferably in the range from 1 ppm to 250 ppm,

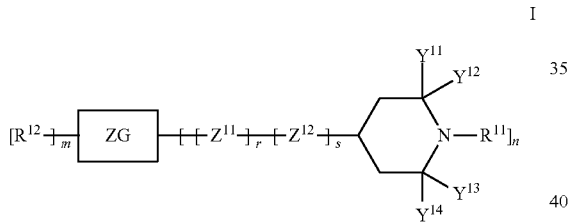

I in which
n denotes an integer from 1 to 4, preferably 1, 2 or 3, particularly preferably 1 or 2, and very particularly preferably 2,
m denotes (4-n),

denotes an organic radical having 4 bonding sites, preferably an alkanetetrayl unit having 1 to 20 C atoms, in which, in addition to the m groups $R^{12}$ present in the molecule, but independently thereof, a further H atom may be replaced by $R^{12}$ or a plurality of further H atoms may each be replaced by $R^{12}$, preferably a straight-chain alkanetetrayl unit having one valence on each of the two terminal C atoms, in which one —$CH_2$— group or a plurality of —$CH_2$— groups may each be replaced by —O— or —(C=O)— in such a way that two O atoms are not bonded directly to one another, or denotes a substituted or unsubstituted aromatic or heteroaromatic hydrocarbon radical having 1 to 4 valences, in which, in addition to the m groups $R^{12}$ present in the molecule, but independently thereof, a further H atom may be replaced by $R^{12}$ or a plurality of further H atoms may each be replaced by $R^{12}$, $Z^{11}$ and $Z^{12}$, independently of one another, denote —O—, —(C=O)—, —(N—$R^{14}$)— or a single bond, but do not both simultaneously denote —O—, r and s, independently of one another, denote 0 or 1, $Y^{11}$ to $Y^{14}$ each, independently of one another, denote alkyl having 1 to 4 C atoms, preferably methyl or ethyl, particularly preferably all denote either methyl or ethyl and very particularly preferably methyl, or alternatively, independently from each other, the two pairs ($Y^{11}$ and $Y^{12}$) and ($Y^{13}$ and $Y^{14}$) may be connected by a bond to preferably 5 C-atoms, most preferably they are 1,5-pentylene, $R^{11}$ denotes O—$R^{13}$, O• or OH, preferably O—$R^{13}$ or O•, particularly preferably O•, isopropoxy, cyclohexyloxy, acetophenoxy or benzoxy and very particularly preferably O•, $R^{12}$ on each occurrence, independently of one another, denotes H, F, $OR^{14}$, $NR^{14}R^{15}$, a straight-chain or branched alkyl chain having 1-20 C atoms, in which one —$CH_2$— group or a plurality of —$CH_2$— groups may each be replaced by —O— or —C(=O)—, but two adjacent —$CH_2$— groups cannot be replaced by —O—, or denotes a hydrocarbon radical which contains a cycloalkyl or alkylcycloalkyl unit, and in which one —$CH_2$— group or a plurality of —$CH_2$— groups may each be replaced by —O— or —C(=O)—, but two adjacent —$CH_2$— groups cannot be replaced by —O—, and in which one H atom or a plurality of H atoms may each be replaced by $OR^{14}$, $N(R^{14})(R^{15})$ or $R^{16}$, or denotes an aromatic or heteroaromatic hydrocarbon radical, in which one H atom or a plurality of H atoms may each be replaced by $OR^{14}$, $N(R^{14})(R^{15})$ or $R^{16}$, $R^{13}$ on each occurrence, independently of one another, denotes a straight-chain or branched alkyl chain having 1-20 C atoms, in which one —$CH_2$— group or a plurality of —$CH_2$— groups may each be replaced by —O— or —C(=O)—, but two adjacent —$CH_2$— groups cannot be replaced by —O—, or denotes a hydrocarbon radical which contains a cycloalkyl or alkylcycloalkyl unit, and in which one —$CH_2$— group or a plurality of —$CH_2$— groups may each be replaced by —O— or —C(=O)—, but two adjacent —$CH_2$— groups cannot be replaced by —O—, and in which one H atom or a plurality of H atoms may each be replaced by $OR^{14}$, $N(R^{14})(R^{15})$ or $R^{16}$, or denotes an aromatic or heteroaromatic hydrocarbon radical, in which one H atom or a plurality of H atoms may each be replaced by $OR^{14}$, $N(R^{14})(R^{15})$ or $R^{16}$, or can be

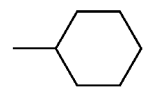

(cyclohexyl), in which one or more —$CH_2$— groups may be replaced by —O—, —CO— or —$NR^{14}$—, or an acetophenyl, isopropyl or 3-heptyl radical, $R^{14}$ on each occurrence, independently of one another, denotes a straight-chain or branched alkyl or acyl group having 1 to 10 C atoms, preferably n-alkyl, or an aromatic hydrocarbon or carboxyl radical having 6-12 C atoms, preferably with the proviso that, in the case of $R^{14}$ is being part of $N(R^{14})(R^{15})$, at least one acyl radical is present, $R^{15}$ on each occurrence, independently of one another, denotes a straight-chain or branched alkyl or acyl group having 1 to 10 C atoms, preferably n-alkyl, or an aromatic hydrocarbon or carboxyl radical having 6-12 C atoms, preferably with the proviso that, in the case of $R^{15}$ is being part of $N(R^{14})(R^{15})$, at least one acyl radical is present, $R^{16}$ on each occurrence, independently of one another, denotes a straight-chain or branched alkyl group having 1 to 10 C atoms, in which one —$CH_2$— group or a plurality of —$CH_2$— groups may each be replaced by —O— or —C(=O)—, but two adjacent —$CH_2$— groups cannot be replaced by —O—, with the provisos that, (i) in the case where n=1, $R^{11}$=O•, and
—$[Z^{11}$—$]_r$—$[Z^{12}]_s$—=—O—, —(CO)—O—, —O—(CO)—, —O—(CO)—O—, —$NR^{14}$— or —$NR^{14}$—(CO)—, then

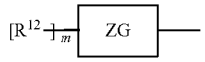

does not denote straight-chain or branched alkyl having 1 to 10 C atoms, also cycloalkyl, cycloalkylalkyl or alkylcycloalkyl, where one or more —$CH_2$— groups in all these groups may be replaced by —O— in such a way that two O atoms in the molecule are not bonded directly to one another, (ii) in the case where n=2 and $R^{11}$=O•, then

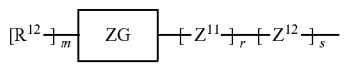

does not denote

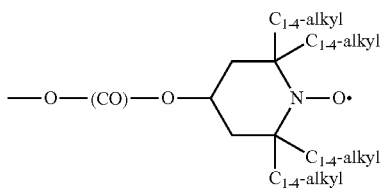

and (iii) in the case where n=2 and $R^{11}$=O—$R^{13}$, then $R^{13}$ does not denote n-$C_{1-9}$-alkyl, and b) one or more compounds of the formula II

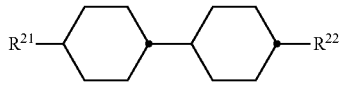

II in which $R^{21}$ denotes an unsubstituted alkyl radical having 1 to 7 C atoms or an unsubstituted alkenyl radical having 2 to 7 C atoms, preferably an n-alkyl radical, particularly preferably having 3, 4 or 5 C atoms, and $R^{22}$ denotes an unsubstituted alkenyl radical having 2 to 7 C atoms, preferably having 2, 3 or 4 C atoms, more preferably a vinyl radical or a 1-propenyl radical and in particular a vinyl radical, and optionally c) one or more compounds selected from the group of the formulae III-1 to III-4, preferably of the formula III-2,

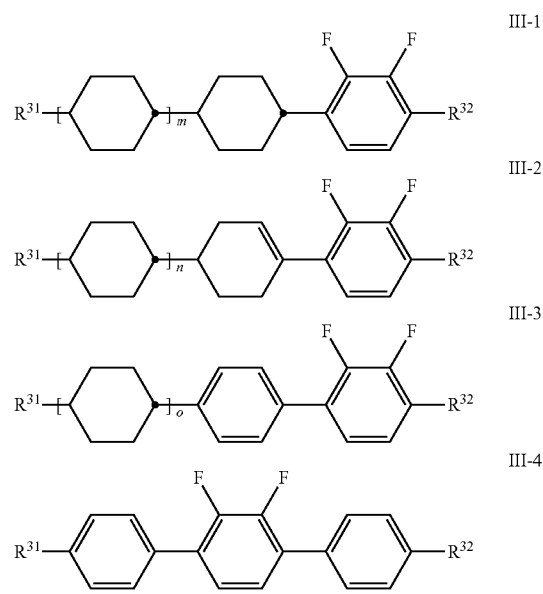

in which $R^{31}$ denotes an unsubstituted alkyl radical having 1 to 7 C atoms, preferably an n-alkyl radical, particularly preferably having 2 to 5 C atoms, $R^{32}$ denotes an unsubstituted alkyl radical having 1 to 7 C atoms, preferably having 2 to 5 C atoms, or an unsubstituted alkoxy radical having 1 to 6 C atoms, preferably having 2, 3 or 4 C atoms, and m, n and o each, independently of one another, denote 0 or 1.

Preferred are the following embodiments

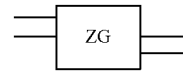

denotes

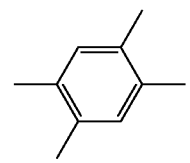

(benzene-1,2,4,5-tetrayl) or —$CH_2$—(CH—)—$[CH_2]_q$—(CH—)—$CH_2$— or >CH—$[CH_2]_p$—CH<, (where p∈{0, 1, 2, 3, 4, 5 to 18} and q∈{0, 1, 2, 3 to 16}) or

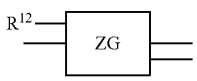

denotes
>CH—[CH$_2$]$_p$—CH$_2$— (where p∈{0, 1, 2, 3, 4, 5 to 18})
or

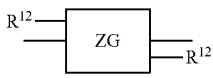

denotes
—CH$_2$—[CH$_2$]$_p$—CH$_2$— (where p∈{0, 1, 2, 3, 4, 5 to 18}), propane-1,2-diyl, butane-1,2-diyl, ethane-1,2-diyl,

(1,4-phenylene),

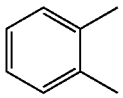

(1,2-phenylene) or

(1,4-cyclohexylene).

In the present application, the elements all include their respective isotopes. In particular, one or more H in the compounds may be replaced by D, and this is also particularly preferred in some embodiments. A correspondingly high degree of deuteration of the corresponding compounds enables, for example, detection and recognition of the compounds. This is very helpful in some cases, in particular in the case of the compounds of the formula I.

In the present application,
alkyl particularly preferably denotes straight-chain alkyl, in particular CH$_3$—, C$_2$H$_5$—, n-C$_3$H$_7$—, n-C$_4$H$_9$— or n-C$_5$H$_{11}$—, and
alkenyl particularly preferably denotes CH$_2$=CH—, E-CH$_3$—CH=CH—, CH$_2$=CH—CH$_2$—CH$_2$—, E-CH$_3$—CH=CH—CH$_2$—CH$_2$— or E-(n-C$_3$H$_7$)—CH=CH—.

In addition, in the present application,
(a) the substituted or unsubstituted aromatic hydrocarbon radicals for group ZG can be, for example, benzene-1,2,4,5-tetrayl, 1,4-phenylene, 1,2-phenylene, benzene-1,2,3,4-tetrayl, benzene-1,2,3,5-tetrayl, benzene-triyl, 1,3-phenylene, or phenyl, as well as larger aromatics like naphthyl or naphthylenes, and substituted aromatics such as methyl- or dimethyl-benzene-tertrayls; the substituted or unsubstituted heteroaromatic can be the corresponding pyridine- and pyrimidine-radicals;

(b) the hydrocarbon radical which contains a cycloalkyl or alkylcycloalkyl unit for group R$^{12}$ can be, for example, cyclopropyl, methylcyclopropyl, or dimethyl-cyclopropyl;

(c) the aromatic or heteroaromatic hydrocarbon radical for group R$^{12}$ can be, for example, phenyl, pyridyl, or pyrimidinyl;

(d) the hydrocarbon radical which contains a cycloalkyl or alkylcycloalkyl unit for group R$^{13}$ can be, for example, cyclopropyl, methylcyclopropyl, or dimethyl-cyclopropyl;

(e) the aromatic or heteroaromatic hydrocarbon radical for group R$^{13}$ can be, for example, phenyl, pyridyl, pyrimidinyl, naphthyl, or

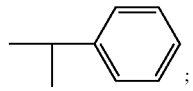;

and/or (f) the aromatic hydrocarbon or carboxyl radicals having 6-12 C atoms for groups R$^{14}$ and R$^{15}$ can be, for example, phenyl, naphthyl, —CO-phenyl, or —CO— naphthyl.

The liquid-crystalline media in accordance with the present application preferably comprise in total 1 ppm to 1000 ppm, preferably 1 ppm to 500 ppm, even more preferably 1 to 250 ppm and very particularly preferably 1 ppm to 100 ppm, of compounds of the formula I.

In further preferred embodiments, the concentration of the compounds of the formula I in the media according to the invention is preferably 90 ppm or less, particularly preferably 50 ppm or less, very particularly preferably 10 ppm or more to 80 ppm or less.

In a preferred embodiment of the present invention, in the compounds of the formula I,

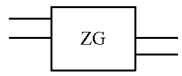

denotes

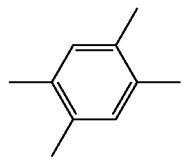

(benzene-1,2,4,5-tetrayl) or

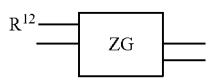

denotes

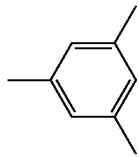

(benzene-1,3,5-triyl) or

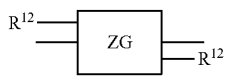

denotes

(1,4-phenylene),

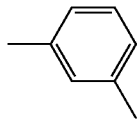

(1,3-phenylene),

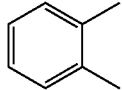

(1,2-phenylene) or

(1,4-cyclohexylene), and/or

—[$Z^{11}$—]$_r$—[$Z^{12}$—]$_s$ on each occurrence, independently of one another, denotes —O—, —(C=O)—O— or —O—(C=O)—, —(N—$R^{14}$)— or a single bond, preferably —O— or —(C=O)—O— or —O—(C=O)—, and/or $R^{11}$ denotes —O•, OH or O—$R^{13}$, preferably:
—O•, —O—CH(—$CH_3$)$_2$, —O—CH(—$CH_3$)(—$CH_2$)$_3$—$CH_3$, —O—CH(—$C_2H_5$)(—$CH_2$)$_3$—$CH_3$,

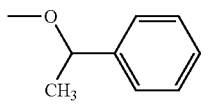

and/or $R^{12}$, if present, denotes alkyl or alkoxy, and/or $R^{13}$ denotes isopropyl or 3-heptyl, acetophenyl or cyclohexyl.

In a preferred embodiment of the present invention, the group

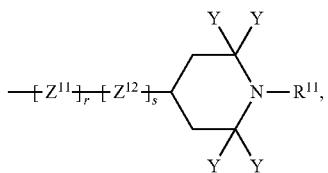

in the compounds of the formula I on each occurrence, independently of one another, denotes

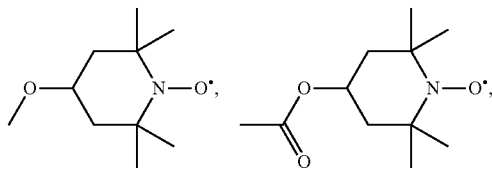

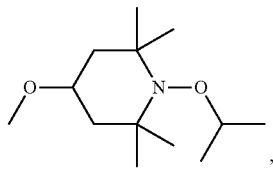

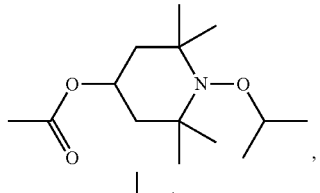

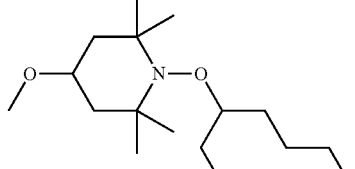

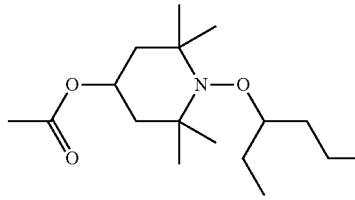

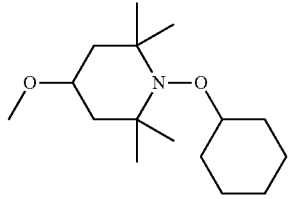

-continued

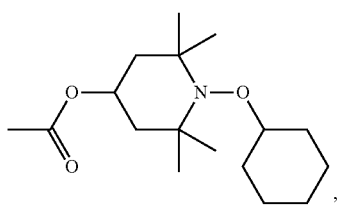

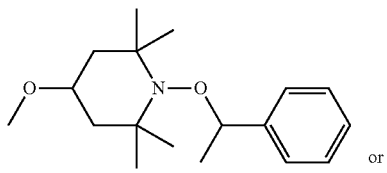

or

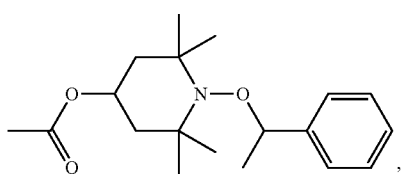

preferably

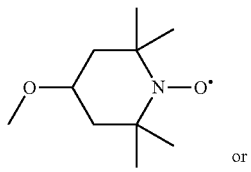 or 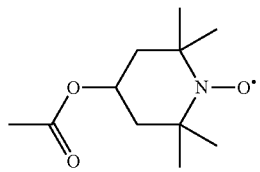

In a particularly preferred embodiment of the present invention, all groups

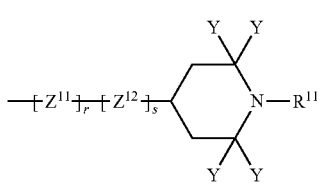

present in the compounds of the formula I have the same meaning.

These compounds are highly suitable as stabilizers in liquid-crystal mixtures. In particular, they stabilize the VHR of the mixtures against UV exposure.

In a preferred embodiment of the present invention, the media according to the invention in each case comprise one or more compounds of the formula I selected from the group of the compounds of the formulae I-1 to I-9, preferably selected from the group of the compounds of the formulae I-1 to I-4,

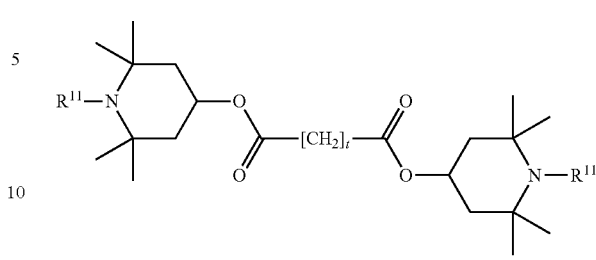

I-1

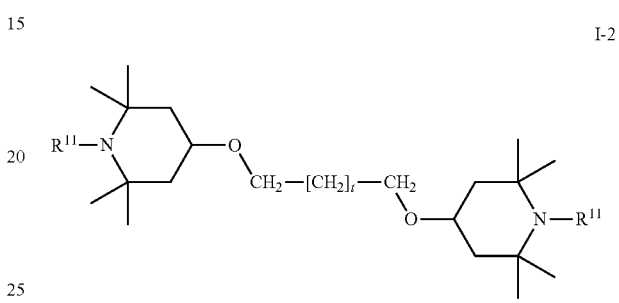

I-2

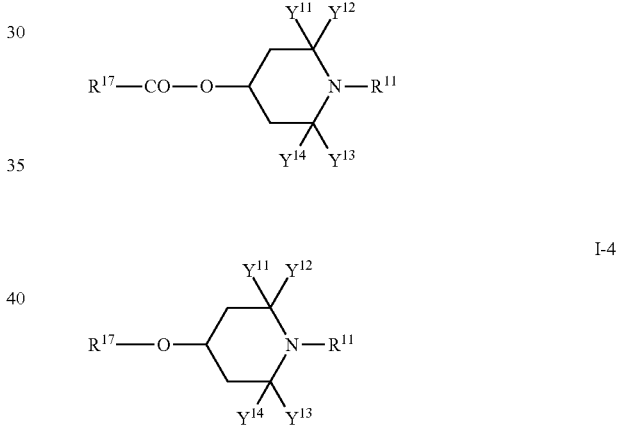

I-3

I-4

I-5

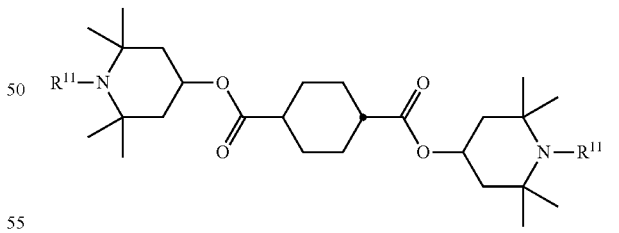

I-6

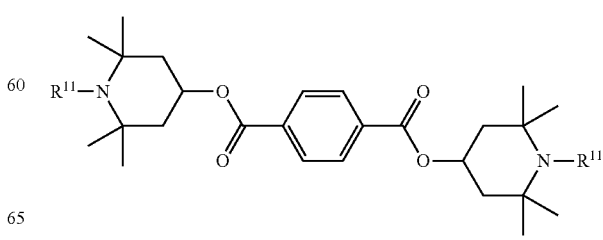

-continued

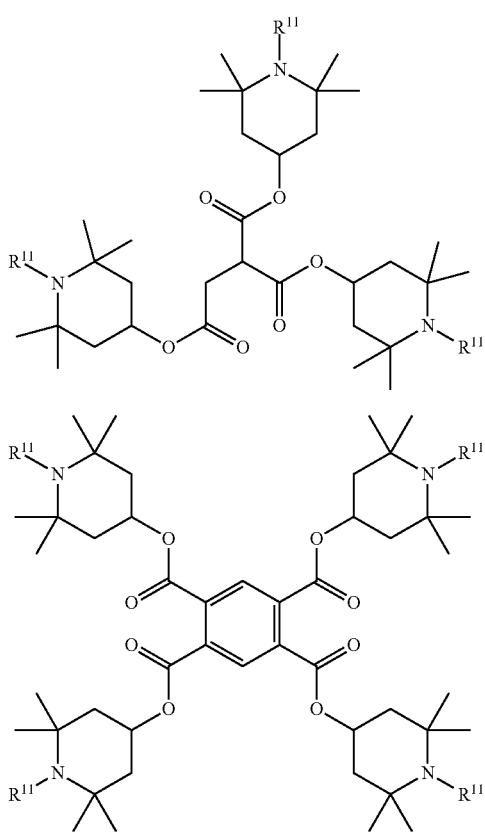

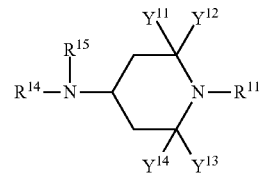

in which the parameters have the meanings indicated above under formula I, and t denotes an integer from 1 to 12, $R^{17}$ denotes a straight-chain or branched alkyl chain having 1-12 C atoms, in which one —$CH_2$— group or a plurality of —$CH_2$— groups may each be replaced by —O— or —C(=O)—, but two adjacent —$CH_2$— groups cannot be replaced by —O—, or denotes an aromatic or heteroaromatic hydrocarbon radical, in which one H atom or a plurality of H atoms may each be replaced by $OR^{14}$, $N(R^{14})(R^{15})$ or $R^{16}$.

In an even more preferred embodiment of the present invention, the media according to the invention in each case comprise one or more compounds of the formula I selected from the group of the following compounds, of the formulae I-1a-1 to I-8a-1:

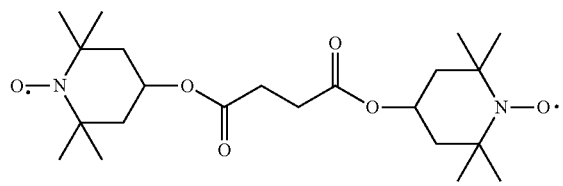

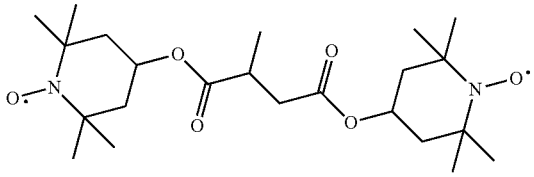

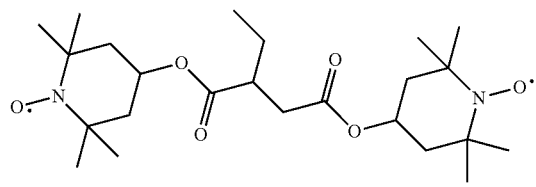

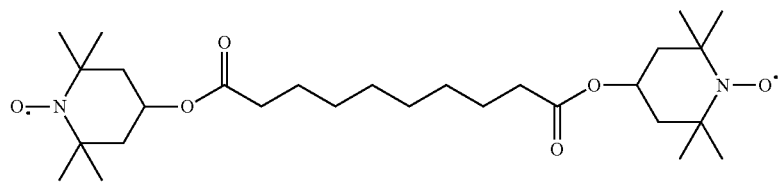

-continued
I-1a-5
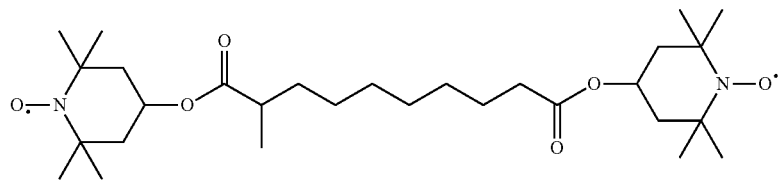
I-2a-1
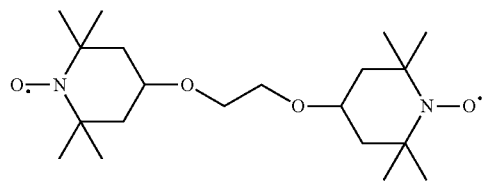
I-2a-2
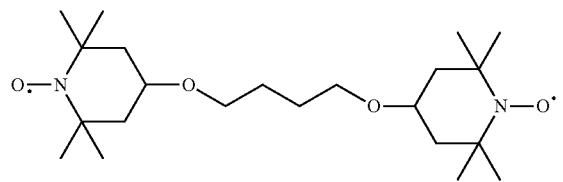
I-3a-1
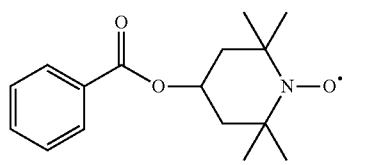
I-3a-2
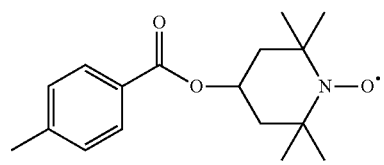
I-3a-3
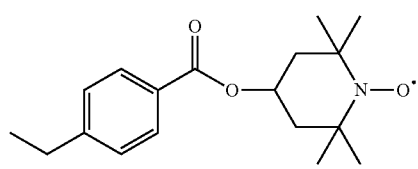
I-3a-4
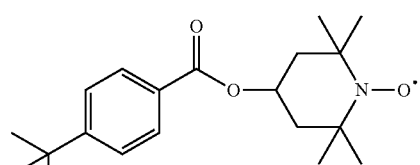
I-3a-5
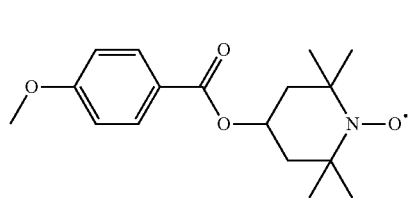
I-3a-6
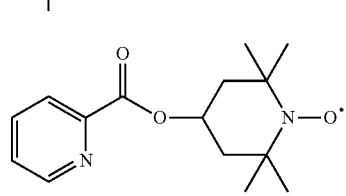
I-5a-1
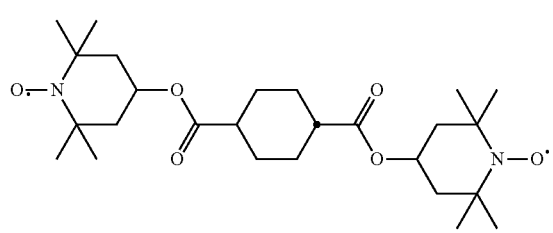
I-6a-1
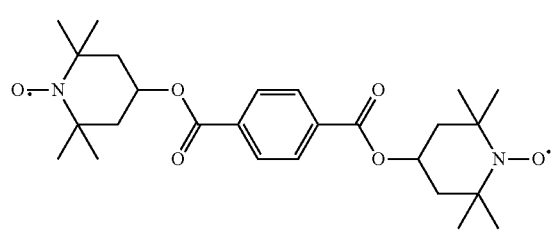
I-7a-1
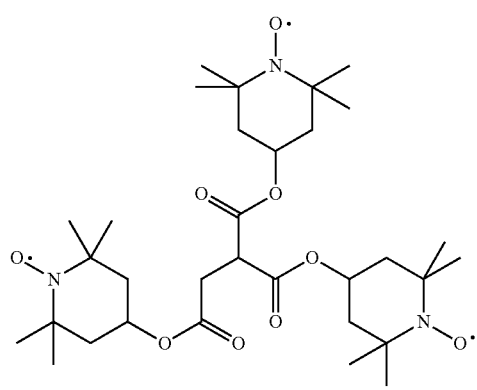
I-8a-1
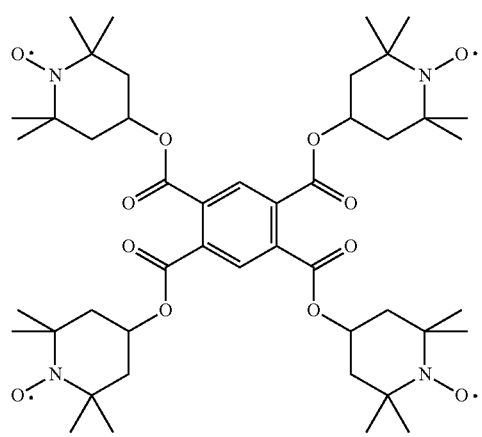

In an even more preferred embodiment of the present invention, the media according to the invention in each case comprise one or more compounds of the formula I selected from the group of the following compounds, of the formulae I-2a-1 and I-2a-2:

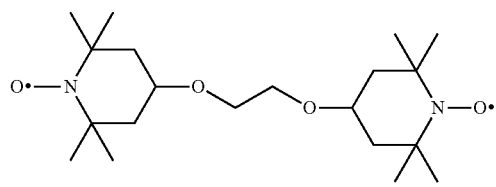

I-2a-1

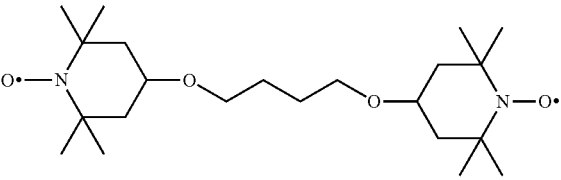

I-2a-2

In an alternative, preferred embodiment of the present invention, the media according to the invention in each case comprise one or more compounds of the formula I selected from the group of the following compounds, of the formulae I-1b-1 and I-1b-2,

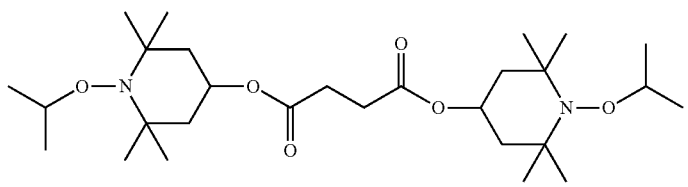

I-1b-1

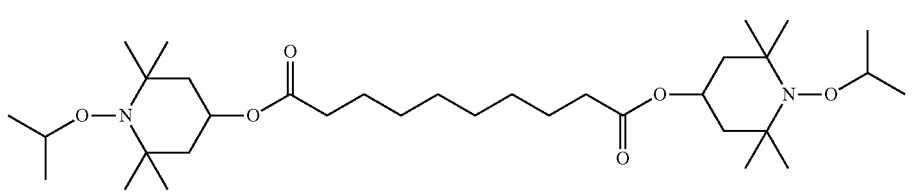

I-1b-2

In an alternative, preferred embodiment of the present invention, the media according to the invention in each case comprise one or more compounds of the formula I selected from the group of the following compounds, of the formulae I-1c-1 and I-1c-2,

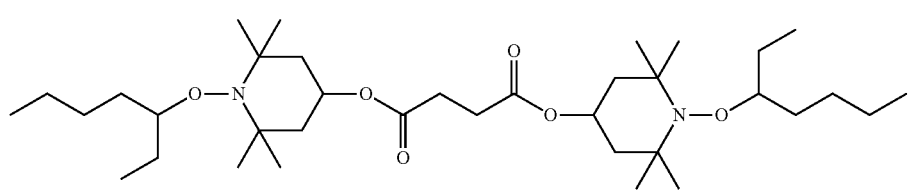

I-1c-1

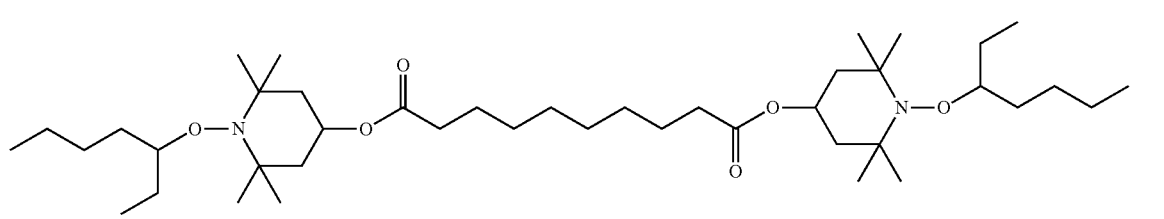

I-1c-2

In a further alternative, preferred embodiment of the present invention, the media according to the invention in each case comprise one or more compounds of the formula I selected from the group of the following compounds, of the formulae I-1d-1 to I-1d-4:

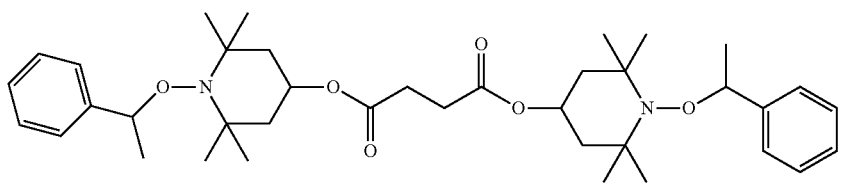
I-1d-1
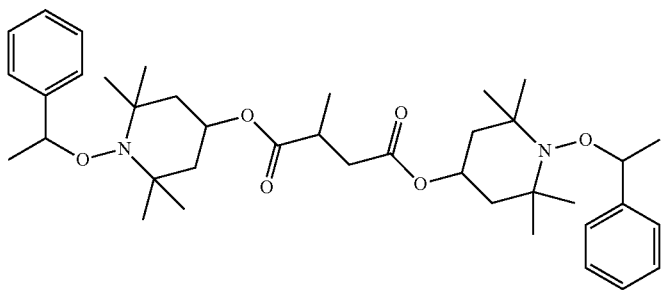
I-1d-2
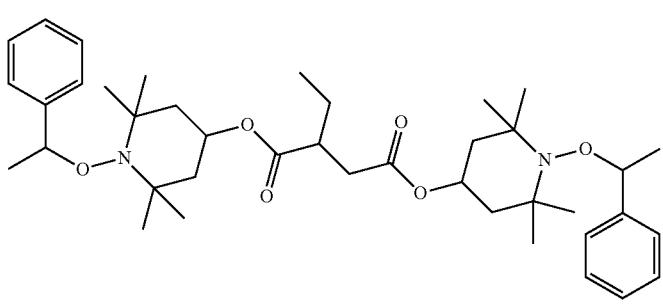
I-1d-3
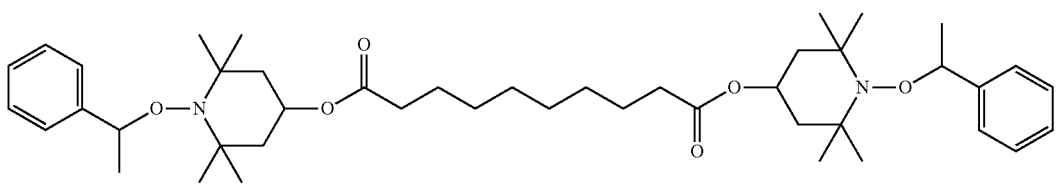
I-1d-4
In a further alternative, preferred embodiment of the present invention, the media according to the invention in each case comprise one or more compounds of the formula I selected from the group of the following compounds, of the formulae I-3d-1 to I-3d-8,
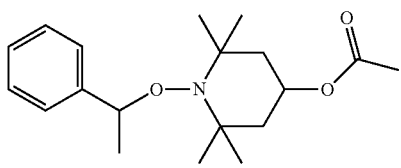
I-3d-1
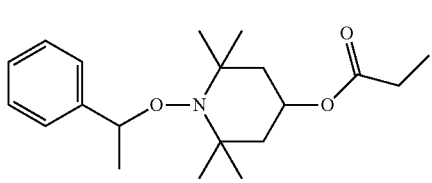
I-3d-2
-continued
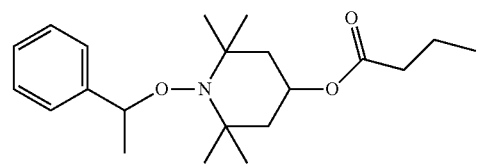
I-3d-3
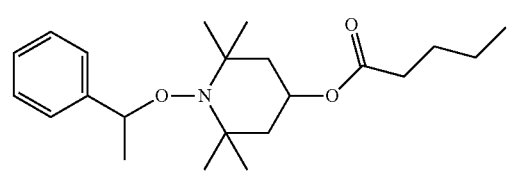
I-3d-4
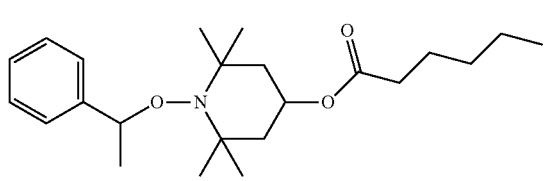
I-3d-5

-continued

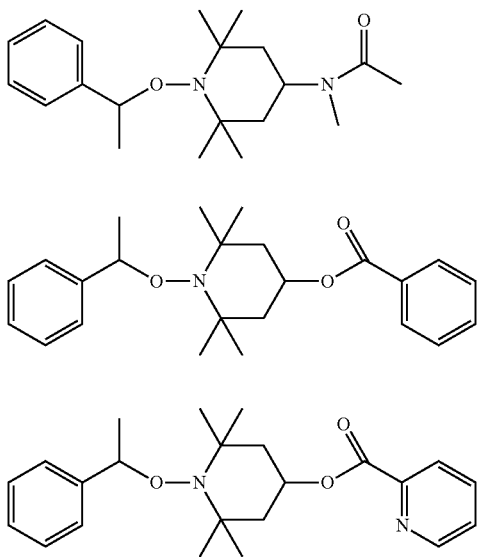

I-3d-6

I-3d-7

I-3d-8

In a further alternative, preferred embodiment of the present invention, the media according to the invention in each case comprise one or more compounds of the formula I selected from the group of the following compounds, of the formulae I-4-d-1 and I-4-d-2,

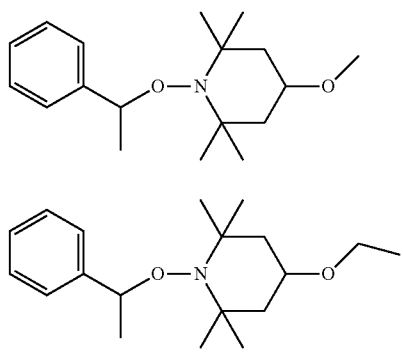

I-4d-1

I-4d-2

In a further alternative, preferred embodiment of the present invention, the media according to the invention in each case comprise one or more compounds of the formula I selected from the group of the following compounds, of the formulae I-1e-1 and I-1e-2,

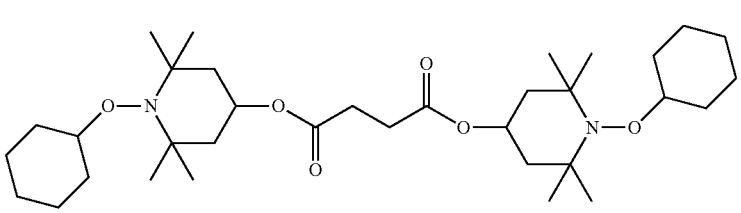

I-1e-1

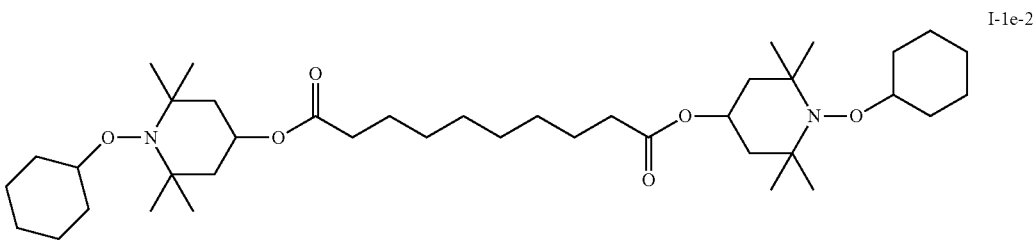

I-1e-2

In a further alternative, preferred embodiment of the present invention, the media according to the invention in each case comprise one or more compounds of the formula I selected from the group of the following compounds, of the formulae I-5e-1 to I-8e-1,

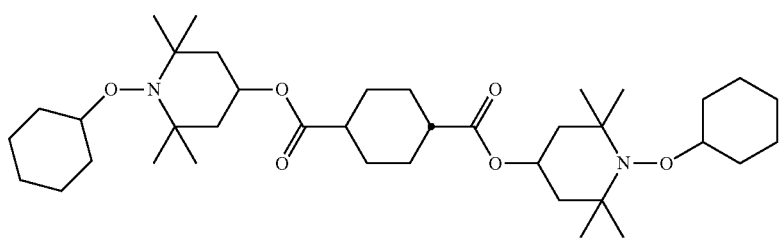

I-5e-1

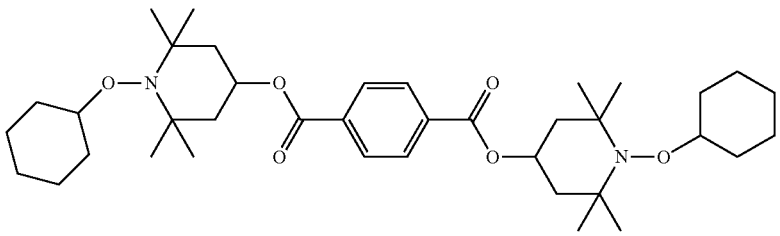

I-6e-1

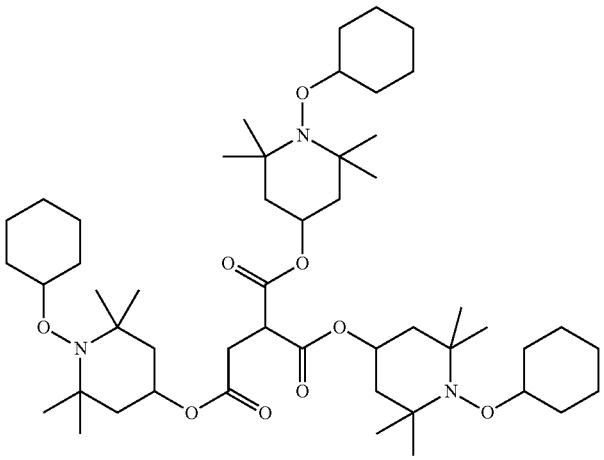

I-7e-1

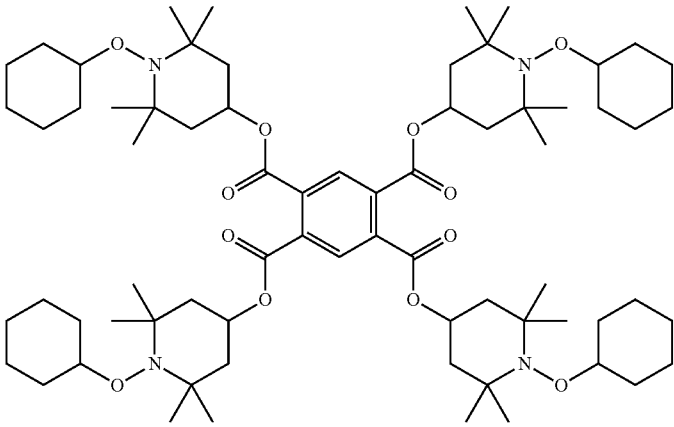

I-8e-1

In addition to the compounds of the formula I or preferred sub-formulae thereof, the media in accordance with the present invention preferably comprise one or more dielectrically neutral compounds of the formula II in a total concentration in the range from 5% or more to 90% or less, preferably from 10% or more to 80% or less, particularly preferably from 20% or more to 70% or less.

The medium according to the invention preferably comprises one or more compounds selected from the group of the formulae III-1 to III-4 in a total concentration in the range from 10% or more to 80% or less, preferably from 15% or more to 70% or less, particularly preferably from 20% or more to 60% or less.

The medium according to the invention particularly preferably comprises
one or more compounds of the formula III-1 in a total concentration in the range from 5% or more to 30% or less,
one or more compounds of the formula III-2 in a total concentration in the range from 3% or more to 30% or less,
one or more compounds of the formula III-3 in a total concentration in the range from 5% or more to 30% or less,
one or more compounds of the formula III-4 in a total concentration in the range from 1% or more to 30% or less.

Preferred compounds of the formula II are the compounds selected from the group of the compounds of the formulae II-1 and II-2, preferably selected from the compounds of the formula II-1,

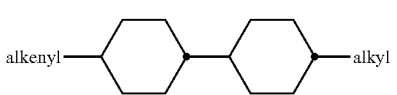

II-1

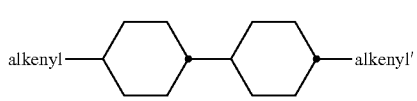

in which
alkyl denotes an alkyl radical having 1 to 7 C atoms, preferably having 2 to 5 C atoms,
alkenyl denotes an alkenyl radical having 2 to 5 C atoms, preferably having 2 to 4 C atoms, particularly preferably 2 C atoms,
alkenyl' denotes an alkenyl radical having 2 to 5 C atoms, preferably having 2 to 4 C atoms, particularly preferably having 2 to 3 C atoms.

The media according to the invention preferably comprise one or more compounds of the formula III-1, preferably one or more compounds selected from the group of the compounds of the formulae III-1-1 and III-1-2,

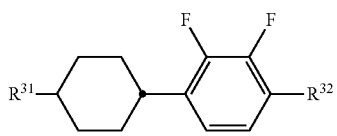

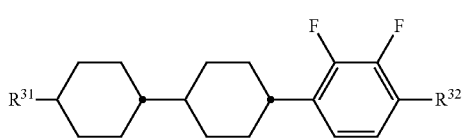

in which the parameters have the meanings given above for formula III-1, and preferably
$R^{31}$ denotes an alkyl radical having 2 to 5 C atoms, preferably having 3 to 5 C atoms, and
$R^{32}$ denotes an alkyl or alkoxy radical having 2 to 5 C atoms, preferably an alkoxy radical having 2 to 4 C atoms, or an alkenyloxy radical having 2 to 4 C atoms. The media according to the invention preferably comprise one or more compounds of the formula III-2, preferably one or more compounds selected from the group of the compounds of the formulae III-2-1 and III-2-2,

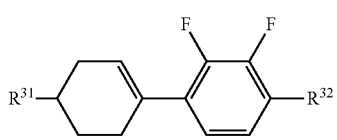

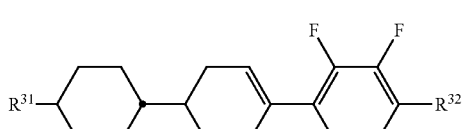

in which the parameters have the meanings given above for formula III-2, and preferably
$R^{31}$ denotes an alkyl radical having 2 to 5 C atoms, preferably having 3 to 5 C atoms, and
$R^{32}$ denotes an alkyl or alkoxy radical having 2 to 5 C atoms, preferably an alkoxy radical having 2 to 4 C atoms, or an alkenyloxy radical having 2 to 4 C atoms.

The media according to the invention preferably comprise one or more compounds of the formula III-3, preferably one or more compounds selected from the group of the compounds of the formulae III-3-1 and III-3-2,

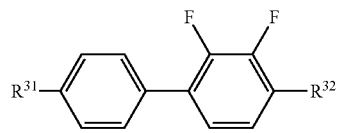

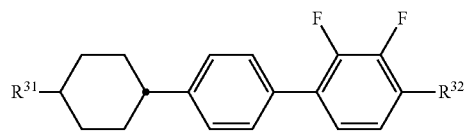

in which the parameters have the meanings given above for formula III-3, and preferably
$R^{31}$ denotes an alkyl radical having 2 to 5 C atoms, preferably having 3 to 5 C atoms, and
$R^{32}$ denotes an alkyl or alkoxy radical having 2 to 5 C atoms, preferably an alkoxy radical having 2 to 4 C atoms, or an alkenyloxy radical having 2 to 4 C atoms.

In a preferred embodiment, the media according to the invention comprise one or more compounds of the formula II selected from the group of the compounds of the formulae II-1 and II-2.

In a different preferred embodiment, the media according to the invention comprise no compounds of the formula II.

The media according to the invention preferably comprise the following compounds in the total concentrations stated:
10-60% by weight of one or more compounds of the formulae III-1 to III-4 and/or
30-80% by weight of one or more compounds of the formulae IV and/or V,
where the total content of all compounds in the medium is 100%.

In a particularly preferred embodiment, the media according to the invention comprise one or more compounds selected from the group of the compounds of the formulae OH-1 to OH-6,

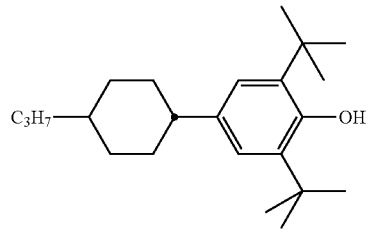

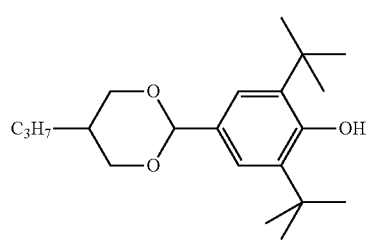

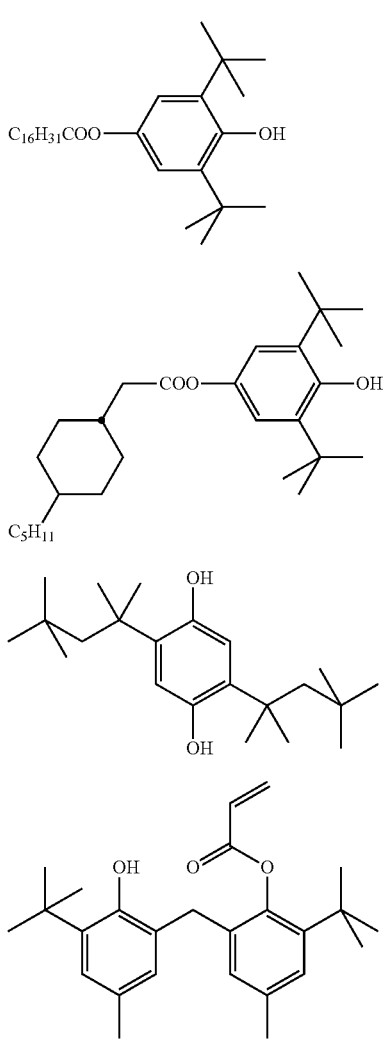

These compounds are highly suitable for the heat stabilization of the media.

In another preferred embodiment of the present invention, in which the media according to the invention comprise, in particular, one or more compounds of the formula I in which $R^{11}$, or at least one of $R^{11}$, denotes O• these media can also have adequate stability if they do not comprise a phenol compound, in particular selected from the group of the compounds of the formulae OH-1 to OH-6.

In a further preferred embodiment of the present invention, the media according to the invention at least in each case comprise one or more compounds of the formula I in which the groups $R^{11}$ of the one compound of the formula I have a different meaning than in the other compounds of the formula I.

The present invention also relates to electro-optical displays or electro-optical components which contain liquid-crystalline media according to the invention. Preference is given to electro-optical displays which are based on the VA or ECB effect and in particular those which are addressed by means of an active-matrix addressing device.

Accordingly, the present invention likewise relates to the use of a liquid-crystalline medium according to the invention in an electro-optical display or in an electro-optical component, and to a process for the preparation of the liquid-crystalline media according to the invention, characterized in that one or more compounds of the formula I are mixed with one or more compounds of the formula II, preferably with one or more compounds of the sub-formula II-1, and one or more further compounds, preferably selected from the group of the compounds of the formulae III-1 to III-4 and IV and/or V.

In addition, the present invention relates to a process for the stabilization of a liquid-crystalline medium which comprises one or more compounds of the formula II and one or more compounds selected from the group of the compounds of the formulae III-1 to III-4, characterized in that one or more compounds of the formula I are added to the medium.

In a further preferred embodiment, the medium comprises one or more compounds of the formula IV

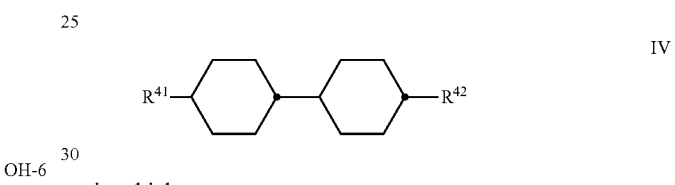

in which
$R^{41}$ denotes alkyl having 1 to 7 C atoms, preferably having 2 to C atoms, and
$R^{42}$ denotes alkyl having 1 to 7 C atoms or alkoxy having 1 to 6 C atoms, preferably having 2 to 5 C atoms.

In a further preferred embodiment, the medium comprises one or more compounds of the formula IV, selected from the group of the compounds of the formulae IV-1 and IV-2,

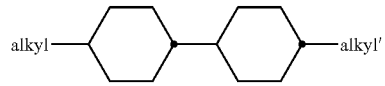

in which
alkyl and alkyl', independently of one another, denote alkyl having 1 to 7 C atoms, preferably having 2 to 5 C atoms, and
alkoxy denotes alkoxy having 1 to 5 C atoms, preferably having 2 to 4 C atoms.

In a further preferred embodiment, the medium comprises one or more compounds of the formula V

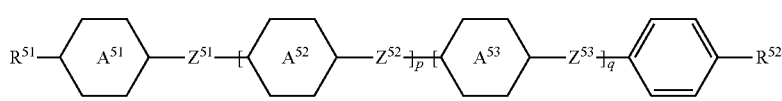

in which

R$^{51}$ and R$^{52}$, independently of one another, have one of the meanings given for R$^{21}$ and R$^{22}$ and preferably denote alkyl having 1 to 7 C atoms, preferably n-alkyl, particularly preferably n-alkyl having 1 to 5 C atoms,
alkoxy having 1 to 7 C atoms, preferably n-alkoxy, particularly preferably n-alkoxy having 2 to 5 C atoms,
alkoxyalkyl, alkenyl or alkenyloxy having 2 to 7 C atoms, preferably having 2 to 4 C atoms, preferably alkenyloxy,

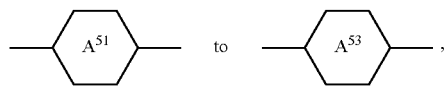

if present, each, independently of one another, denote

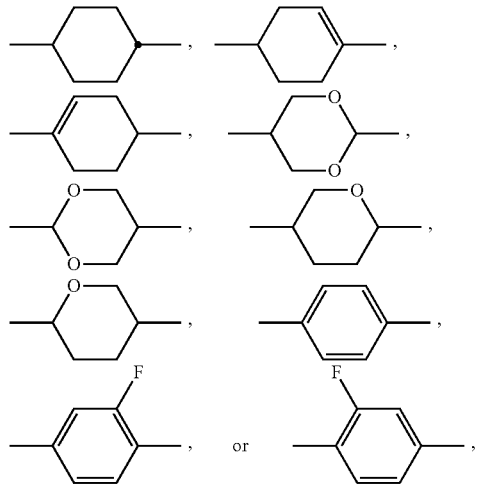

preferably

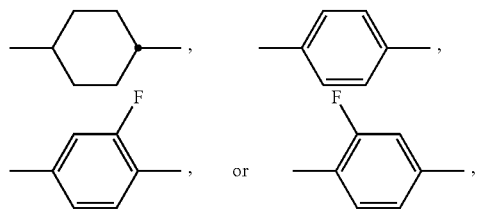

preferably

denotes

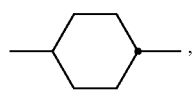

and, if present,

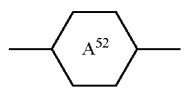

preferably denotes

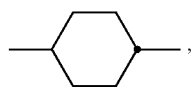

Z$^{51}$ to Z$^{53}$ each, independently of one another, denote —CH$_2$—CH$_2$—, —CH$_2$—O—, —CH=CH—, —C≡C—, —COO— or a single bond, preferably —CH$_2$—CH$_2$—, —CH$_2$—O— or a single bond and particularly preferably a single bond,
p and q each, independently of one another, denote 0 or 1,
(p+q) preferably denotes 0 or 1.

In a further preferred embodiment, the medium comprises one or more compounds of the formula V selected from the group of the compounds of the formulae V-1 to V-10, preferably selected from the group of the compounds of the formulae V-1 to V-5, V-1
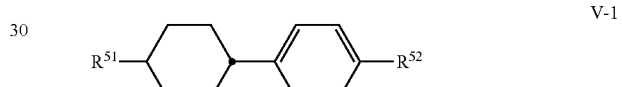

V-2
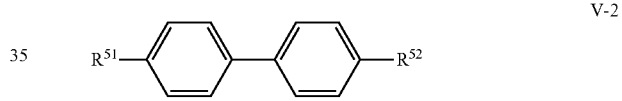

V-3
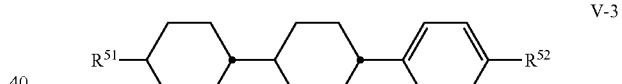

V-4
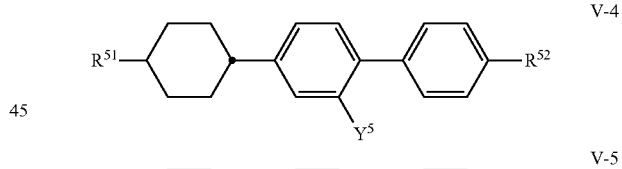

V-5
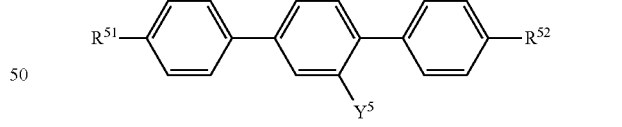

V-6
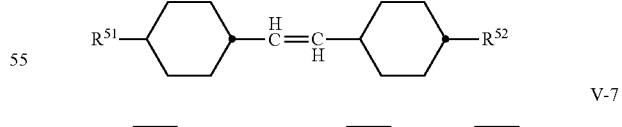

V-7
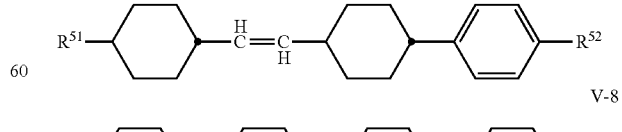

V-8
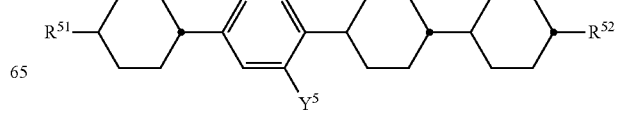

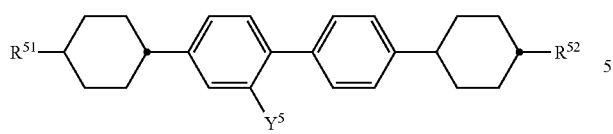

V-9

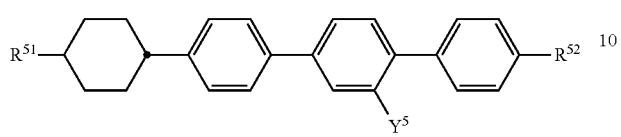

V-10 in which the parameters have the meanings given above under formula V, and

Y⁵ denotes H or F, and preferably

R⁵¹ denotes alkyl having 1 to 7 C atoms or alkenyl having 2 to 7 C atoms, and

R⁵² denotes alkyl having 1 to 7 C atoms, alkenyl having 2 to 7 C atoms or alkoxy having 1 to 6 C atoms, preferably alkyl or alkenyl, particularly preferably alkenyl.

In a further preferred embodiment, the medium comprises one or more compounds of the formula V-1 selected from the group of the compounds of the formulae V-1a and V-1b, preferably of the formula V-1b,

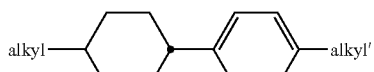

V-1a

V-1b in which alkyl and alkyl', independently of one another, denote alkyl having 1 to 7 C atoms, preferably having 2 to 5 C atoms, alkoxy denotes alkoxy having 1 to 5 C atoms, preferably having 2 to 4 C atoms.

In a further preferred embodiment, the medium comprises one or more compounds of the formula V-3 selected from the group of the compounds of the formulae V-3a and V-3b,

V-3a

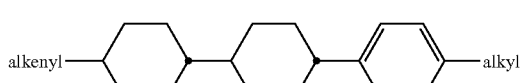

V-3b in which alkyl and alkyl', independently of one another, denote alkyl having 1 to 7 C atoms, preferably having 2 to 5 C atoms, alkoxy denotes alkoxy having 1 to 5 C atoms, preferably having 2 to 4 C atoms, and alkenyl denotes alkenyl having 2 to 7 C atoms, preferably having 2 to 5 C atoms.

In a further preferred embodiment, the medium comprises one or more compounds of the formula V-4 selected from the group of the compounds of the formulae V-4a and V-4b,

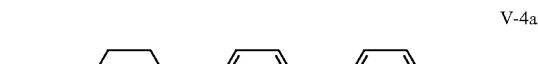

V-4a

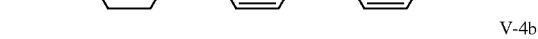

V-4b in which alkyl and alkyl', independently of one another, denote alkyl having 1 to 7 C atoms, preferably having 2 to 5 C atoms.

In a further preferred embodiment, the medium comprises one or more compounds of the formula III-4, preferably of the formula III-4-a,

III-4-a in which alkyl and alkyl', independently of one another, denote alkyl having 1 to 7 C atoms, preferably having 2 to 5 C atoms.

The liquid-crystal media in accordance with the present invention may comprise one or more chiral compounds.

Particularly preferred embodiments of the present invention meet one or more of the following conditions, where the acronyms (abbreviations) are explained in Tables A to C and illustrated by examples in Table D.

i. The liquid-crystalline medium has a birefringence of 0.060 or more, particularly preferably 0.070 or more.

ii. The liquid-crystalline medium has a birefringence of 0.130 or less, particularly preferably 0.120 or less.

iii. The liquid-crystalline medium has a birefringence in the range from 0.090 or more to 0.120 or less.

iv. The liquid-crystalline medium has a negative dielectric anisotropy having a value of 2.0 or more, particularly preferably 3.0 or more.

v. The liquid-crystalline medium has a negative dielectric anisotropy having a value of 5.5 or less, particularly preferably 4.0 or less.

vi. The liquid-crystalline medium has a negative dielectric anisotropy having a value in the range from 2.5 or more to 3.8 or less.

vii. The liquid-crystalline medium comprises one or more particularly preferred compounds of the formula II selected from the sub-formulae given below:

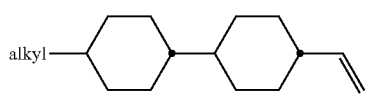

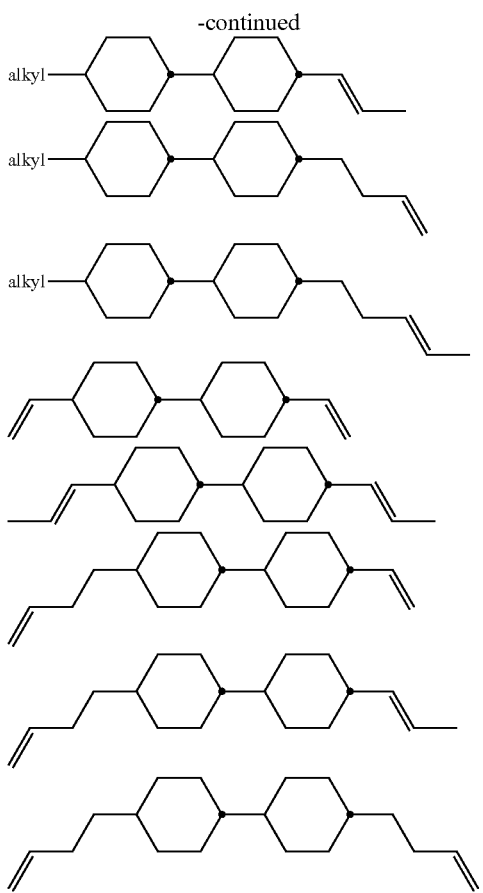

in which alkyl has the meaning given above and preferably, in each case independently of one another, denotes alkyl having 1 to 6, preferably having 2 to 5, C atoms and particularly preferably n-alkyl.

viii. The total concentration of the compounds of the formula II in the mixture as a whole is 25% or more, preferably 30% or more, and is preferably in the range from 25% or more to 49% or less, particularly preferably in the range from 29% or more to 47% or less, and very particularly preferably in the range from 37% or more to 44% or less.

ix. The liquid-crystalline medium comprises one or more compounds of the formula II selected from the group of the compounds of the following formulae: CC-n-V and/or CC-n-Vm, particularly preferably CC-3-V, preferably in a concentration of up to 50% or less, particularly preferably up to 42% or less, and optionally additionally CC-3-V1, preferably in a concentration of up to 15% or less, and/or CC-4-V, preferably in a concentration of up to 20% or less, particularly preferably up to 10% or less.

x. The total concentration of the compounds of the formula CC-3-V in the mixture as a whole is 20% or more, preferably 25% or more.

xi. The proportion of compounds of the formulae III-1 to III-4 in the mixture as a whole is 50% or more and preferably 75% or less.

xii. The liquid-crystalline medium essentially consists of compounds of the formulae I, II, III-1 to III-4, IV and V, preferably of compounds of the formulae I, II and III-1 to III-4.

xiii. The liquid-crystalline medium comprises one or more compounds of the formula IV, preferably in a total concentration of 5% or more, in particular 10% or more, and very particularly preferably 15% or more to 40% or less.

The invention furthermore relates to an electro-optical display having active-matrix addressing based on the VA or ECB effect, characterized in that it contains, as dielectric, a liquid-crystalline medium in accordance with the present invention.

The liquid-crystal mixture preferably has a nematic phase range having a width of at least 80 degrees and a flow viscosity $v_{20}$ of at most 30 mm$^2 \cdot$s$^{-1}$ at 20° C.

The liquid-crystal mixture according to the invention has a $\Delta \in$ of −0.5 to −8.0, in particular −1.5 to −6.0, and very particularly preferably −2.0 to −5.0, where $\Delta \in$ denotes the dielectric anisotropy.

The rotational viscosity $\gamma_1$ is preferably 120 mPa·s or less, in particular 100 mPa·s or less.

The mixtures according to the invention are suitable for all VA-TFT applications, such as, for example, VAN, MVA, (S)-PVA and ASV. They are furthermore suitable for IPS (in-plane switching), FFS (fringe-field switching) and PALO applications having negative $\Delta \in$.

The nematic liquid-crystal mixtures in the displays according to the invention generally comprise two components A and B, which themselves consist of one or more individual compounds.

The liquid-crystalline media according to the invention preferably comprise 4 to 15, in particular 5 to 12, and particularly preferably 10 or less, compounds. These are preferably selected from the group of the compounds of the formulae I, II and III-1 to III-4, and/or IV and/or V.

The liquid-crystalline media according to the invention may optionally also comprise 18 or more compounds. In this case, they preferably comprise 18 to 25 compounds.

Besides compounds of the formulae I to V, other constituents may also be present, for example in an amount of up to 45%, but preferably up to 35%, in particular up to 10%, of the mixture as a whole.

The media according to the invention may optionally also comprise a dielectrically positive component, whose total concentration is preferably 10% or less, based on the entire medium.

In a preferred embodiment, the liquid-crystal media according to the invention comprise in total, based on the mixture as a whole, 10 ppm or more to 1000 ppm or less, preferably 50 ppm or more to 500 ppm or less, particularly preferably 100 ppm or more to 400 ppm or less and very particularly preferably 150 ppm or more to 300 ppm or less, of the compound of the formula I, 20% or more to 60% or less, preferably 25% or more to 50% or less, particularly preferably 30% or more to 45% or less, of compounds of the formula II, and 50% or more to 70% or less of compounds of the formulae III-1 to III-4.

In a preferred embodiment, the liquid-crystal media according to the invention comprise compounds selected from the group of the compounds of the formulae I, II, III-1 to III-4, IV and V, preferably selected from the group of the compounds of the formulae I, II and III-1 to III-4; they preferably consist predominantly, particularly preferably essentially and very particularly preferably virtually completely of the compounds of the said formulae.

The liquid-crystal media according to the invention preferably have a nematic phase from in each case at least −20° C. or less to 70° C. or more, particularly preferably from −30° C. or less to 80° C. or more, very particularly preferably from −40° C. or less to 85° C. or more and most preferably from −40° C. or less to 90° C. or more.

The expression "have a nematic phase" here means on the one hand that no smectic phase and no crystallization are observed at low temperatures at the corresponding temperature and on the other hand that no clearing occurs on heating out of the nematic phase. The investigation at low temperatures is carried out in a flow viscometer at the corresponding temperature and checked by storage in test cells having a cell thickness corresponding to the electro-optical application for at least 100 hours. If the storage stability at a temperature of −20° C. in a corresponding test cell is 1000 h or more, the medium is regarded as stable at this temperature. At temperatures of −30° C. and −40° C., the corresponding times are 500 h and 250 h respectively. At high temperatures, the clearing point is measured in capillaries by conventional methods.

In a preferred embodiment, the liquid-crystal media according to the invention are characterized by optical anisotropy values in the moderate to low range. The birefringence values are preferably in the range from 0.065 or more to 0.130 or less, particularly preferably in the range from 0.080 or more to 0.120 or less and very particularly preferably in the range from 0.085 or more to 0.110 or less.

In this embodiment, the liquid-crystal media according to the invention have negative dielectric anisotropy and relatively high absolute values of the dielectric anisotropy ($|\Delta\epsilon|$) which are preferably in the range from 2.7 or more to 5.3 or less, preferably to 4.5 or less, preferably from 2.9 or more to 4.5 or less, particularly preferably from 3.0 or more to 4.0 or less and very particularly preferably from 3.5 or more to 3.9 or less.

The liquid-crystal media according to the invention have relatively low values for the threshold voltage ($V_0$) in the range from 1.7 V or more to 2.5 V or less, preferably from 1.8 V or more to 2.4 V or less, particularly preferably from 1.9 V or more to 2.3 V or less and very particularly preferably from 1.95 V or more to 2.1 V or less.

In a further preferred embodiment, the liquid-crystal media according to the invention preferably have relatively low values of the average dielectric anisotropy ($\epsilon_{av.} \equiv (\epsilon_{\parallel} + 2\epsilon_{\perp})/3$) which are preferably in the range from 5.0 or more to 7.0 or less, preferably from 5.5 or more to 6.5 or less, still more preferably from 5.7 or more to 6.4 or less, particularly preferably from 5.8 or more to 6.2 or less and very particularly preferably from 5.9 or more to 6.1 or less.

In addition, the liquid-crystal media according to the invention have high values for the VHR in liquid-crystal cells.

In freshly filled cells at 20° C. in the cells, these are greater than or equal to 95%, preferably greater than or equal to 97%, particularly preferably greater than or equal to 98% and very particularly preferably greater than or equal to 99%, and after 5 minutes in the oven at 100° C. in the cells, these are greater than or equal to 90%, preferably greater than or equal to 93%, particularly preferably greater than or equal to 96% and very particularly preferably greater than or equal to 98%.

In general, liquid-crystal media having a low addressing voltage or threshold voltage here have a lower VHR than those having a higher addressing voltage or threshold voltage, and vice versa.

These preferred values for the individual physical properties are preferably also in each case maintained by the media according to the invention in combination with one another.

In the present application, the term "compounds", also written as "compound(s)", means both one and also a plurality of compounds, unless explicitly indicated otherwise.

Unless indicated otherwise, the individual compounds are generally employed in the mixtures in concentrations in each case from 1% or more to 30% or less, preferably from 2% or more to 30% or less and particularly preferably from 3% or more to 16% or less.

In a preferred embodiment, the liquid-crystalline media according to the invention comprise
the compound of the formula I,
one or more compounds of the formula II, preferably selected from the group of the compounds of the formulae CC-n-V and CC-n-Vm, preferably CC-3-V, CC-3-V1, CC-4-V and CC-5-V, particularly preferably selected from the group of the compounds CC-3-V, CC-3-V1 and CC-4-V, very particularly preferably the compound CC-3-V, and optionally additionally the compound(s) CC-4-V and/or CC-3-V1,
one or more compounds of the formula III-1-1, preferably of the formula CY-n-Om, selected from the group of the compounds of the formulae CY-3-O2, CY-3-O4, CY-5-O2 and CY-5-O4,
one or more compounds of the formula III-1-2, preferably selected from the group of the compounds of the formulae CCY-n-m and CCY-n-Om, preferably of the formula CCY-n-Om, preferably selected from the group of the compounds of the formulae CCY-3-O2, CCY-2-O2, CCY-3-O1, CCY-3-O3, CCY-4-O2, CCY-3-O2 and CCY-5-O2,
optionally, preferably obligatorily, one or more compounds of the formula III-2-2, preferably of the formula CLY-n-Om, preferably selected from the group of the compounds of the formulae CLY-2-O4, CLY-3-O2, CLY-3-O3,
one or more compounds of the formula III-3-2, preferably of the formula CPY-n-Om, preferably selected from the group of the compounds of the formulae CPY-2-O2 and CPY-3-O2, CPY-4-O2 and CPY-5-O2,
one or more compounds of the formula III-4, preferably of the formula PYP-n-m, preferably selected from the group of the compounds of the formulae PYP-2-3 and PYP-2-4.

For the present invention, the following definitions apply in connection with the specification of the constituents of the compositions, unless indicated otherwise in individual cases:
"comprise": the concentration of the constituents in question in the composition is preferably 5% or more, particularly preferably 10% or more, very particularly preferably 20% or more,
"predominantly consist of": the concentration of the constituents in question in the composition is preferably 50% or more, particularly preferably 55% or more and very particularly preferably 60% or more,
"essentially consist of": the concentration of the constituents in question in the composition is preferably 80% or more, particularly preferably 90% or more and very particularly preferably 95% or more, and
"virtually completely consist of": the concentration of the constituents in question in the composition is preferably 98% or more, particularly preferably 99% or more and very particularly preferably 100.0%.

This applies both to the media as compositions with their constituents, which can be components and compounds, and also to the components with their constituents, the compounds. Only in relation to the concentration of an individual compound relative to the medium as a whole does the term comprise mean: the concentration of the compound in question is preferably 1% or more, particularly preferably 2% or more, very particularly preferably 4% or more.

For the present invention, "≦" means less than or equal to, preferably less than, and "≧" means greater than or equal to, preferably greater than.

For the present invention,

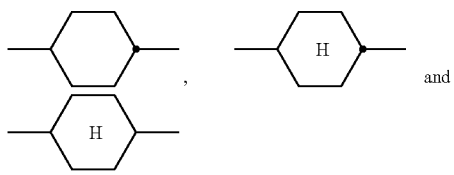

denote trans-1,4-cyclohexylene, and

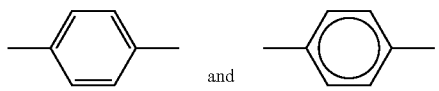

denote 1,4-phenylene.

For the present invention, the expression "dielectrically positive compounds" means compounds having a $\Delta\epsilon$ of $>1.5$, the expression "dielectrically neutral compounds" means those where $-1.5 \leq \Delta\epsilon \leq 1.5$ and the expression "dielectrically negative compounds" means those where $\Delta\epsilon < -1.5$. The dielectric anisotropy of the compounds is determined here by dissolving 10% of the compounds in a liquid-crystalline host and determining the capacitance of the resultant mixture in each case in at least one test cell having a cell thickness of 20 µm with homeotropic and with homogeneous surface alignment at 1 kHz. The measurement voltage is typically 0.5 V to 1.0 V, but is always lower than the capacitive threshold of the respective liquid-crystal mixture investigated.

The host mixture used for dielectrically positive and dielectrically neutral compounds is ZLI-4792 and that used for dielectrically negative compounds is ZLI-2857, both from Merck KGaA, Germany. The values for the respective compounds to be investigated are obtained from the change in the dielectric constant of the host mixture after addition of the compound to be investigated and extrapolation to 100% of the compound employed. The compound to be investigated is dissolved in the host mixture in an amount of 10%. If the solubility of the substance is too low for this purpose, the concentration is halved in steps until the investigation can be carried out at the desired temperature.

The liquid-crystal media according to the invention may, if necessary, also comprise further additives, such as, for example, stabilizers and/or pleochroic dyes and/or chiral dopants in the usual amounts. The amount of these additives employed is preferably in total 0% or more to 10% or less, based on the amount of the entire mixture, particularly preferably 0.1% or more to 6% or less. The concentration of the individual compounds employed is preferably 0.1% or more to 3% or less. The concentration of these and similar additives is generally not taken into account when specifying the concentrations and concentration ranges of the liquid-crystal compounds in the liquid-crystal media.

In a preferred embodiment, the liquid-crystal media according to the invention comprise a polymer precursor which comprises one or more reactive compounds, preferably reactive mesogens, and, if necessary, also further additives, such as, for example, polymerization initiators and/or polymerization moderators, in the usual amounts. The amount of these additives employed is in total 0% or more to 10% or less, based on the amount of the entire mixture, preferably 0.1% or more to 2% or less. The concentration of these and similar additives is not taken into account when specifying the concentrations and concentration ranges of the liquid-crystal compounds in the liquid-crystal media.

The compositions consist of a plurality of compounds, preferably 3 or more to 30 or fewer, particularly preferably 6 or more to 20 or fewer and very particularly preferably 10 or more to 16 or fewer compounds, which are mixed in a conventional manner. In general, the desired amount of the components used in lesser amount is dissolved in the components making up the principal constituent of the mixture. This is advantageously carried out at elevated temperature. If the selected temperature is above the clearing point of the principal constituent, completion of the dissolution operation is particularly easy to observe. However, it is also possible to prepare the liquid-crystal mixtures in other conventional ways, for example using pre-mixes or from a so-called "multibottle system".

The mixtures according to the invention exhibit very broad nematic phase ranges having clearing points of 65° C. or more, very favorable values for the capacitive threshold, relatively high values for the holding ratio and at the same time very good low-temperature stabilities at $-30°$ C. and $-40°$ C. Furthermore, the mixtures according to the invention are distinguished by low rotational viscosities $\gamma_1$.

It goes without saying to the person skilled in the art that the media according to the invention for use in VA, IPS, FFS or PALC displays may also comprise compounds in which, for example, H, N, O, Cl, F have been replaced by the corresponding isotopes.

The structure of the liquid-crystal displays according to the invention corresponds to the usual geometry, as described, for example, in EP-A 0 240 379.

The liquid-crystal phases according to the invention can be modified by means of suitable additives in such a way that they can be employed in any type of, for example, ECB, VAN, IPS, GH or ASM-VA LCD display that has been disclosed to date.

Table E below indicates possible dopants which can be added to the mixtures according to the invention. If the mixtures comprise one or more dopants, it is (they are) employed in amounts of 0.01 to 4%, preferably 0.1 to 1.0%.

Stabilizers which can be added, for example, to the mixtures according to the invention, preferably in amounts of 0.01 to 6%, in particular 0.1 to 3%, are shown below in Table F.

For the purposes of the present invention, all concentrations are, unless explicitly noted otherwise, indicated in percent by weight and relate to the corresponding mixture or mixture component, unless explicitly indicated otherwise.

All temperature values indicated in the present application, such as, for example, the melting point T(C,N), the smectic (S) to nematic (N) phase transition T(S,N) and the clearing point T(N,I), are indicated in degrees Celsius (° C.) and all temperature differences are correspondingly indicated in differential degrees (° or degrees), unless explicitly indicated otherwise.

For the present invention, the term "threshold voltage" relates to the capacitive threshold ($V_0$), also known as the Freedericks threshold, unless explicitly indicated otherwise.

All physical properties are and have been determined in accordance with "Merck Liquid Crystals, Physical Properties of Liquid Crystals", status November 1997, Merck KGaA, Germany, and apply for a temperature of 20° C., and $\Delta n$ is determined at 589 nm and $\Delta\epsilon$ at 1 kHz, unless explicitly indicated otherwise in each case.

The electro-optical properties, for example the threshold voltage ($V_0$) (capacitive measurement), are, as is the switching behavior, determined in test cells produced at Merck Japan. The measurement cells have soda-lime glass substrates and are constructed in an ECB or VA configuration with polyimide alignment layers (SE-1211 with diluent **26 (mixing ratio 1:1), both from Nissan Chemicals, Japan), which have been rubbed perpendicularly to one another and effect homeotropic alignment of the liquid crystals. The surface area of the transparent, virtually square ITO electrodes is 1 cm$^2$.

Unless indicated otherwise, a chiral dopant is not added to the liquid-crystal mixtures used, but the latter are also particularly suitable for applications in which doping of this type is necessary.

The VHR is determined in test cells produced at Merck Japan. The measurement cells have soda-lime glass substrates and are constructed with polyimide alignment layers (AL-3046 from Japan Synthetic Rubber, Japan) with a layer thickness of 50 nm, which have been rubbed perpendicularly to one another. The layer thickness is a uniform 6.0 μm. The surface area of the transparent ITO electrodes is 1 cm$^2$.

The VHR is determined at 20° C. (VHR$_{20}$) and after 5 minutes in an oven at 100° C. (VHR$_{100}$) in a commercially available instrument from Autronic Melchers, Germany. The voltage used has a frequency of 60 Hz.

The accuracy of the VHR measurement values depends on the respective value of the VHR. The accuracy decreases with decreasing values. The deviations generally observed in the case of values in the various magnitude ranges are compiled in their order of magnitude in the following table.

| VHR range VHR values | | Deviation (relative) $\Delta_G$VHR/VHR/% |
|---|---|---|
| from | to | Approx. |
| 99.6% | 100% | +/−0.1 |
| 99.0% | 99.6% | +/−0.2 |
| 98% | 99% | +/−0.3 |
| 95% | 98% | +/−0.5 |
| 90% | 95% | +/−1 |
| 80% | 90% | +/−2 |
| 60% | 80% | +/−4 |
| 40% | 60% | +/−8 |
| 20% | 40% | +/−10 |
| 10% | 20% | +/−20 |

The stability to UV irradiation is investigated in a "Suntest CPS", a commercial instrument from Heraeus, Germany. The sealed test cells are irradiated for 2.0 hours without additional heating. The irradiation power in the wavelength range from 300 nm to 800 nm is 765 W/m$^2$ V. A UV "cut-off" filter having an edge wavelength of 310 nm is used in order to simulate the so-called window glass mode. In each series of experiments, at least four test cells are investigated for each condition, and the respective results are indicated as averages of the corresponding individual measurements.

The decrease in the voltage holding ratio (ΔVHR) usually caused by the exposure, for example by UV irradiation by LCD backlighting, is determined in accordance with the following equation (1):

$$\Delta VHR(t) = VHR(t) - VHR(t=0) \quad (1).$$

The relative stability (S$_{rel}$) of an LC mixture to a load for a time t is determined in accordance with the following equation, equation (2):

$$S_{rel}(t) = \frac{VHRref(t=0) - VHRref(t)}{VHR(t=0) - VHR(t)}, \quad (2)$$

where "ref" stands for the corresponding unstabilized mixture.

A further characteristic quantity which, besides the VHR, can characterize the conductivity of the liquid-crystal mixtures is the ion density. High values of the ion density often result in the occurrence of display faults, such as image sticking and flickering. The ion density is preferably determined in test cells produced at Merck Japan Ltd. The test cells have substrates made from soda-lime glass and are designed with polyimide alignment layers (AL-3046 from Japan Synthetic Rubber, Japan) having a polyimide layer thickness of 40 nm. The layer thickness of the liquid-crystal mixture is a uniform 5.8 μm. The area of the circular, transparent ITO electrodes, which are additionally fitted with a guard ring, is 1 cm$^2$. The accuracy of the measurement method is about ±15%. The cells are dried overnight in an oven at 120° C. before filling with the relevant liquid-crystal mixture.

The ion density is measured using a commercially available instrument from TOYO, Japan. The measurement method is essentially a measurement method which is analogous to cyclic voltammetry, as described in M. Inoue, "Recent Measurement of Liquid Crystal Material Characteristics", Proceedings IDW 2006, LCT-7-1,647. In this method, an applied direct voltage is varied between a positive and negative maximum value in accordance with a pre-specified triangular profile. A complete run through the profile thus forms one measurement cycle. If the applied voltage is sufficiently large that the ions in the field are able to move to the respective electrode, an ion current forms due to discharge of the ions. The amount of charge transferred here is typically in the range from a few pC to a few nC. This makes highly sensitive detection necessary, which is ensured by the above-mentioned instrument. The results are depicted in a current/voltage curve. The ion current here is evident from the occurrence of a peak at voltages which are smaller than the threshold voltage of the liquid crystal mixture. Integration of the peak area gives the value for the ion density of the mixture investigated. Four test cells are measured per mixture. The repetition frequency of the triangular voltage is 0.033 Hz, the measurement temperature is 60° C., the maximum voltage is ±3 V to ±10 V, depending on the magnitude of the dielectric anisotropy of the relevant mixture.

The rotational viscosity is determined using the rotating permanent magnet method and the flow viscosity in a modified Ubbelohde viscometer. For liquid-crystal mixtures ZLI-2293, ZLI-4792 and MLC-6608, all products from Merck KGaA, Darmstadt, Germany, the rotational viscosity values determined at 20° C. are 161 mPa·s, 133 mPa·s and 186 mPa·s respectively, and the flow viscosity values (v) are 21 mm$^2$·s$^{-1}$, 14 mm$^2$·s$^{-1}$ and 27 mm$^2$·s$^{-1}$ respectively.

The following symbols are used, unless explicitly indicated otherwise:

V$_0$ threshold voltage, capacitive [V] at 20° C.,
n$_e$ extraordinary refractive index measured at 20° C. and 589 nm,
n$_o$ ordinary refractive index measured at 20° C. and 589 nm,
Δn optical anisotropy measured at 20° C. and 589 nm,
∈$_\perp$ dielectric susceptibility perpendicular to the director at 20° C. and 1 kHz,
Δ$_\parallel$ dielectric susceptibility parallel to the director at 20° C. and 1 kHz,
Δ∈ dielectric anisotropy at 20° C. and 1 kHz, cl.p. or
T(N,I) clearing point [° C.],
ν flow viscosity measured at 20° C. [mm$^2$·s$^{-1}$],
γ$_1$ rotational viscosity measured at 20° C. [mPa·s],
K$_1$ elastic constant, "splay" deformation at 20° C. [pN],
K$_2$ elastic constant, "twist" deformation at 20° C. [pN],
K$_3$ elastic constant, "bend" deformation at 20° C. [pN], and
LTS low-temperature stability of the phase, determined in test cells,
VHR voltage holding ratio,
ΔVHR decrease in the voltage holding ratio,
S$_{rel}$ relative stability of the VHR.

The following examples explain the present invention without limiting it. However, they show the person skilled in the art preferred mixture concepts with compounds preferably to be employed and the respective concentrations thereof and combinations thereof with one another. In addition, the examples illustrate the properties and property combinations that are accessible.

For the present invention and in the following examples, the structures of the liquid-crystal compounds are indicated by means of acronyms, with the transformation into chemical formulae taking place in accordance with Tables A to C below. All radicals C$_n$H$_{2n+1}$, C$_m$H$_{2m+1}$ and C$_l$H$_{2l+1}$ or C$_n$H$_{2n}$, C$_m$H$_{2m}$ and C$_l$H$_{2l}$ are straight-chain alkyl radicals or alkylene radicals, in each case having n, m and l C atoms respectively. Table A shows the codes for the ring elements of the nuclei of the compound, Table B lists the bridging units, and Table C lists the meanings of the symbols for the left- and right-hand end groups of the molecules. The acronyms are composed of the codes for the ring elements with optional linking groups, followed by a first hyphen and the codes for the left-hand end group, and a second hyphen and the codes for the right-hand end group. Table D shows illustrative structures of compounds together with their respective abbreviations.

TABLE A

Ring elements

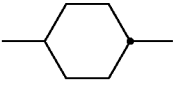
C

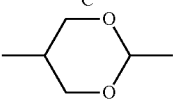
D

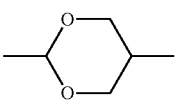
DI

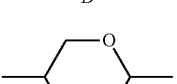
A

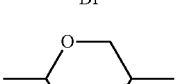
AI

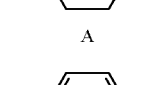
P

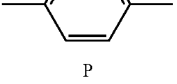
G

GI

TABLE A-continued

Ring elements

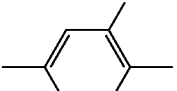
U

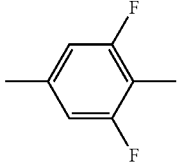
UI

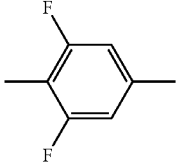
Y

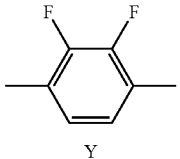
P(F, Cl)Y

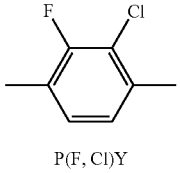
P(Cl,F)Y

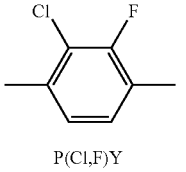
np

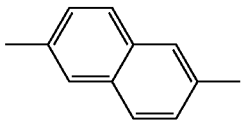
n3f

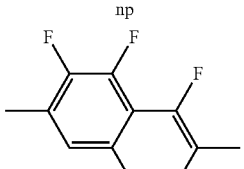
nN3fl

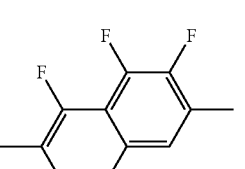
th

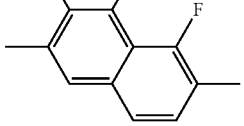
thl

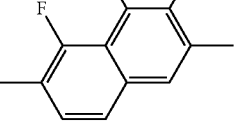
tH2f

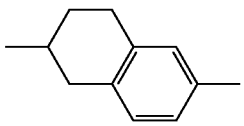
tH2fl

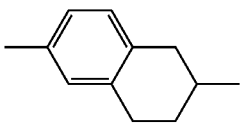
o2f

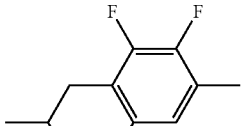
o2fl

TABLE A-continued

Ring elements

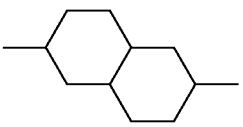

dh

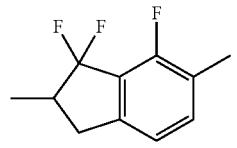

K    KI

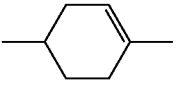

L    LI

TABLE A-continued

Ring elements

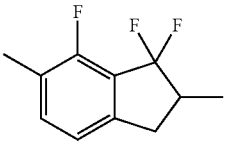

F    FI

TABLE B

| | Bridging units | | |
|---|---|---|---|
| E | —CH$_2$—CH$_2$— | | |
| V | —CH=CH— | | |
| T | —C≡C— | | |
| W | —CF$_2$—CF$_2$— | | |
| B | —CF=CF— | | |
| Z | —CO—O— | ZI | —O—CO— |
| X | —CF=CH— | XI | —CH=CF— |
| O | —CH$_2$—O— | OI | —O—CH$_2$— |
| Q | —CF$_2$—O— | QI | —O—CF$_2$— |

TABLE C

End groups

| On the left individually or in combination | | On the right individually or in combination | |
|---|---|---|---|
| -n- | C$_n$H$_{2n+1}$— | -n | —C$_n$H$_{2n+1}$ |
| -nO- | C$_n$H$_{2n+1}$—O— | -nO | —O—C$_n$H$_{2n+1}$ |
| -V- | CH$_2$=CH— | -V | —CH=CH$_2$ |
| -nV- | C$_n$H$_{2n+1}$—CH=CH— | -nV | —C$_n$H$_{2n}$—CH=CH$_2$ |
| -Vn- | CH$_2$=CH—C$_n$H$_{2n}$— | -Vn | —CH=CH—C$_n$H$_{2n+1}$ |
| -nVm- | C$_n$H$_{2n+1}$—CH=CH—C$_m$H$_{2m}$— | -nVm | —C$_n$H$_{2n}$—CH=CH—C$_m$H$_{2m+1}$ |
| -N- | N≡C— | -N | —C≡N |
| -S- | S=C=N— | -S | —N=C=S |
| -F- | F— | -F | —F |
| -CL- | Cl— | -CL | —Cl |
| -M- | CFH$_2$— | -M | —CFH$_2$ |
| -D- | CF$_2$H— | -D | —CF$_2$H |
| -T- | CF$_3$— | -T | —CF$_3$ |
| -MO- | CFH$_2$O— | -OM | —OCFH$_2$ |
| -DO- | CF$_2$HO— | -OD | —OCF$_2$H |
| -TO- | CF$_3$O— | -OT | —OCF$_3$ |
| -A- | H—C≡C— | -A | —C≡C—H |
| -nA- | C$_n$H$_{2n+1}$—C≡C— | -An | —C≡C—C$_n$H$_{2n+1}$ |
| -NA- | N≡C—C≡C— | -AN | —C≡C—C≡N |

| On the left only in combination | | On the right only in combination | |
|---|---|---|---|
| -...n...- | —C$_n$H$_{2n}$— | -...n... | —C$_n$H$_{2n}$— |
| -...M...- | —CFH— | -...M... | —CFH— |
| -...D...- | —CF$_2$— | -...D... | —CF$_2$— |
| -...V...- | —CH=CH— | -...V... | —CH=CH— |
| -...Z...- | —CO—O— | -...Z... | —CO—O— |
| -...ZI...- | —O—CO— | -...ZI... | —O—CO— |
| -...K...- | —CO— | -...K... | —CO— |
| -...W...- | —CF=CF— | -...W... | —CF=CF— | in which n and m are each integers, and the three dots "..." are placeholders for other abbreviations from this table.

Besides the compounds of the formula I, the mixtures according to the invention preferably comprise one or more compounds of the compounds mentioned below.
The following abbreviations are used:
(n, m and z are, independently of one another, each an integer, preferably 1 to 6)
TABLE D
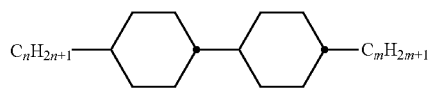
CC-n-m
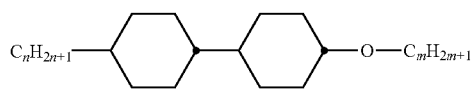
CC-n-Om
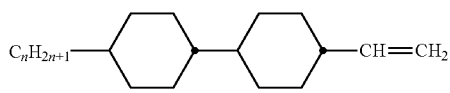
CC-n-V
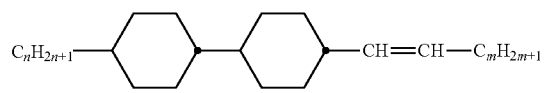
CC-n-Vm
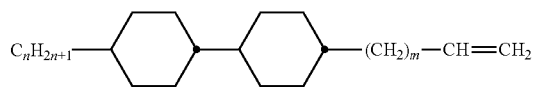
CC-n-mV
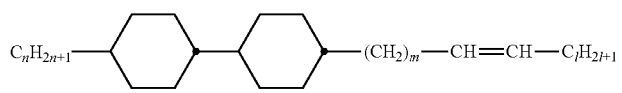
CC-n-mVl
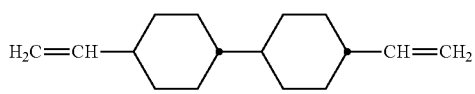
CC-V-V
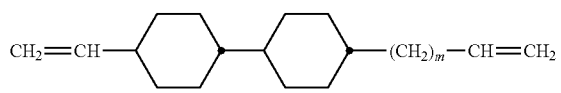
CC-V-mV
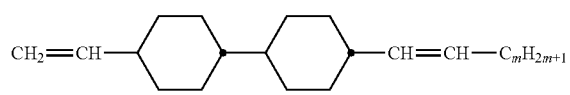
CC-V-Vm
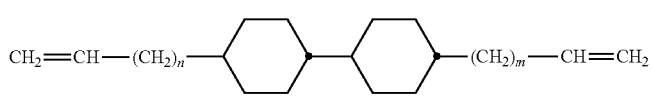
CC-Vn-mV TABLE D-continued
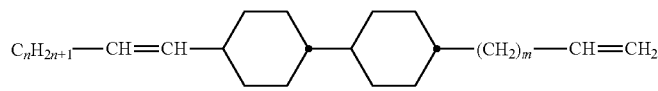
CC-nV-mV
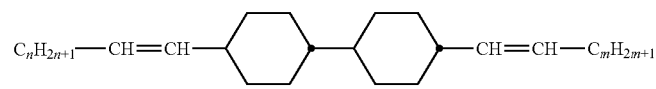
CC-nV-Vm
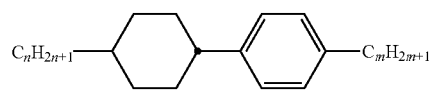
CP-n-m
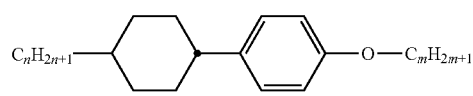
CP-n-Om
CCP-n-m
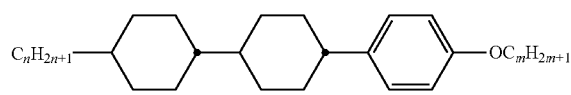
CCP-n-Om
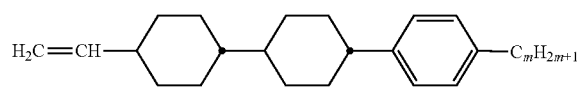
CCP-V-m
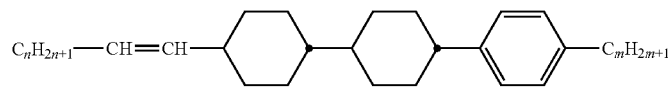
CCP-nV-m
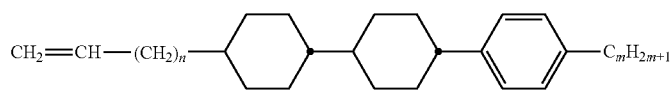
CCP-Vn-m
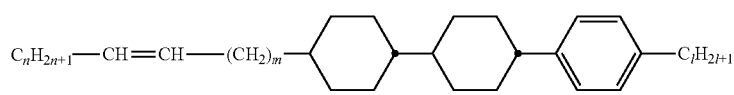
CCP-nVm-l
CPP-n-m TABLE D-continued
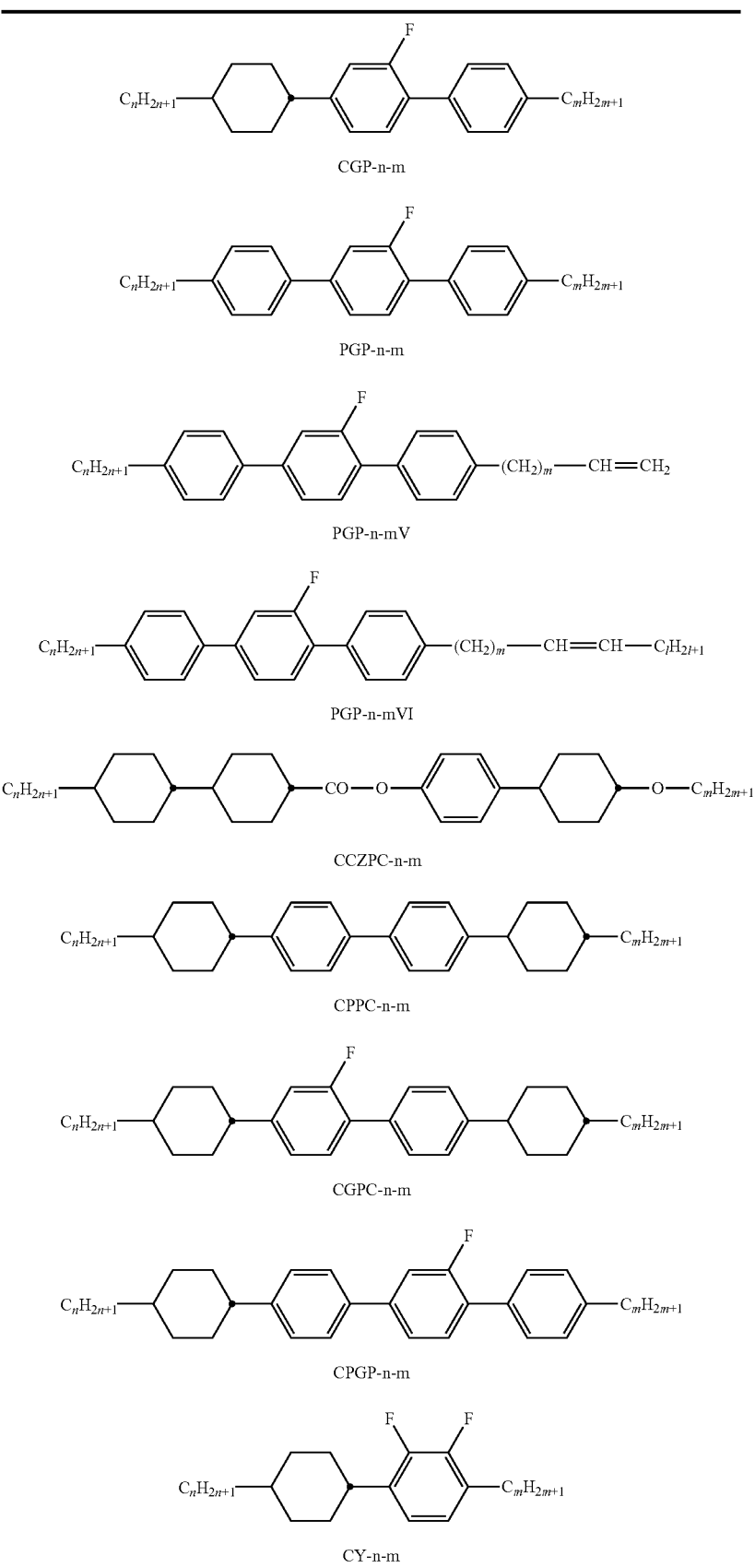

TABLE D-continued
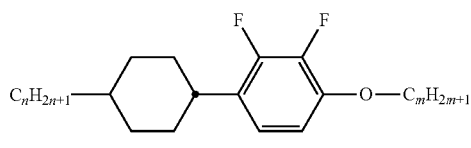
CY-n-Om
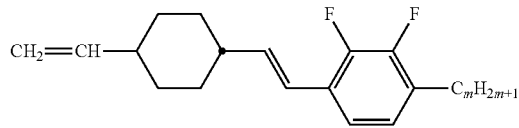
CVY-n-m
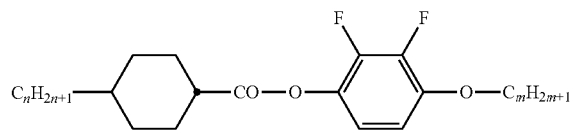
CZY-n-Om
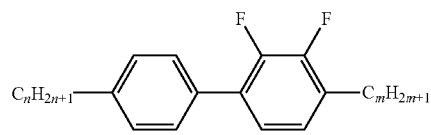
PY-n-m
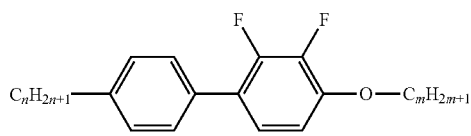
PY-n-Om
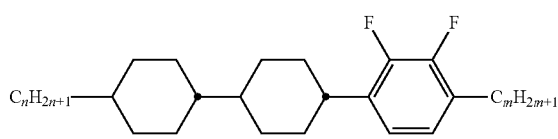
CCY-n-m
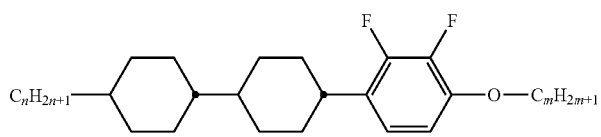
CCY-n-Om
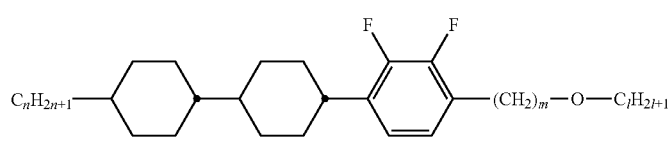
CCY-n-mOl TABLE D-continued
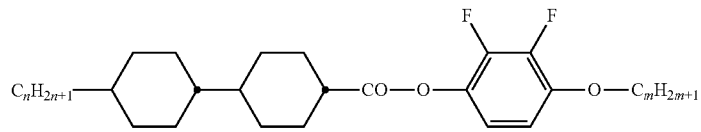
CCZY-n-Om
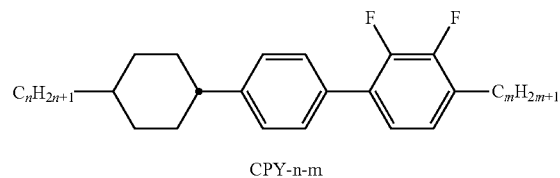
CPY-n-m
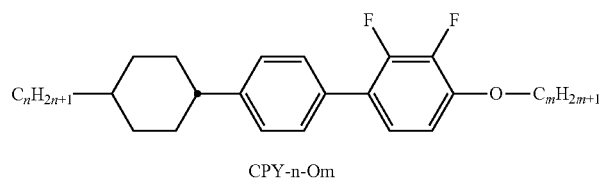
CPY-n-Om
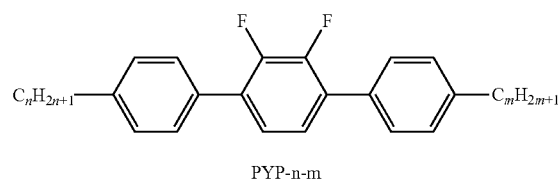
PYP-n-m
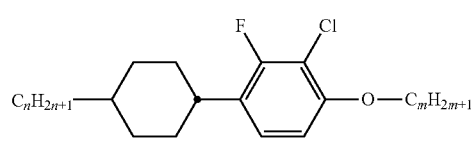
CP(F,Cl)-n-Om
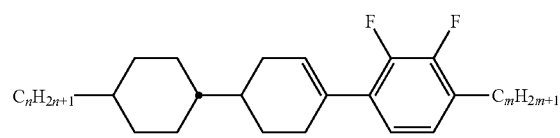
CLY-n-m
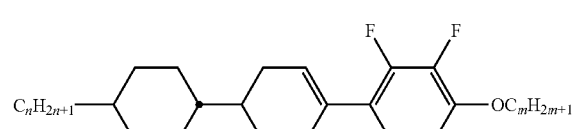
CLY-n-Om
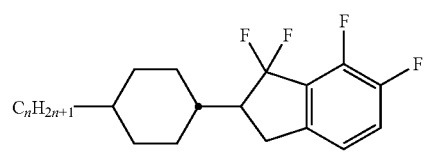
CK-n-F TABLE D-continued
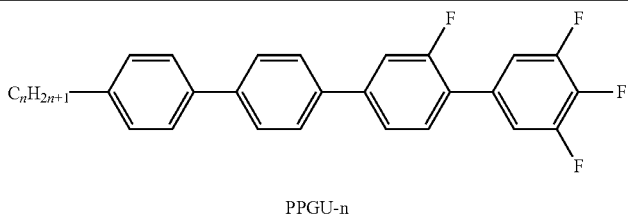
PPGU-n
Table E shows chiral dopants which are preferably employed in the mixtures according to the invention.
TABLE E
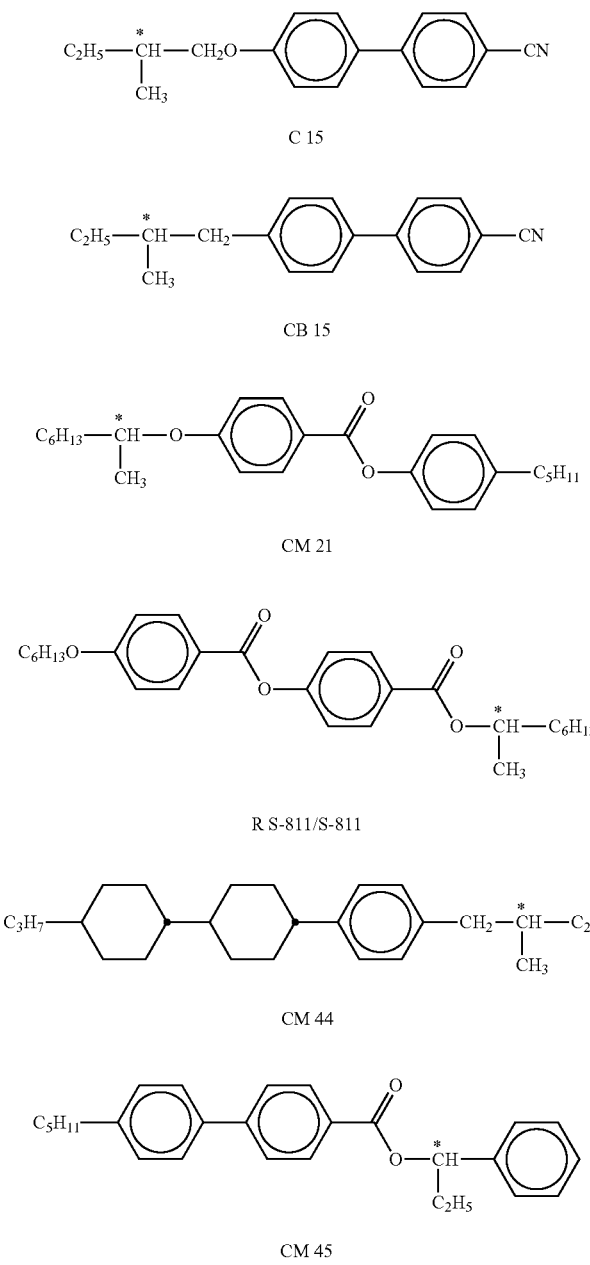

TABLE E-continued
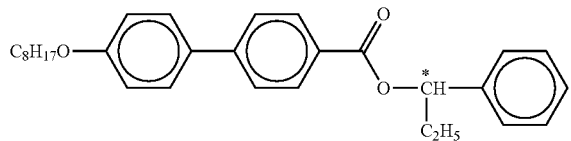
CM 47
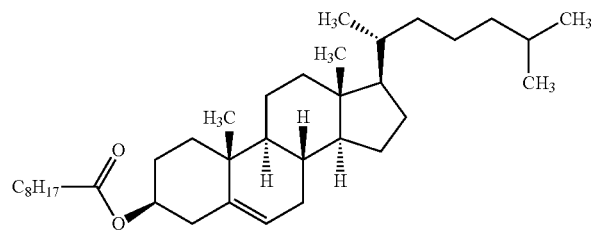
CN
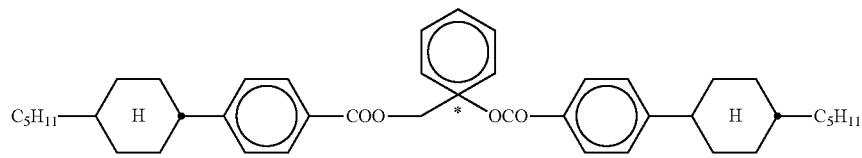
R-1011/S-1011
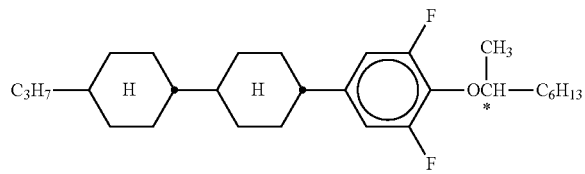
R-2011/S-2011
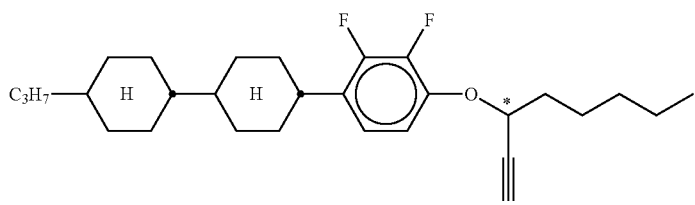
R-3011/S-3011
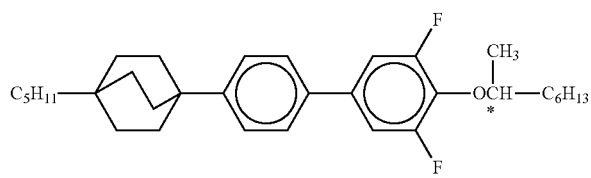
R-4011/S-4011

TABLE E-continued

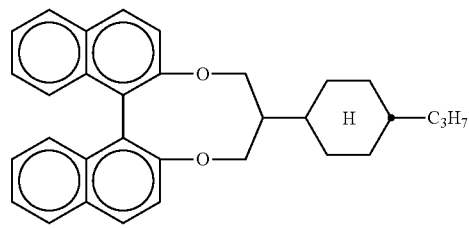

R-5011/S-5011

In a preferred embodiment of the present invention, the media according to the invention comprise one or more compounds selected from the group of the compounds from Table E.

Table F shows stabilizers which can preferably be employed in the mixtures according to the invention in addition to the compounds of the formula I. The parameter n here denotes an integer in the range from 1 to 12. In particular, the phenol derivatives shown can be employed as additional stabilizers since they act as antioxidants.

TABLE F

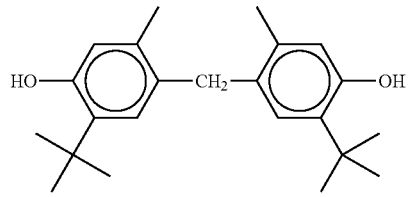

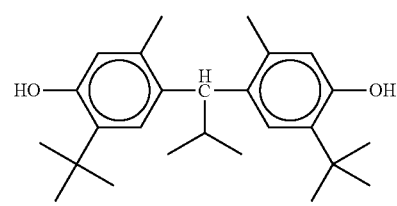

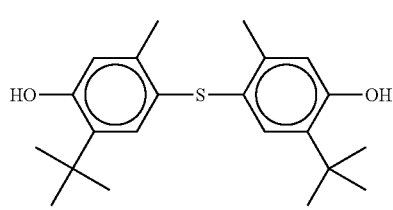

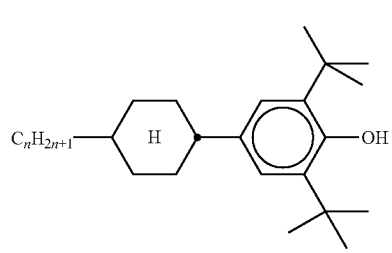

TABLE F-continued

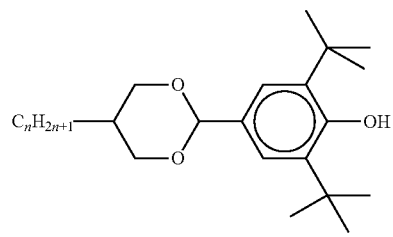

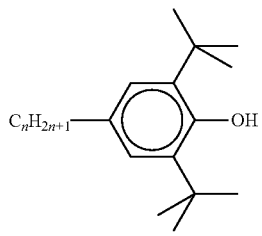

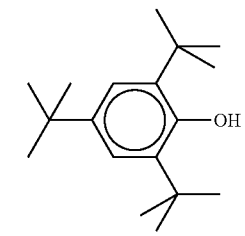

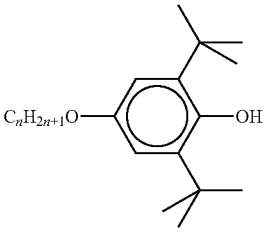

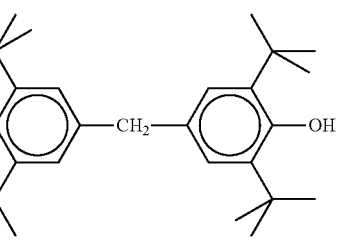

TABLE F-continued
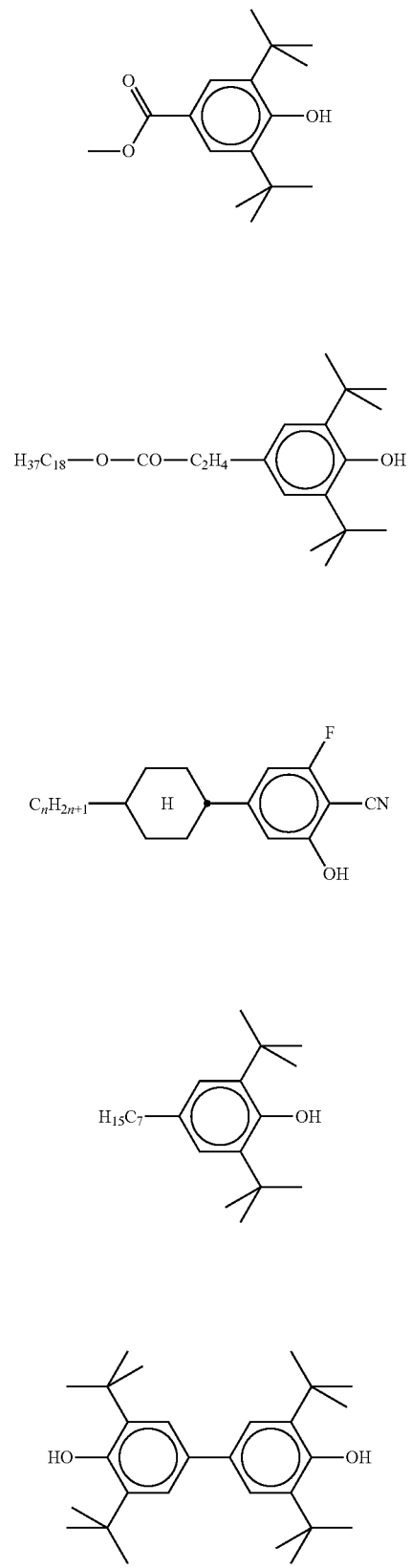
TABLE F-continued
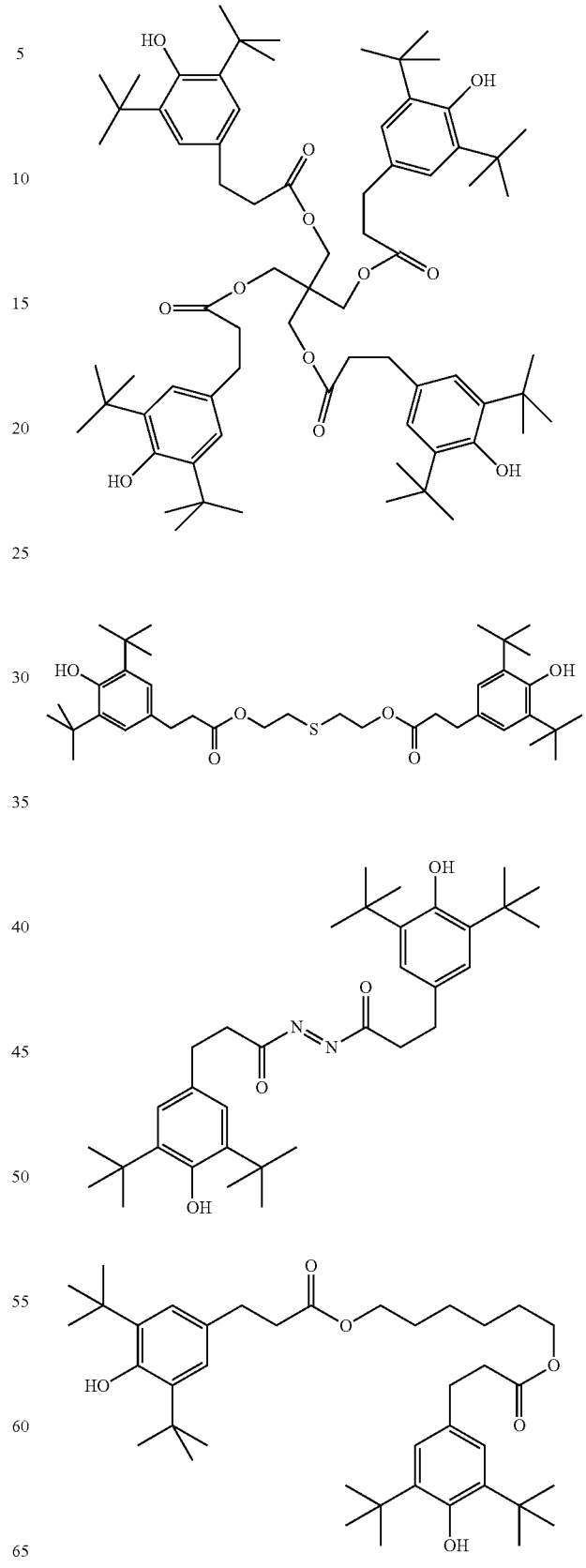

TABLE F-continued
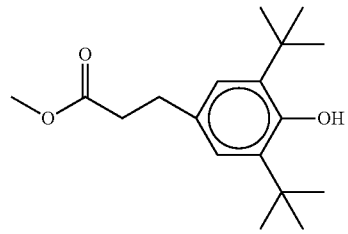
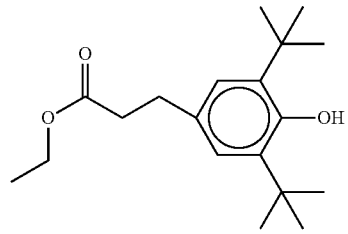
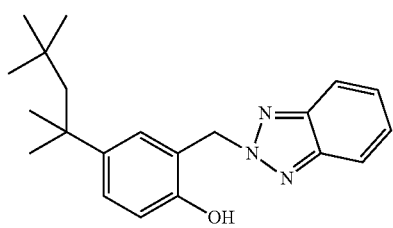 [SMILES: CC(C)(C)CC(C)(C)c1ccc(O)c(Cn2nc3ccccc3n2)c1]
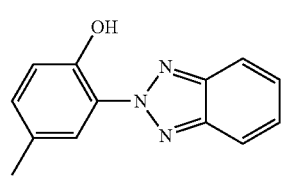 [SMILES: Cc1ccc(O)c(-n2nc3ccccc3n2)c1]
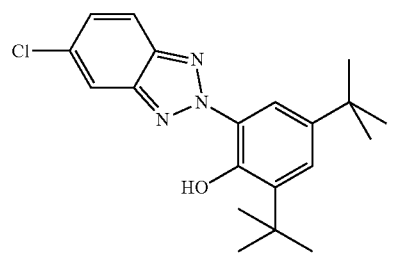 [SMILES: CC(C)(C)c1cc(-n2nc3ccc(Cl)cc3n2)c(O)c(C(C)(C)C)c1]
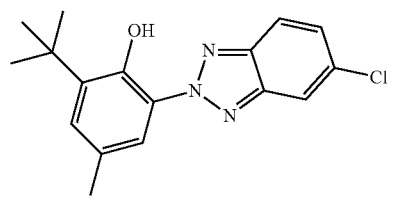 [SMILES: Cc1cc(-n2nc3ccc(Cl)cc3n2)c(O)c(C(C)(C)C)c1]
TABLE F-continued
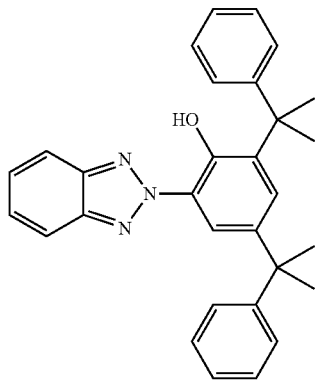 [SMILES: CC(C)(c1ccccc1)c1cc(-n2nc3ccccc3n2)c(O)c(C(C)(C)c2ccccc2)c1]
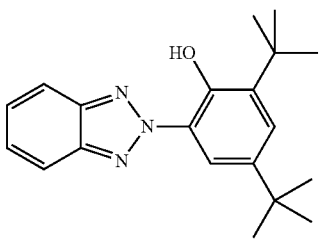 [SMILES: CC(C)(C)c1cc(-n2nc3ccccc3n2)c(O)c(C(C)(C)C)c1]
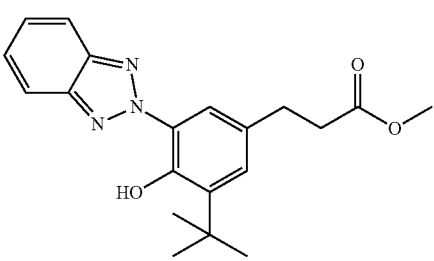 [SMILES: COC(=O)CCc1cc(-n2nc3ccccc3n2)c(O)c(C(C)(C)C)c1]
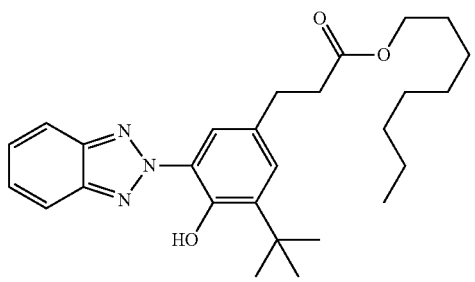 [SMILES: CCCCCCCCOC(=O)CCc1cc(-n2nc3ccccc3n2)c(O)c(C(C)(C)C)c1]

TABLE F-continued

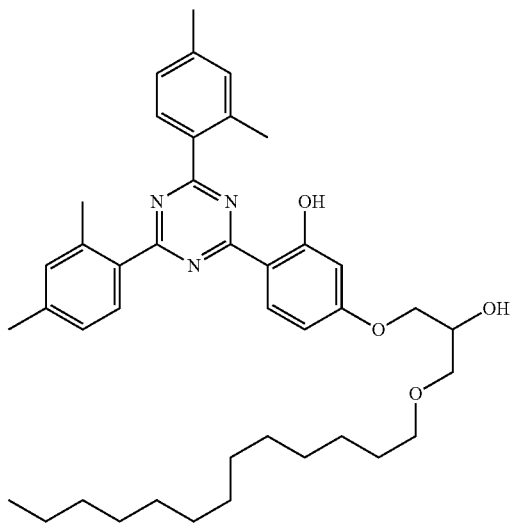 [SMILES: CCCCCCCCCCCCCOCC(O)COc1ccc(-c2nc(-c3ccc(C)cc3C)nc(-c3ccc(C)cc3C)n2)c(O)c1]

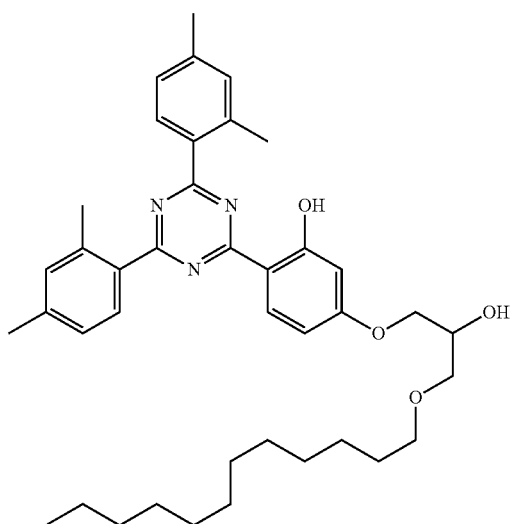 [SMILES: CCCCCCCCCCCCOCC(O)COc1ccc(-c2nc(-c3ccc(C)cc3C)nc(-c3ccc(C)cc3C)n2)c(O)c1]

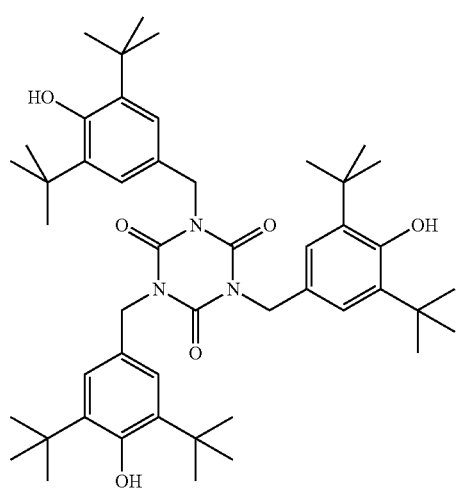 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]

TABLE F-continued

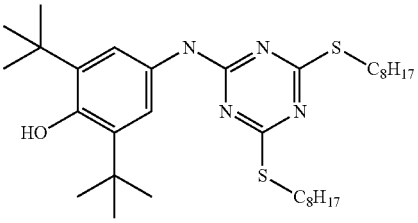

In a preferred embodiment of the present invention, the media according to the invention comprise one or more compounds selected from the group of the compounds from Table F, in particular one or more compounds selected from the group of the compounds of the following two formulae:

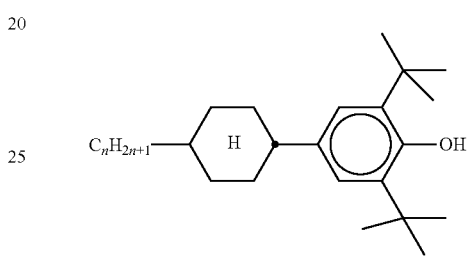

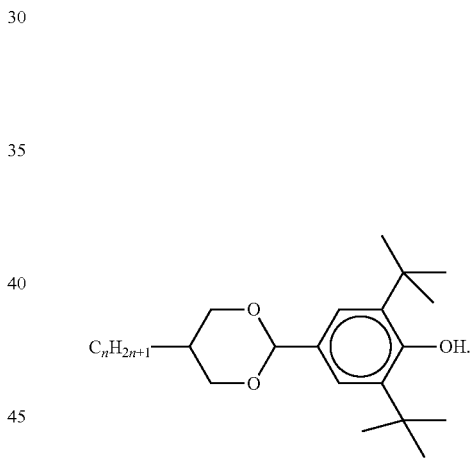

EXAMPLES

The following examples explain the present invention without restricting it in any way. However, the physical properties make it clear to the person skilled in the art what properties can be achieved and in what ranges they can be modified. In particular, the combination of the various properties which can preferably be achieved is thus well defined for the person skilled in the art.

Substance Examples

The following substances are preferred substances of the formula I in accordance with the present application or substances of the formula I preferably to be employed in accordance with the present application.

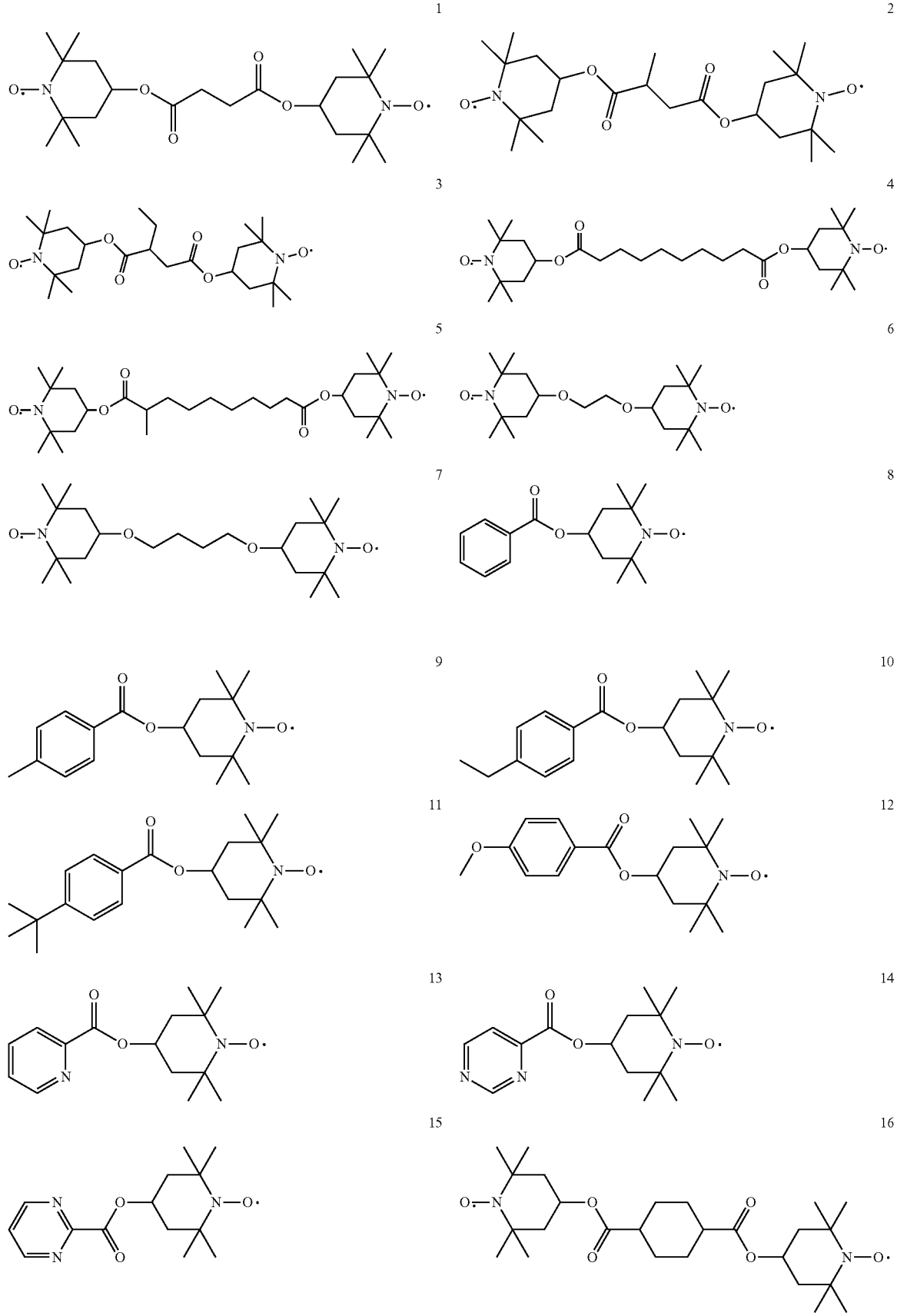

-continued
17
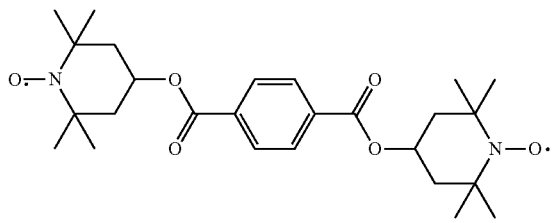
18
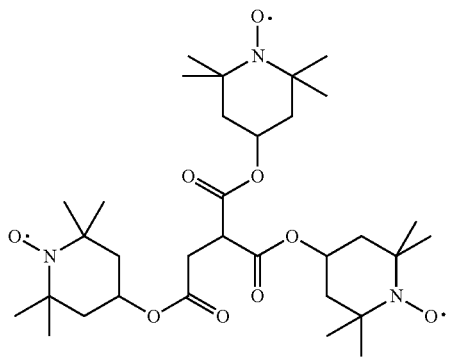
19
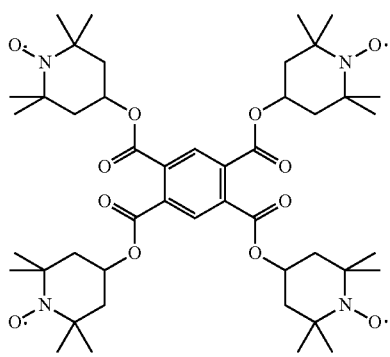
20
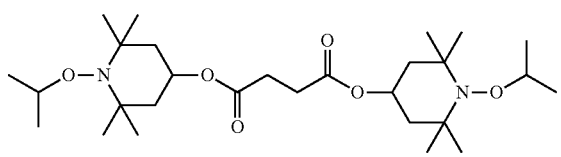
21
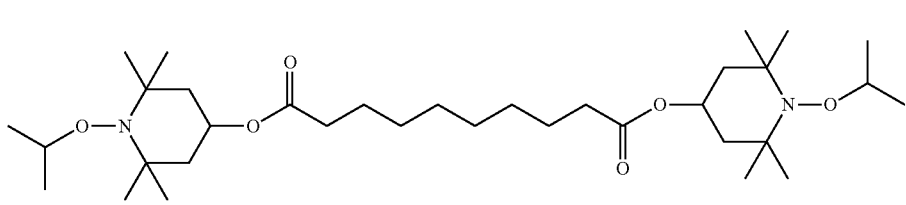
22
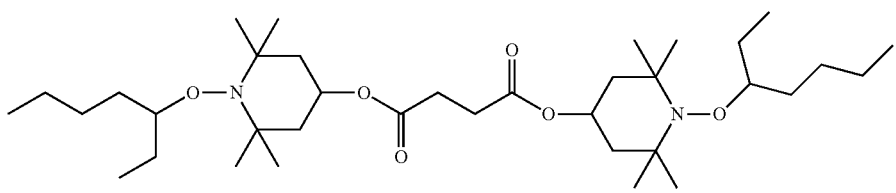
23
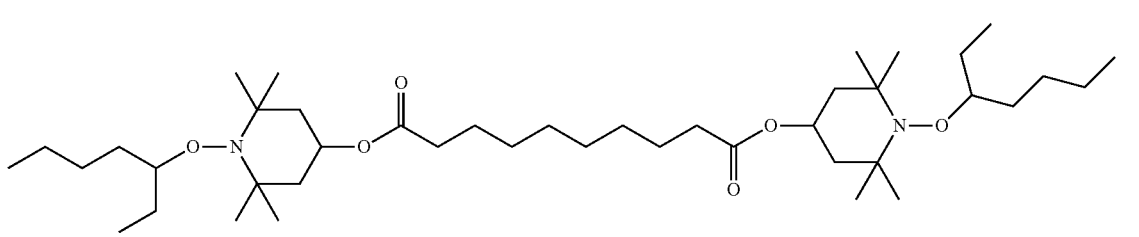
24
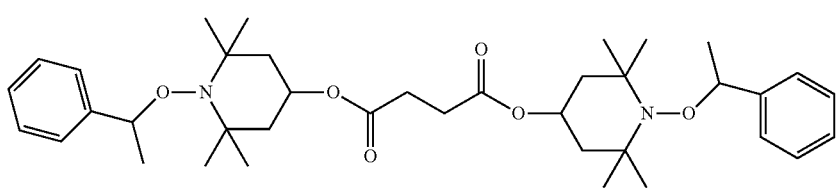

-continued
| 25 | 26 |
|---|---|
| 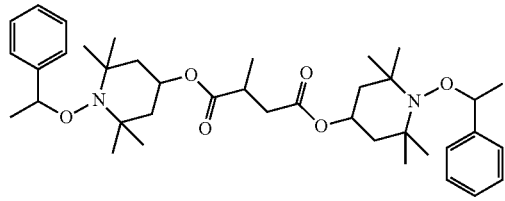 | 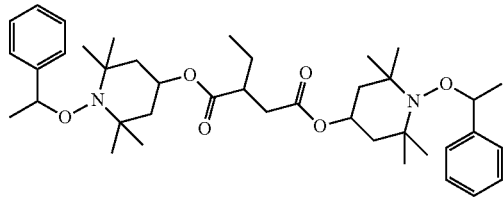 |
27
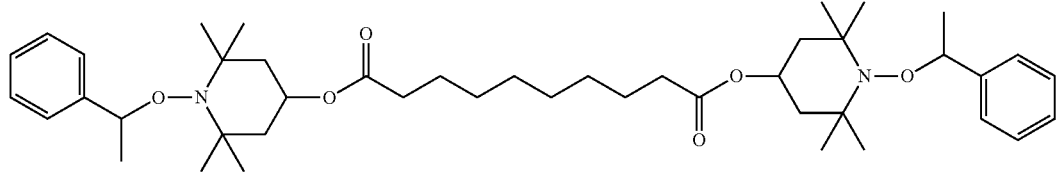
| 28 | 29 |
|---|---|
| 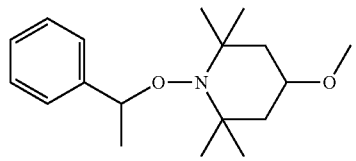 | 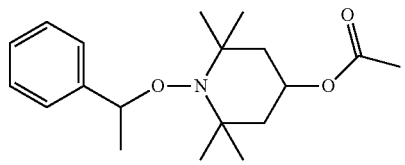 |
| 30 | 31 |
|---|---|
| 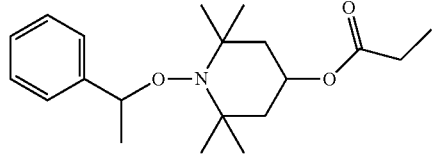 | 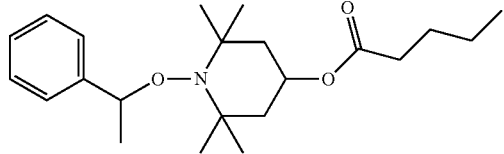 |
| 32 | 33 |
|---|---|
| 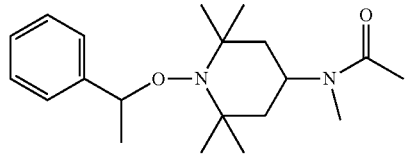 | 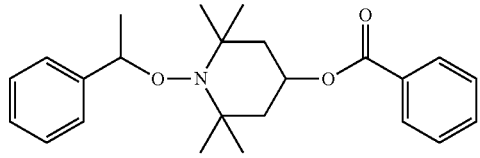 |
| 34 | 35 |
|---|---|
| 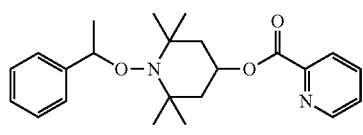 | 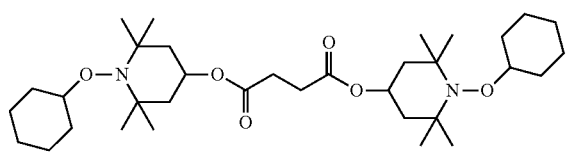 |
36
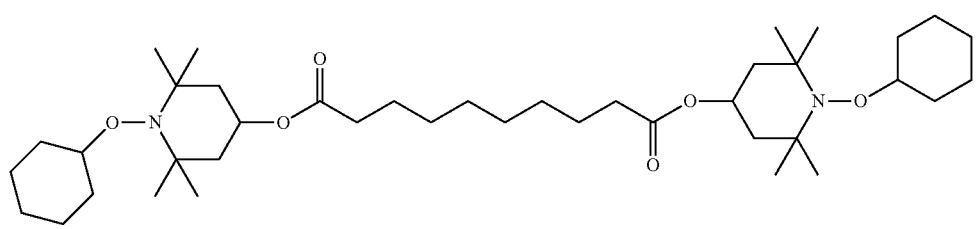
37
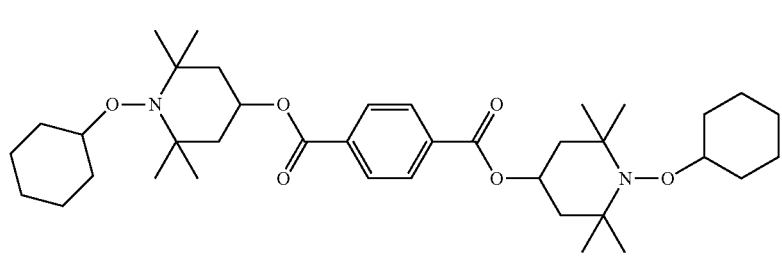

-continued
38
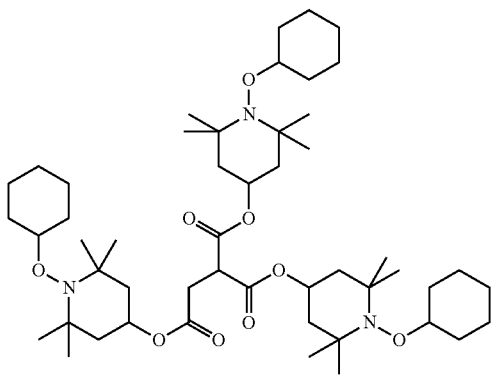
39
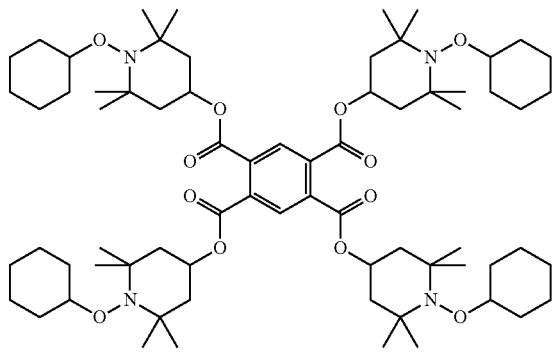
40
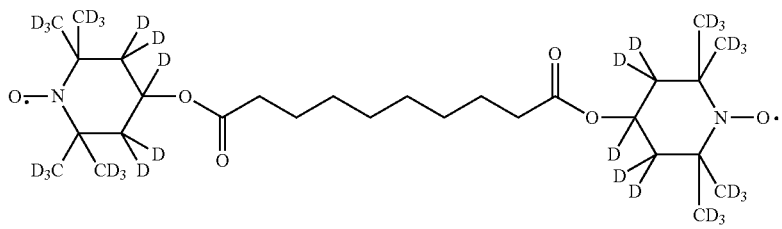
42
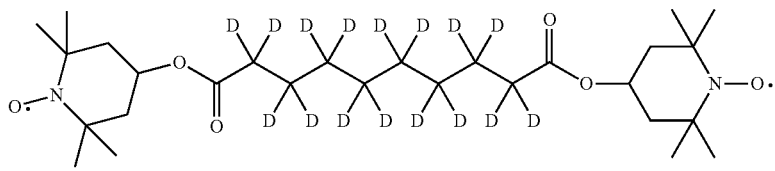
43
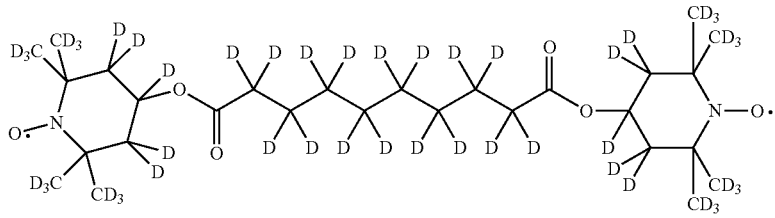
44
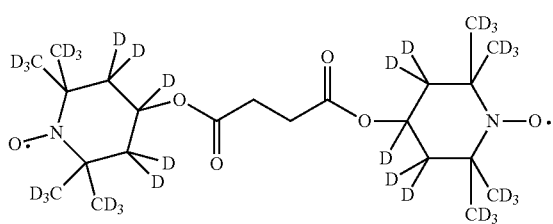
45
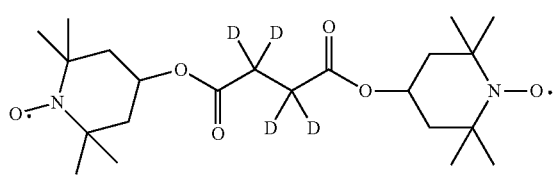
46
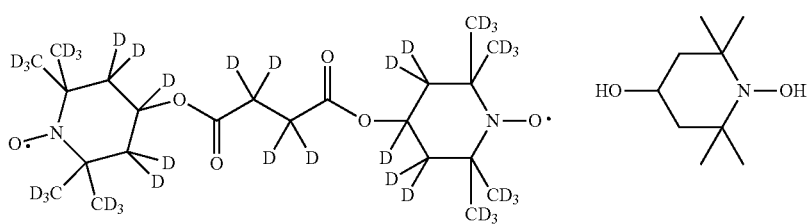
47
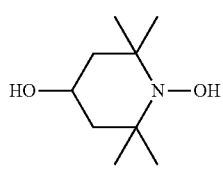

-continued

48
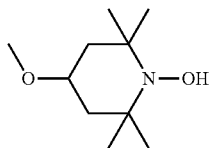

49
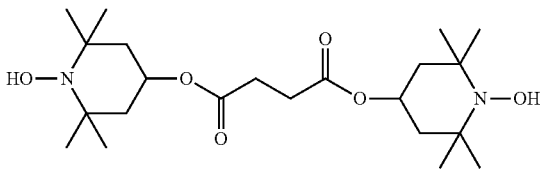

50
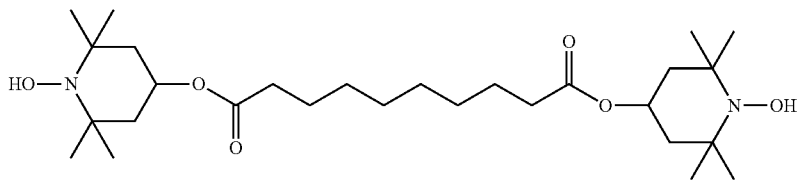

51
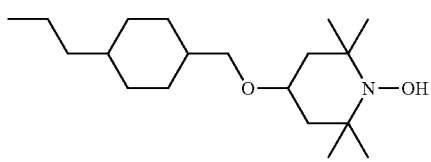

52
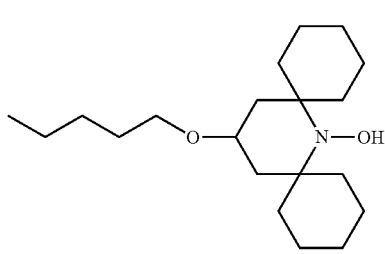

53
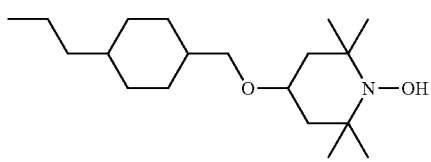

Synthesis Example 1

Synthesis of bis(2,2,6,6-tetramethyl-4-piperidyl)N,N'-dioxyl succinate (Substance Example 1)

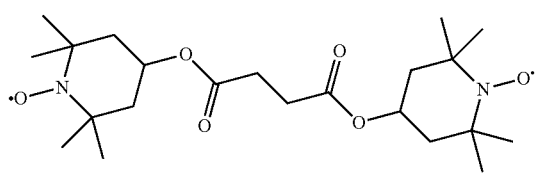

2.15 g (12.26 mmol) of 4-hydroxy-2,2,6,6-tetramethylpiperidin-1-oxyl, 40 mg (0.33 mmol) of 4-(dimethylamino)pyridine and 1 ml (12.4 mmol) of dried pyridine are initially introduced in 20 ml of dry dichloromethane. 4 Ångström activated molecular sieve is subsequently added, and the mixture is stirred at room temperature (RT for short; about 22° C.) for 90 min. The reaction solution is cooled to a temperature in the range from 7 to 10° C., and 0.71 ml (6.13 mmol) of succinyl dichloride is slowly added, and the mixture is stirred at RT for 18 h. Sufficient sat. NaHCO$_3$ solution and dichloromethane are added to the reaction solution, and the organic phase is separated off, washed with water and sat. NaCl solution, dried over Na$_2$SO$_4$, filtered and evaporated. The crude product is purified over silica gel with dichloromethane/methyl tert-butyl ether (95:5), giving the product as a white solid having a purity of >99.5%.

Synthesis Example 2

Synthesis of bis(2,2,6,6-tetramethylpiperidin-1-oxyl-4-yl)decanedioate (Substance Example 4)

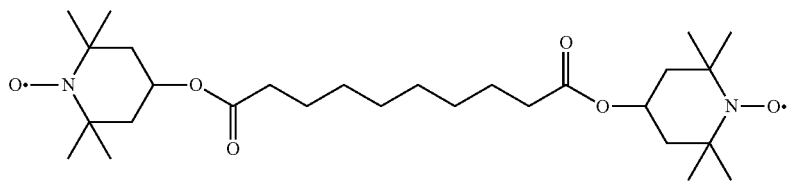

28.5 g (166 mmol) of 4-hydroxy-2,2,6,6-tetramethylpiperidin-1-oxyl (free radical) and 250 mg (2.05 mmol) of 4-(dimethylamino)pyridine are dissolved in 300 ml of degassed dichloromethane, and 50.0 ml (361 mmol) of triethylamine are added. The mixture is subsequently degassed and cooled to 0° C., and 10 g (41.4 mmol) of sebacoyl chloride dissolved in 100 ml of degassed dichloromethane are added dropwise at 0-5° C., and the mixture is stirred at room temperature for 18 h. When the reaction is complete, water and HCl (pH=4-5) are added with ice-cooling, and the mixture is stirred for a further 30 min. The organic phase is separated off, and the water phase is subsequently extracted with dichloromethane, and the combined phases are washed with saturated NaCl solution and dried over $Na_2SO_4$, filtered and evaporated, giving 24.4 g of a red liquid, which together are passed through 100 g of basic $Al_2O_3$ and 500 g of silica gel on a frit with dichloromethane/methyl tert-butyl ether (95/5), giving orange crystals, which are dissolved in degassed acetonitrile at 50° C. and crystallized at −25° C., giving the product as orange crystals having an HPLC purity of 99.9%.

Synthesis Example 3

Synthesis of bis(2,2,6,6-tetramethyl-4-piperidyl)N,N'-dioxylbutanediol (Substance Example 7)

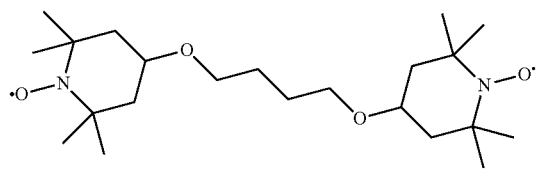

Sufficient pentane is added to 15.0 g (60% in mineral oil, 375 mmol) of NaH under a protective gas, and the mixture is allowed to settle. The pentane supernatant is pipetted off and carefully quenched with isopropanol with cooling. 100 ml of THF are then carefully added to the washed NaH. The reaction mixture is heated to 55° C., and a solution of 50.0 g (284 mmol) of 4-hydroxy-2,2,6,6-tetramethylpiperidin-1-oxyl in 400 ml of THF is carefully added dropwise. The hydrogen formed is discharged directly. When the addition of the solution is complete, stirring is continued at 60° C. overnight (16 h). The reaction mixture is subsequently cooled to 5° C., and 1,4-butanediol dimethylsulfonate is added in portions. The mixture is subsequently slowly heated to 60° C. and stirred at this temperature for 16 h. When the reaction is complete, the mixture is cooled to RT, and 200 ml of 6% ammonia solution in water are added with cooling, and the mixture is stirred for 1 h. The organic phase is subsequently separated off, the aqueous phase is rinsed with methyl tert-butyl ether, the combined organic phases are washed with sat. NaCl solution, dried and evaporated. The crude product is purified over silica gel with dichloromethane/methyl tert-butyl ether (8:2) and crystallized from acetonitrile at −20° C., giving the product as a pink crystalline solid having a purity of >99.5%.

Synthesis Example 4

Synthesis of bis[2,2,6,6-tetramethyl-1-(1-phenylethoxy)piperidin-4-yl]succinate (Substance Example 24)

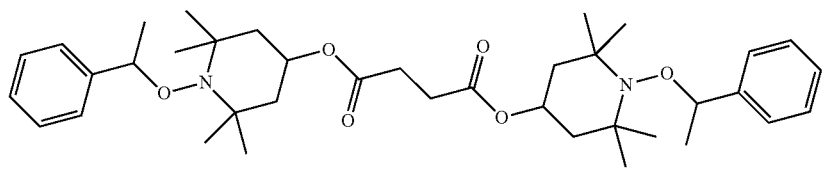 [SMILES: CC(ON1C(C)(C)CC(OC(=O)CCC(=O)OC2CC(C)(C)N(OC(C)c3ccccc3)C(C)(C)C2)CC1(C)C)c1ccccc1]

Step 4.1: Synthesis of 2,2,6,6-tetramethyl-1-(1-phenylethoxy)piperidin-4-ol

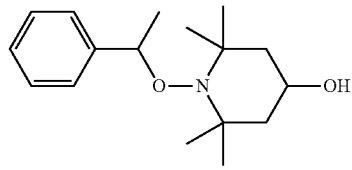 [SMILES: CC(ON1C(C)(C)CC(O)CC1(C)C)c1ccccc1]

5.0 g (29.03 mmol) of 4-hydroxy-2,2,6,6-tetramethylpiperidin-1-oxyl, 7.80 g (58.1 mmol) of 2-phenylpropionaldehyde and 100.6 mg (1.02 mmol) of copper(I) chloride are initially introduced in 20 ml of tert-butanol. 6.45 ml (58.06 mmol) of 35% hydrogen peroxide solution are then carefully and slowly added dropwise at such a rate that the internal temperature does not exceed 30° C. The mixture is therefore cooled by means of ice-cooling during the dropwise addition. Oxygen is formed in the reaction and would spontaneously be released in large quantities if the addition were too fast and the temperature too high. When the addition is complete, the reaction solution is stirred at RT for a further 16 h, and sufficient water/methyl tert-butyl ether is subsequently added, and the organic phase is separated off. The organic phase is washed with 10% ascorbic acid until peroxide-free, and the peroxide content is checked. The mixture is subsequently washed with 10% NaOH solution, water and sat. NaCl solution, dried over $Na_2SO_4$, filtered and evaporated. The crude product obtained is purified over silica gel with heptane/methyl tert-butyl ether (1:1), giving the product as colorless crystals.

Step 4.2: Synthesis of bis[2,2,6,6-tetramethyl-1-(1-phenylethoxy)piperidin-4-yl]succinate 1.52 g (5.5 mmol) of the product from the preceding step, the compound 2,2,6,6-tetramethyl-1-(1-phenylethoxy)piperidin-4-ol, 15.3 mg (0.125 mmol) of dimethylaminopyridine and 1.02 ml (12.6 mmol) of dried pyridine are initially introduced in 10 ml of dichloromethane and cooled to a temperature in the range from 7 to 10° C. 0.255 ml (2.199 mmol) of succinoyl dichloride is then added dropwise as such and if necessary topped up if hydroxyl compound is still present. When the reaction is complete, the reaction mixture is filtered directly through silica gel with dichloromethane and subsequently eluted with heptane/methyl tert-butyl ether (1:1) and pure methyl tert-butyl ether. The product obtained is dissolved in acetonitrile and purified by means of preparative HPLC (2 Chromolith columns with 50 ml/min of acetonitrile), giving the product as a yellow oil having a purity of >99.9%.

Synthesis Example 5

Synthesis of 2,2,6,6-tetramethyl-1-(1-phenylethoxy)piperidin-4-yl pentanoate (Substance Example 31)

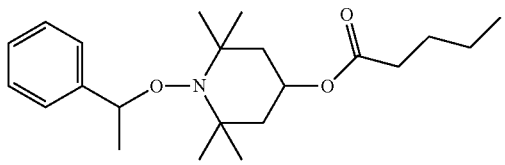 [SMILES: CCCCC(=O)OC1CC(C)(C)N(OC(C)c2ccccc2)C(C)(C)C1]

2.5 g (9.01 mmol) of the compound 2,2,6,6-tetramethyl-1-(1-phenylethoxy)piperidin-4-ol from step 3.1 and 55.1 mg (0.45 mmol) of (4-dimethylaminopyridine) are dissolved in 50.0 ml of dry dichloromethane and cooled to 3° C. 5.47 ml (27.03 mmol) of valeric anhydride are added at this temperature, and the mixture is stirred at room temperature for 14 h. When the reaction is complete, the mixture is carefully poured into icewater, adjusted to pH 6 using 2N HCl, and the organic phase is separated off. The aqueous phase is extracted with dichloromethane, and the combined organic phases are washed with saturated NaCl solution, a mixture of water and triethylamine (300:50 ml) and dried over MgSO₄, filtered and evaporated. Purification on silica gel with heptane/methyl tert-butyl ether (9:1) gives the product as a colorless oil.

Synthesis Example 6

Synthesis of 1,4-bis(1-hydroxy-2,2,6,6-tetramethyl-4-piperidinyl)butanedioate (Substance Example 49)

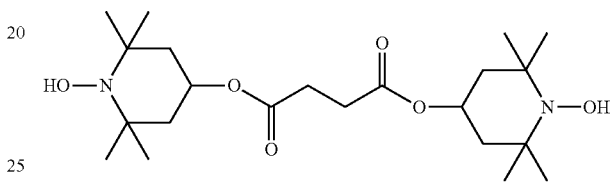

40 ml of water and 80 ml of dioxane are mixed and carefully degassed by means of a stream of argon. 2.0 g (4.7 mmol) of the free radical from Substance Example 1 (Synthesis Example 1) are dissolved in the solvent mixture, and 4.95 g (28.1 mmol) of ascorbic acid are added in portions. The reaction mixture becomes colorless during this addition and is stirred at 40° C. for 18 h under a protective-gas atmosphere. The mixture is cooled to room temperature, and 100 ml of water are added, the mixture is stirred briefly, and the crystals formed are filtered off with suction. The crystals are dissolved in 50 ml of hot degassed THF, and the insoluble constituents are filtered off, and the filtrate is crystallized at −25° C. The pale-pink crystals are then washed by stirring in acetonitrile at room temperature for 18 h, giving the product as pale-pink crystals having an HPLC purity of 100%.

Synthesis Example 8

Synthesis of 1,10-bis(1-hydroxy-2,2,6,6-tetramethyl-4-piperidinyl)decanedioate (Substance Example 50)

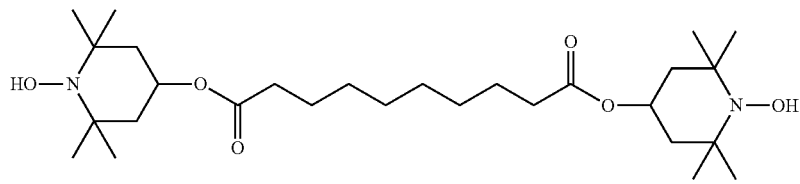 [SMILES: CC1(C)CC(OC(=O)CCCCCCCCC(=O)OC2CC(C)(C)N(O)C(C)(C)C2)CC(C)(C)N1O]

All solvents used are thoroughly degassed in advance by means of a stream of argon. During work-up, brown glass equipment must be used. 1.70 g (3.32 mmol) of the free radical from Substance Example 4 (Synthesis Example 2) are dissolved in 60 ml of dioxane. 3.6 g (20 mmol) of ascorbic acid dissolved in 30 ml of water are subsequently added dropwise to the solution at room temperature. The reaction solution starts to become colorless during this dropwise addition, and the reaction is complete after stirring at room temperature for 1 h. The mixture is extracted with 100 ml of dichloromethane, and the organic phase is washed with water, dried over $Na_2SO_4$, filtered and evaporated. The yellow crystals formed are dried at 160° C. and $10^{-2}$ mbar for 5 min, giving a viscous, slowly crystallizing oil.

Liquid-crystal mixtures having the compositions and properties as indicated in the following tables are prepared and investigated.

Examples 1.1 and 1.2 (B1.1 and B1.2) and Comparative Examples 1.0 and 1.1 (C1.0 and C1.1)

The following mixture (M-1), which comprises in total slightly more than 40% of compounds containing an alkenyl end group and 8% of a compound containing a cyclohexenylene unit, is prepared and investigated.

| Mixture M-1 | | |
|---|---|---|
| Composition | | |
| | Compound | Concentration |
| No. | Abbreviation | /% by weight |
| 1 | CY-3-O2 | 15.0 |
| 2 | CY-5-O2 | 6.0 |
| 3 | CCY-3-O2 | 3.0 |
| 4 | CLY-3-O2 | 8.0 |
| 5 | CPY-2-O2 | 8.0 |
| 6 | CPY-3-O2 | 8.0 |
| 7 | PYP-2-3 | 11.5 |
| 8 | CC-3-V | 35.0 |
| 9 | CCP-V-1 | 5.5 |
| Σ | | 100.0 |
| Physical properties | | |
| T(N, I) = | | 75.4 °C. |
| $n_e$(20° C., 589 nm) = | | 1.5933 |
| Δn(20° C., 589 nm) = | | 0.1077 |
| $\epsilon\perp$(20°, 1 kHz) = | | 6.5 |
| Δε(20°, 1 kHz) = | | −3.0 |
| $\gamma_1$(20° C.) = | | 93 mPa·s |
| $k_{11}$(20° C.) = | | 12.9 pN |
| $k_{33}$(20° C.) = | | 14.8 pN |
| $V_0$(20° C.) = | | 2.35 V |

Mixture M-1 is divided into four parts and investigated as described below.

Comparative Examples 1.0 and 1.1

Firstly, the stability of the voltage holding ratio of mixture (M-1) itself and of a further sample of this mixture to which 250 ppm of the compound TINUVIN®770 have been added is determined. The resultant mixture (CM-1-1) is, like mixture M-1 itself, investigated for its stability to illumination by means of cold-cathode (CCFL)-LCD backlighting in a test cell having an alignment material for homeotropic alignment and flat ITO electrodes. To this end, corresponding test cells are exposed to the lighting for 750 hours. The voltage holding ratio is then determined in each case after 5 minutes at a temperature of 100° C. The results are summarized below in Table 1. Here, as below, six test cells are filled and investigated for each individual mixture. The values indicated are the average of the six individual values and the standard deviation (σ) thereof, including for the case where the standard deviation is smaller than the measurement value accuracy indicated above.

Examples 1.1 and 1.2

Next, 63 ppm or alternatively 250 ppm of the compound from Synthesis Example 1

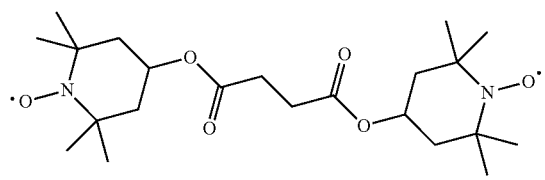

are added to mixture M-1, and the resultant mixtures (M-1-1 and M-1-2 respectively) are investigated for their stability, as described above. The results are shown in the following table, Table 1.

The relative deviations of the voltage holding ratio values in different measurement series are typically in the range from about 3 to 4%.

The drop in the voltage holding ratio (ΔVHR) usually caused by the exposure is determined as described in the text above. Thus, a relative stabilization of $S_{rel}$(750 h)=1.9 is obtained for Example 1.1 compared with the reference mixture (Comparative Example 1.0).

TABLE 1

| | | | | | VHR(t)/% | | $S_{rel}$(t) |
|---|---|---|---|---|---|---|---|
| Ex. | No. | Mixture | Stabi-lizer | c(stab.)/ ppm | t = 0 h | t = 750 h | t = 750 h |
| C1.0 | 1 | M-1 | none | 0 | 95.4 ± 0.3 | 63 ± 0.9 | 1 |
| C1.1 | 2 | CM-1-1 | T770 | 250 | 95.3 ± 0.4 | 71 ± 1.8 | 1.3 |
| B1.1 | 3 | M-1-1 | I* | 63 | 93.7 ± 0.5 | 77 ± 1.2 | 1.9 |
| B1.2 | 4 | M-1-2 | I* | 250 | 93.0 ± 0.7 | 72 ± 1.1 | 1.5 |

Notes:
I*: compound from Synthesis Example 1
T770: TINUVIN ®770

In addition, the ion densities of the four mixtures are determined. The results are summarized in the following table (Table 2).

TABLE 2

| Ex. | No. | Mixture | Stabilizer | c(stab.)/ ppm | Ion density/ pC | $S_{rel}$(t) t = 750 h |
|---|---|---|---|---|---|---|
| C1.0 | 1 | M-2 | none | 0 | 159 ± 21 | 1 |
| C1.1 | 2 | CM-1-1 | T770 | 250 | 851 ± 89 | 1.3 |
| B1.1 | 3 | M-1-1 | I* | 50 | 179 ± 17 | 1.9 |
| B1.2 | 4 | M-1-2 | I* | 250 | 234 ± 26 | 1.5 |

Notes:
I*: compound from Synthesis Example 1
T770: TINUVIN ®770

It is readily evident here that the compound from Synthesis Example 1, even in relatively low concentrations, clearly exhibits stabilizing properties which are clearly superior both to those of the starting mixture and also to those of the comparative mixture. In addition, the ion density is virtually unchanged compared with the undoped reference. TINUVIN®770, by contrast, exhibits an ion density which is four times as high, which suggests a stronger ionic interaction with the polyimide. TINUVIN®770 thus exhibits a significantly stronger interaction with the alignment material. The behavior for the compound from Synthesis Example 1 looks significantly more favorable.

The compound from Synthesis Example 1 in a concentration of 63 ppm has a stabilization activity which is superior to all other stabilizers investigated here. This results in a reduction in the risk of image sticking during exposure to the backlighting.

Examples 2.1 and 2.2 and Comparative Examples 2.0 and 2.1

The following mixture (M-2), which comprises 37% of compounds containing an alkenyl end group, is prepared and investigated.

| Mixture M-2 | | |
|---|---|---|
| Composition | | |
| Compound | | Concentration |
| No. | Abbreviation | /% by weight |
| 1 | CY-3-O2 | 15.0 |
| 2 | CY-3-O4 | 3.0 |
| 3 | CCY-3-O2 | 6.0 |
| 4 | CCY-3-O3 | 3.5 |
| 5 | CCY-4-O2 | 5.0 |
| 6 | CPY-2-O2 | 8.0 |
| 7 | CPY-3-O2 | 8.0 |
| 8 | PYP-2-3 | 8.0 |
| 9 | PYP-2-4 | 6.5 |
| 10 | CC-3-V | 37.0 |
| Σ | | 100.0 |
| Physical properties | | |
| T(N, I) = | | 74 °C. |
| $n_e$(20° C., 589 nm) = | | 1.5927 |
| Δn(20° C., 589 nm) = | | 0.1072 |
| $\epsilon_\perp$(20°, 1 kHz) = | | 6.6 |
| Δε(20°, 1 kHz) = | | −3.0 |
| $\gamma_1$(20° C.) = | | t.b.d. mPa · s |
| $k_{11}$(20° C.) = | | 12.4 pN |
| $k_{33}$(20° C.) = | | 13.9 pN |
| $V_0$(20° C.) = | | 2.27 V |

Note:
t.b.d.: to be determined

Mixture M-2 is, as described in Example 1, divided into four parts, and, as described therein, two different concentrations of the compound from Synthesis Example 1 or TINUVIN®770 are alternatively added, and the corresponding mixtures are investigated for their stability to illumination by means of LCD backlighting in test cells. For the mixtures which comprise the compound from Synthesis Example 1, comparably favorable results as in Example 1 are also achieved here.

Examples 3.1 and 3.2 (B3.1 and B3.2) and Comparative Examples 3.0 and 3.1 (C3.0 and C3.1)

The following mixture (M-3), which comprises 40% of compounds containing an alkenyl end group, is prepared and investigated.

| Mixture M-3 | | |
|---|---|---|
| Composition | | |
| Compound | | Concentration |
| No. | Abbreviation | /% by weight |
| 1 | CY-3-O2 | 10.0 |
| 2 | PY-3-O2 | 10.0 |
| 3 | CCY-3-O2 | 11.0 |
| 4 | CPY-2-O2 | 8.5 |
| 5 | CPY-3-O2 | 10.5 |
| 6 | PYP-2-3 | 7.0 |
| 7 | CC-3-V | 33.5 |
| 8 | CC-3-V1 | 6.5 |
| 9 | CCP-3-1 | 3.0 |
| Σ | | 100.0 |
| Physical properties | | |
| T(N, I) = | | 74.9 °C. |
| $n_e$(20° C., 589 nm) = | | 1.5931 |
| Δn(20° C., 589 nm) = | | 0.1081 |
| $\epsilon_\perp$(20°, 1 kHz) = | | 6.5 |
| Δε(20°, 1 kHz) = | | −3.0 |
| $\gamma_1$(20° C.) = | | t.b.d. mPa · s |
| $k_{11}$(20° C.) = | | 13.0 pN |
| $k_{33}$(20° C.) = | | 15.9 pN |
| $V_0$(20° C.) = | | 2.43 V |

Note:
t.b.d.: to be determined

Mixture M-3 is, as described in Example 1, divided into four parts, and, as described therein, two different concentrations of the compound from Synthesis Example 1 or TINUVIN®770 are alternatively added, and the corresponding mixtures are investigated in test cells for their stability to illumination by means of LCD backlighting. For the mixtures which comprise the compound from Synthesis Example 1, comparably favorable results as in Example 1 are also achieved here. These are summarized in the following two tables.

TABLE 3

| Ex. | No. | Mixture | Stabilizer | c(stab.)/ ppm | VHR(t)/% t = 0 h | VHR(t)/% t = 1000 h | $S_{rel}$(t) t = 1000 h |
|---|---|---|---|---|---|---|---|
| C3.0 | 1 | M-3 | none | 0 | 98.0 ± 0.3 | 68 ± 2 | 1 |
| C3.1 | 2 | CM-3-1 | T770 | 250 | 96.6 ± 0.4 | 79 ± 2 | 1.7 |
| B3.1 | 3 | M-3-1 | I* | 25 | 97.3 ± 0.2 | 77 ± 1 | 1.5 |
| B3.2 | 4 | M-3-2 | I* | 50 | t.b.d. | t.b.d. | t.b.d. |

Notes:
I*: compound from Synthesis Example 1
T770: TINUVIN ®770
t.b.d.: to be determined

TABLE 4

| Ex. | No. | Mixture | Stabilizer | c(stab.)/ ppm | Ion density/ pC | $S_{rel}$(t) t = 1000 h |
|---|---|---|---|---|---|---|
| C3.0 | 1 | M-3 | none | 0 | 181 ± 25 | 1.0 |
| C3.1 | 2 | CM-3-1 | T770 | 250 | 1.031 ± 58 | 1.7 |
| B3.1 | 3 | M-3-1 | I* | 25 | 224 ± 29 | 1.5 |
| B3.2 | 4 | M-3-2 | I* | 50 | t.b.d. | t.b.d. |

Notes:
I*: compound from Synthesis Example 1
T770: TINUVIN ®770
t.b.d.: to be determined Examples 4.1 to 4.3 (B4.1-B4.3) and Comparative Examples 4.0 and 4.1 (C4.0-C4.1)

The following mixture (M-4), which comprises in total slightly more than 38% of compounds containing an alkenyl end group, is prepared and investigated.

| Mixture M-4 | |
| --- | --- |
| Composition | |
| Compound | Concentration |
| No. | Abbreviation | /% by weight |
| --- | --- | --- |
| 1 | CY-3-O2 | 15.0 |
| 2 | CY-5-O2 | 6.5 |
| 3 | CCY-3-O2 | 11.0 |
| 4 | CPY-2-O2 | 5.5 |
| 5 | CPY-3-O2 | 10.5 |
| 6 | PYP-2-3 | 12.5 |
| 7 | CC-3-V | 28.5 |
| 8 | CC-3-V1 | 10.0 |
| 9 | PPGU-3-F | 0.5 |
| Σ | | 100.0 |
| Physical properties | | |
| T(N, I) = | | 74.7 °C. |
| $n_e$(20° C., 589 nm) = | | 1.5923 |
| Δn(20° C., 589 nm) = | | 0.1082 |
| $\epsilon_\perp$(20°, 1 kHz) = | | 6.6 |
| Δε(20°, 1 kHz) = | | −3.0 |
| $\gamma_1$(20° C.) = | | 97 mPa · s |
| $k_{11}$(20° C.) = | | t.b.d. pN |
| $k_{33}$(20° C.) = | | t.b.d. pN |
| $V_0$(20° C.) = | | t.b.d. V |

Note:
t.b.d.: to be determined

Mixture M-4 is divided into a plurality of parts and investigated as described below.

Next, 250 ppm of TINUVIN®770 or in each case alternatively 50 ppm of the compound from Substance Example 47

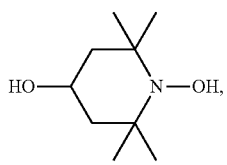

50 ppm of the compound from Substance Example 48

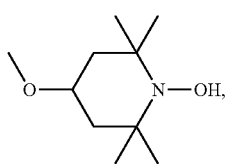

250 ppm of the compound from Substance Example 49 (Synthesis Example 6)

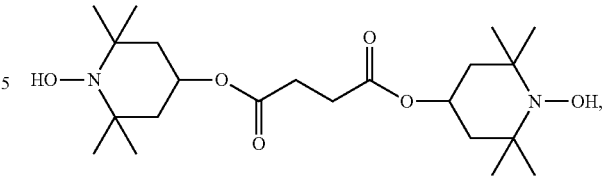

are added to the various parts of mixture M-4, and the resultant mixtures (CM-4.1 and M-4-1 to M-4-3) are investigated for their stability, as described above. The results are shown in the following two tables.

TABLE 5

| | | | Stabi- | c(stab.)/ | VHR(t)/% | | $S_{rel}$(t) |
| --- | --- | --- | --- | --- | --- | --- | --- |
| Ex. | No. | Mixture | lizer | ppm | t = 0 h | t = 1.000 h | t = 1.000 h |
| C4.0 | 1 | M-4 | none | 0 | 98.6 ± 0.3 | 73.6 ± 0.4 | 1.0 |
| C4.1 | 2 | CM-4-1 | T770 | 250 | 97.3 ± 0.1 | 87.4 ± 0.5 | 2.5 |
| B4.1 | 3 | M-4-1 | 47* | 50 | 97.4 ± 0.3 | 87.0 ± 0.9 | 2.4 |
| B4.2 | 4 | M-4-2 | 48* | 50 | 97.7 ± 0.3 | 84.3 ± 2.0 | 2.0 |
| B4.3 | 5 | M-4-2 | 49* | 250 | 98.6 ± 0.2 | 80.8 ± 2.0 | 1.4 |

Notes:
47*: compound from Substance Example 47
48*: compound from Substance Example 48
49*: compound from Substance Example 49
T770: TINUVIN ®770
t.b.d.: to be determined On exposure to a CCFL backlight, it is found that, for example, the compound from Substance Example 47 has virtually the same stabilizing action as TINUVIN®770.

TABLE 6

| Ex. | No. | Mixture | Stabilizer | c(stab.)/ ppm | Ion density/ pC | $S_{rel}$(t) t = 1000 h |
| --- | --- | --- | --- | --- | --- | --- |
| C4.0 | 1 | M-4 | none | 0 | 87 ± 7 | 1.0 |
| C4.1 | 2 | CM-4-1 | T770 | 250 | 851 ± 89 | 2.5 |
| B4.1 | 3 | M-4-1 | 47* | 50 | 266 ± 34 | 2.4 |
| B4.2 | 4 | M-4-2 | 48* | 50 | 228 ± 53 | 2.0 |
| B4.3 | 5 | M-4-2 | 49* | 250 | 98 ± 14 | 1.4 |

Notes:
47*: compound from Substance Example 47
48*: compound from Substance Example 48
49*: compound from Substance Example 49
T770: TINUVIN ®770
t.b.d.: to be determined All novel compounds investigated here exhibit significantly lower values of the ion density than TINUVIN®770. A significantly lower number of ions caused by the stabilizers can thus be expected.

Examples 5.1 to 5.3 (B5.1-B5.3) and Comparative Examples 5.0 and 5.1 (C5.0-05.1)

The following mixture (M-5), which comprises in total slightly more than 36% of compounds containing an alkenyl end group, is prepared and investigated.

| Mixture M-5 | | |
|---|---|---|
| Composition | | |
| Compound | | Concentration |
| No. | Abbreviation | /% by weight |
| 1 | CY-3-O2 | 9.0 |
| 2 | PY-3-O2 | 13.5 |
| 3 | CCY-3-O1 | 8.0 |
| 4 | CCY-3-O2 | 3.0 |
| 5 | CCY-4-O2 | 3.0 |
| 6 | CPY-2-O2 | 10.0 |
| 7 | CPY-3-O2 | 10.0 |
| 8 | CC-3-V | 36.5 |
| 9 | CPP-3-2 | 6.5 |
| 10 | PPGU-3-F | 0.5 |
| Σ | | 100.0 |
| Physical properties | | |
| $T(N, I)$ = | | 74.6 °C. |
| $n_e(20°$ C., 589 nm) = | | 1.5938 |
| $\Delta n(20°$ C., 589 nm) = | | 0.1082 |
| $\epsilon_\perp(20°, 1$ kHz) = | | 6.9 |
| $\Delta\epsilon(20°, 1$ kHz) = | | −3.2 |
| $\gamma_1(20°$ C.) = | | 94 mPa·s |
| $k_{11}(20°$ C.) = | | 13.0 pN |
| $k_{33}(20°$ C.) = | | 14.6 pN |
| $V_0(20°$ C.) = | | 2.29 V |

Mixture M-5 is divided into a plurality of parts and investigated as described below. Next, in each case alternatively 25 ppm, 50 ppm or 100 ppm of the compound from Substance Example 1, which is also used in Example 1, are added to the various parts of mixture M-5.

TABLE 7

| | | | Stabi- | c(stab.)/ | VHR(t)/% | | $S_{rel}(t)$ |
|---|---|---|---|---|---|---|---|
| Ex. | No. | Mixture | lizer | ppm | t = 0 h | t = 1.000 h | t = 1.000 h |
| C5.0 | 1 | M-5 | none | 0 | 94 ± 0.5 | 30 ± 2 | 1.0 |
| B5.1 | 3 | M-5-1 | I* | 25 | 94 ± 0.5 | 42 ± 2 | 1.4 |
| B5.2 | 4 | M-5-2 | I* | 50 | 94 ± 0.5 | 62 ± 2 | 2.1 |
| B5.3 | 5 | M-5-2 | I* | 100 | 94 ± 0.5 | 77 ± 1 | 2.6 |

Notes:
I*: compound from Synthesis Example 1

TABLE 8

| Ex. | No. | Mixture | Stabilizer | c(stab.)/ ppm | Ion density/ pC | $S_{rel}(t)$ t = 1.000 h |
|---|---|---|---|---|---|---|
| B5.1 | 3 | M-5-1 | I* | 25 | 169 ± 9 | 1.0 |
| B5.2 | 4 | M-5-2 | I* | 50 | t.b.d. | 1.4 |
| B5.3 | 5 | M-5-2 | I* | 100 | t.b.d. | 2.1 |
| B5.1 | 3 | M-5-1 | I* | 25 | t.b.d. | 2.6 |

Notes:
I*: compound from Synthesis Example 1
t.b.d.: to be determined

Mixture M-5 is prepared again and again divided into a plurality of parts and investigated as described below. Next, in each case alternatively 250 ppm TINUVIN®770, 50 ppm of the compound from Synthesis Example 2 (Substance Example 4)

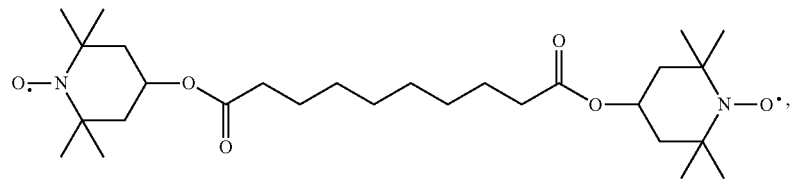

or 50 ppm or 250 ppm of the compound from Synthesis Example 8 (Substance Example 50)

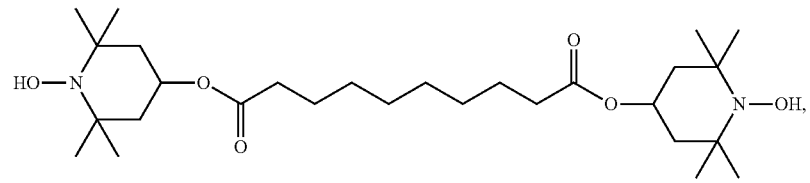 [SMILES: CC1(C)CC(OC(=O)CCCCCCCCC(=O)OC2CC(C)(C)N(O)C(C)(C)C2)CC(C)(C)N1O]

are added to the various parts of mixture M-5.

TABLE 9

| Ex. | No. | Mixture | Stabilizer | c(stab.)/ppm | VHR(t)/% t = 0 h | t = 500 h | $S_{rel}(t)$ t = 500 h |
|---|---|---|---|---|---|---|---|
| C5.1 | 2 | CM-5-1 | T770 | 250 | 94 ± 0.6 | 72 ± 2 | 1.0 |
| B5.4 | 6 | M-5-4 | II* | 50 | 95 ± 0.2 | 77 ± 2 | 1.2 |
| B5.5 | 7 | M-5-5 | VIII* | 50 | 95 ± 0.3 | 71 ± 2 | 1.5 |
| B5.6 | 8 | M-5-6 | VIII* | 250 | 94 ± 1.1 | 78 ± 2 | 1.7 |

Notes:
II*: compound from Synthesis Example 2
VIII*: compound from Synthesis Example 8
T770: TINUVIN ®770
t.b.d.: to be determined

TABLE 10

| Ex. | No. | Mixture | Stabilizer | c(stab.)/ppm | Ion density/pC | $S_{rel}(t)$ t = 500 h |
|---|---|---|---|---|---|---|
| C5.1 | 2 | CM-5-1 | T770 | V5.1 | 1,247 ± 40 | 1.0 |
| B5.4 | 6 | M-5-4 | II* | B5.4 | t.b.d. | 1.2 |
| B5.5 | 7 | M-5-5 | VIII* | B5.5 | t.b.d. | 1.5 |
| B5.6 | 8 | M-5-6 | VIII* | B5.6 | t.b.d. | 1.7 |

Notes:
II*: compound from Synthesis Example 2
VIII*: compound from Synthesis Example 8
T770: TINUVIN ®770
t.b.d.: to be determined

Examples 6.1 to 6.3 (B6.1-B6.3) and Comparative Examples 6.0 and 6.1 (C6.0-C6.1)

The following mixture (M-6), which comprises in total 35.5% of compounds containing an alkenyl end group, is prepared and investigated.

Mixture M-6

Composition

| Compound | | Concentration |
|---|---|---|
| No. | Abbreviation | /% by weight |
| 1 | CY-3-O2 | 2.0 |
| 2 | CCY-3-O1 | 5.0 |
| 3 | CCY-3-O2 | 7.0 |
| 4 | CPY-2-O2 | 9.0 |
| 5 | CPY-3-O2 | 9.0 |
| 6 | PY-3-O2 | 12.5 |
| 7 | PYP-2-3 | 10.0 |
| 8 | CC-3-V | 37.5 |
| 9 | CC-3-V1 | 8.0 |
| Σ | | 100.0 |

Physical properties

| T(N, I) = | 75 °C |
|---|---|
| Δn(20° C., 589 nm) = | 0.1112 |
| Δε(20°, 1 kHz) = | −2.6 |
| $\gamma_1$(20° C.) = | 83 mPa·s |
| $k_{11}$(20° C.) = | 13.2 pN |
| $k_{33}$(20° C.) = | 15.1 pN |
| $V_0$(20° C.) = | 2.56 V |

Notes:
t.b.d.: to be determined

Mixture M-6 is divided into a plurality of parts and in each case 250 ppm of a different compound, namely TINUVIN®770, the compound from Synthesis Example 1, the compound from Synthesis Example 2 (Substance Example 4) or the compound from Synthesis Example 8 (Substance Example 50), are added to the various parts of mixture M-6, and the respective mixtures are investigated for their stability to illumination by means of LCD backlighting in test cells.

TABLE 11

| Ex. | No. | Mixture | Stabilizer | c(stab.)/ppm | VHR(t)/% t = 0 h | t = 500 h | $S_{rel}(t)$ t = 500 h |
|---|---|---|---|---|---|---|---|
| C6.0 | 2 | M-6 | none | 0 | 75 ± 1.0 | 51 ± 1 | 1.0 |
| C6.1 | 2 | CM-6-1 | T770 | 250 | 88 ± 1.0 | 69 ± 1 | 1.5 |
| B6.1 | 6 | M-6-1 | I* | 250 | 83 ± 1.7 | 74 ± 2 | 8.5 |
| B6.2 | 7 | M-6-2 | II* | 250 | 71 ± 1.1 | 67 ± 1 | 5.1 |
| B6.3 | 8 | M-6-3 | VIII* | 250 | 71 ± 1.9 | 63 ± 1 | 2.8 |

Notes:
I*: compound from Synthesis Example 1
II*: compound from Synthesis Example 2
VIII*: compound from Synthesis Example 8
T770: TINUVIN ®770
t.b.d.: to be determined

TABLE 12

| Ex. | No. | Mixture | Stabilizer | c(stab.)/ppm | Ion density/pC | $S_{rel}(t)$ t = 500 h |
|---|---|---|---|---|---|---|
| C6.0 | 2 | M-6 | none | 0 | t.b.d. | 1.0 |
| C6.1 | 2 | CM-6-1 | T770 | 250 | t.b.d. | 1.5 |
| B6.1 | 6 | M-6-1 | I* | 250 | t.b.d. | 8.5 |
| B6.2 | 7 | M-6-2 | II* | 250 | t.b.d. | 5.1 |
| B6.3 | 8 | M-6-3 | VIII* | 250 | t.b.d. | 2.8 |

Notes:
I*: compound from Synthesis Example 1
II*: compound from Synthesis Example 2
VIII*: compound from Synthesis Example 8
T770: TINUVIN ®770
t.b.d.: to be determined The entire disclosure[s] of all applications, patents and publications, cited herein and of corresponding German Application Nos. 10 2011 018 629.8, filed Apr. 21, 2011, and 10 2011 103 024.0, filed Jun. 1, 2011, are incorporated by reference herein.

The preceding examples can be repeated with similar success by substituting the generically or specifically described reactants and/or operating conditions of this invention for those used in the preceding examples.

The invention claimed is:
1. A liquid-crystalline medium comprising:
a) one or more compounds of formula I

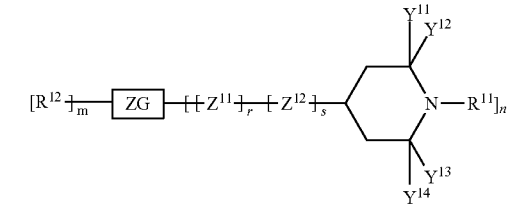

in which
n denotes 2,
m denotes (4−n),

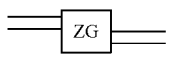

denotes an organic radical having 4 bonding sites, $Z^{11}$ and $Z^{12}$, independently of one another, denote —O—, —(C=O)—, —(N—$R^{14}$)— or a single bond, but do not both simultaneously denote —O—, r and s, independently of one another, denote 0 or 1, $Y^{11}$ to $Y^{14}$ each, independently of one another, denote alkyl having 1 to 4 C atoms, or alternatively, independently from each other, the two pairs ($Y^{11}$ and $Y^{12}$) and ($Y^{13}$ and $Y^{14}$) may be connected by a bond to form together a divalent group having 3 to 6 C-atoms $R^{11}$ denotes O•, $R^{12}$ on each occurrence, independently of one another, denotes H, F, $OR^{14}$, $NR^{14}R^{15}$, a straight-chain or branched alkyl chain having 1-20 C atoms, in which one —$CH_2$— group or a plurality of —$CH_2$— groups may each be replaced by —O— or —C(=O)—, but two adjacent —$CH_2$— groups cannot be replaced by —O—, or denotes a hydrocarbon radical which contains a cycloalkyl or alkylcycloalkyl unit, and in which one —$CH_2$— group or a plurality of —$CH_2$— groups may each be replaced by —O— or —C(=O)—, but two adjacent —$CH_2$— groups cannot be replaced by —O—, and in which one H atom or a plurality of H atoms may each be replaced by $OR^{14}$, $N(R^{14})(R^{15})$ or $R^{16}$, or denotes an aromatic or heteroaromatic hydrocarbon radical, in which one H atom or a plurality of H atoms may each be replaced by $OR^{14}$, $N(R^{14})(R^{15})$ or $R^{16}$, $R^{14}$ on each occurrence, independently of one another, denotes a straight-chain or branched alkyl or acyl group having 1 to 10 C atoms or an aromatic hydrocarbon or carboxyl radical having 6-12 C atoms, $R^{15}$ on each occurrence, independently of one another, denotes a straight-chain or branched alkyl or acyl group having 1 to 10 C atoms or an aromatic hydrocarbon or carboxyl radical having 6-12 C atoms, $R^{16}$ on each occurrence, independently of one another, denotes a straight-chain or branched alkyl group having 1 to 10 C atoms, in which one —$CH_2$— group or a plurality of —$CH_2$— groups may each be replaced by —O— or —C(=O)—, but two adjacent —$CH_2$— groups cannot be replaced by —O—;

and b) one or more compounds of formula II

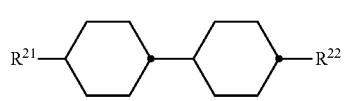

II in which $R^{21}$ denotes an unsubstituted alkyl radical having 1 to 7 C atoms or an unsubstituted alkenyl radical having 2 to 7 C atoms, and $R^{22}$ denotes an unsubstituted alkenyl radical having 2 to 7 C atoms, and optionally c) one or more compounds selected from formulae III-1 to III-4,

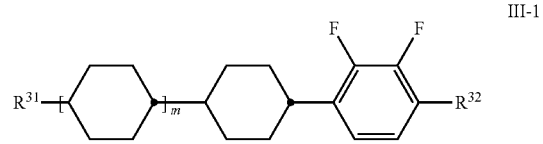

III-1

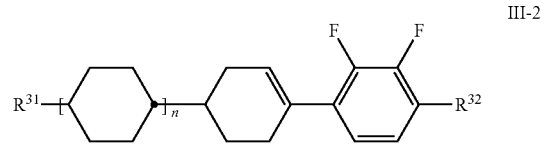

III-2

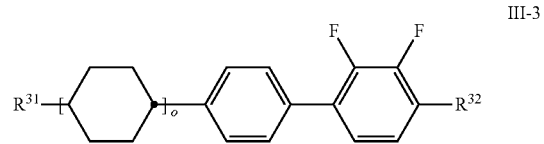

III-3

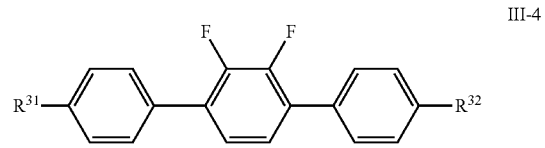

III-4 in which $R^{31}$ denotes an unsubstituted alkyl radical having 1 to 7 C atoms, $R^{32}$ denotes an unsubstituted alkyl radical having 1 to 7 C atoms or an unsubstituted alkoxy radical having 1 to 6 C atoms, and m, n and o each, independently of one another, denote 0 or 1.

2. A liquid-crystalline medium according to claim 1, wherein said compound of formula I is selected from formulae I-1, I-2, I-5, and I-6

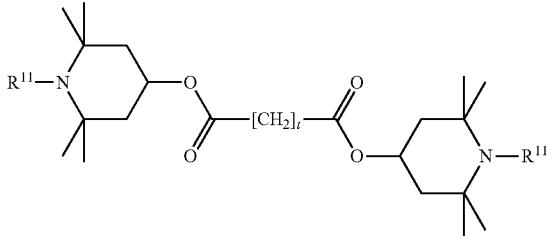

I-1

I-2
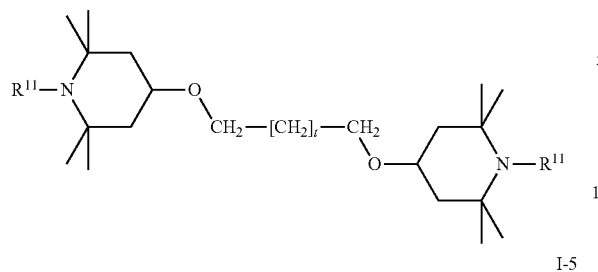
I-6
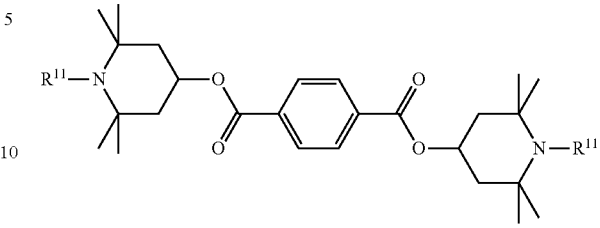
I-5
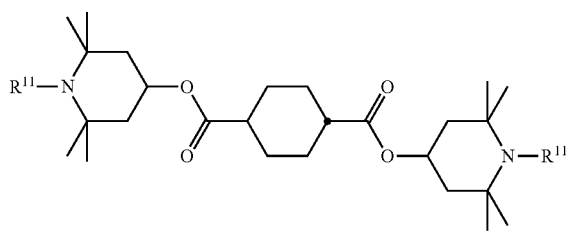
in which $R^{11}$ has the meaning indicated in claim 1, and t denotes an integer from 1 to 12.
3. A liquid-crystalline medium according to claim 1, wherein said compound of formula I is selected from formulae I-1a-1, I-1a-2, I-1a-3, I-1a-4, I-1a-5, I-2a-1, I-2a-2, I-5a-1, and I-6a-1
I-1a-1
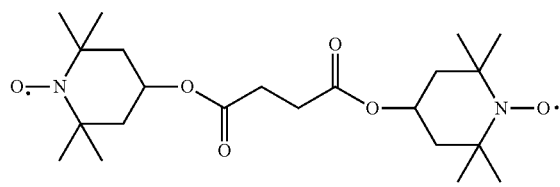
I-1a-2
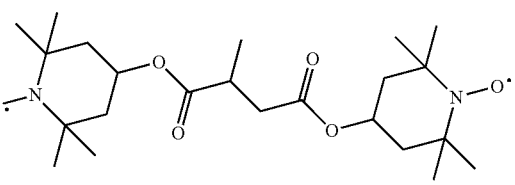
I-1a-3
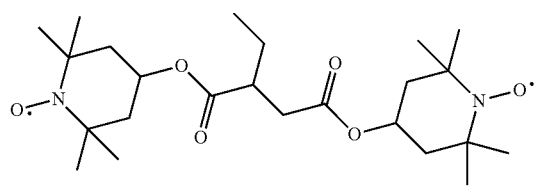
I-1a-4
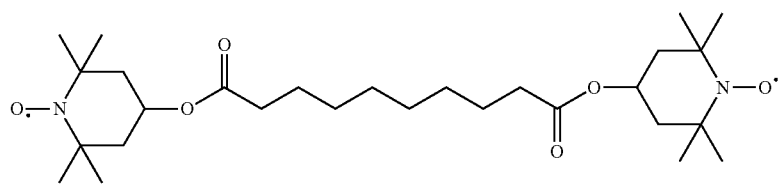
I-1a-5
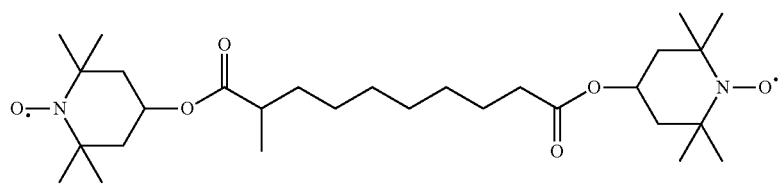
I-2a-1
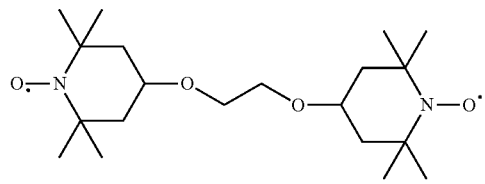
I-2a-2
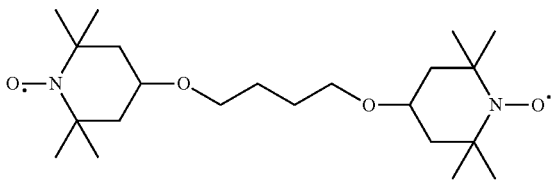

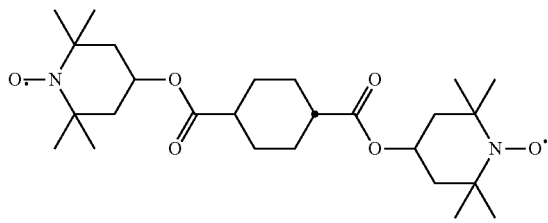 I-5a-1

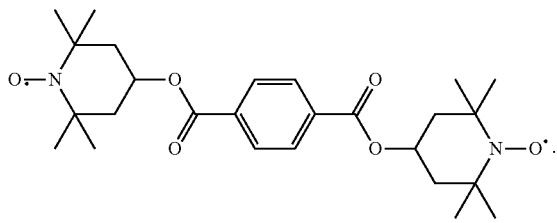 I-6a-1

4. A liquid-crystalline medium according to claim 1, wherein said medium contains one or more compounds selected from formulae III-1 to III-4.

5. The medium according to claim 1, wherein the total concentration of the compounds of formula I in the medium as a whole is 1 ppm or more to 1,000 ppm or less.

6. The medium according to claim 1, wherein said medium comprises a compound of formula II in which $R^{21}$ denotes n-propyl and $R^{22}$ denotes vinyl.

7. The medium according to claim 6, wherein the total concentration of the compounds of the formula II in the medium as a whole is 25% or more to 45% or less.

8. The medium according to claim 1, wherein said medium comprises one or more compounds of formula III-2-2

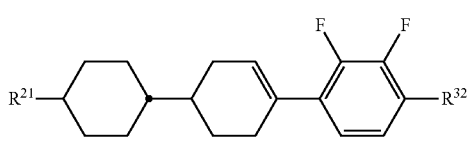 III-2-2

9. The medium according to claim 1, wherein said medium comprises one or more compounds of formula III-4.

10. The medium according to claim 1, wherein said medium additionally comprises one or more chiral compounds.

11. An electro-optical display or electro-optical component, comprising a liquid-crystalline medium according to claim 1.

12. The display according to claim 11, wherein said display is based on the VA or ECB effect.

13. The display according to claim 11, wherein said display comprises an active-matrix addressing device.

14. A method of generating an electro-optical effect comprising applying a voltage to a liquid-crystalline medium according to claim 1.

15. A method according to claim 14, wherein said liquid-crystalline medium is in an electro-optical display or in an electro-optical component.

16. A process for the preparation of a liquid-crystalline medium according to claim 1 comprising mixing one or more compounds of formula I with one or more compounds of formula II, and optionally one or more compounds selected from formulae III-1 to III-4.

17. A liquid-crystalline medium according to claim 1, wherein said medium further comprises one or more compounds selected from formulae OH-1 to OH-6

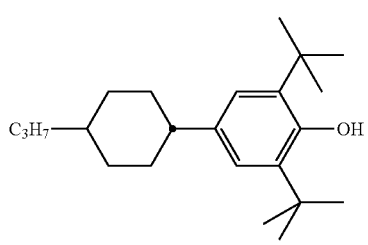 OH-1

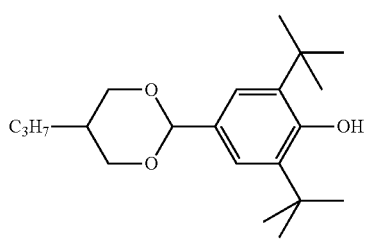 OH-2

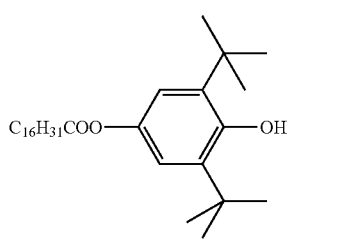 OH-3

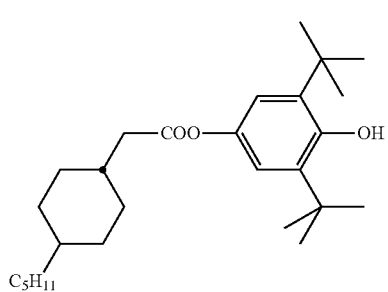 OH-4

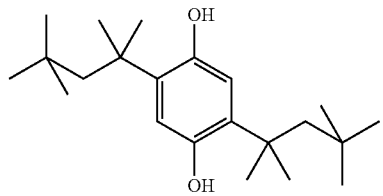 OH-5

OH-6

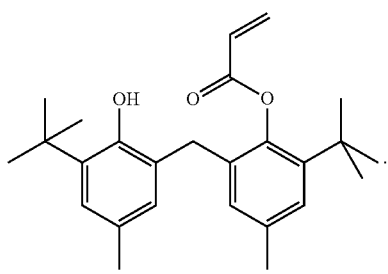

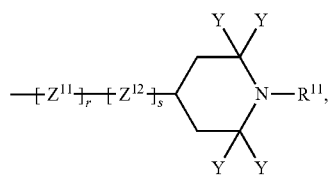

denotes

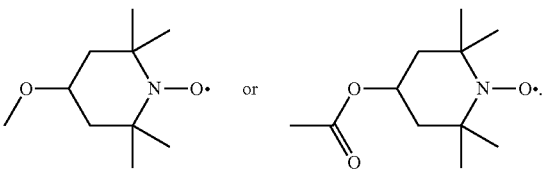

18. A liquid-crystalline medium according to claim 2, wherein said compound of formula I is selected from formulae I-1.

19. A liquid-crystalline medium according to claim 3, wherein said compound of formula I is selected from formulae I-1a-1.

20. A liquid-crystalline medium according to claim 3, wherein said compound of formula I is selected from formulae I-1a-1, I-1a-2, I-1a-3, I-1a-4, and I-1a-5.

21. A liquid-crystalline medium according to claim 1, wherein ZG denotes —(CH2-)$_2$, —(CH2-)$_4$, —(CH2-)$_6$, —(CH2-)$_8$, propane-1,2-diyl, butane-1,2-diyl, ethane-1,2-diyl,

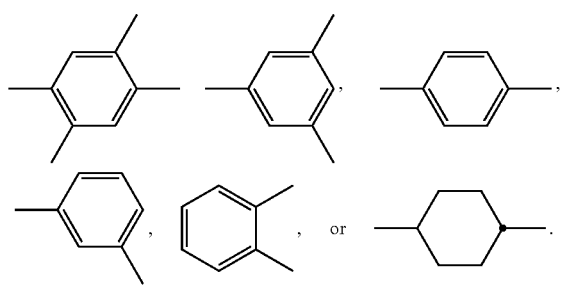

22. A liquid-crystalline medium according to claim 1, wherein the group

23. A liquid-crystalline medium according to claim 21, wherein the group

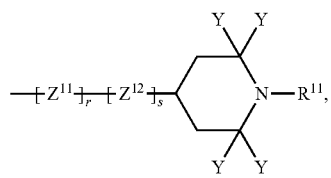

denotes

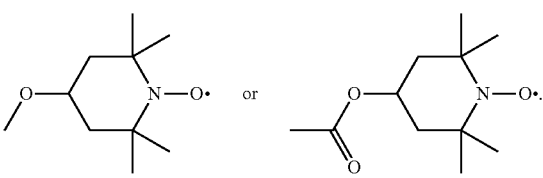

24. A liquid-crystalline medium according to claim 2, wherein said compound of formula I is selected from the following compounds 1-7:

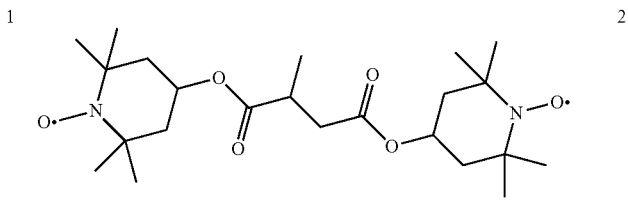

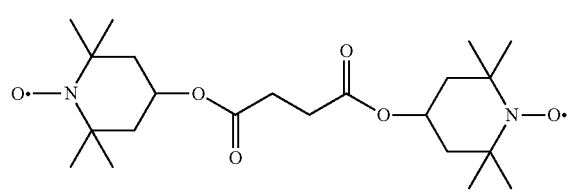

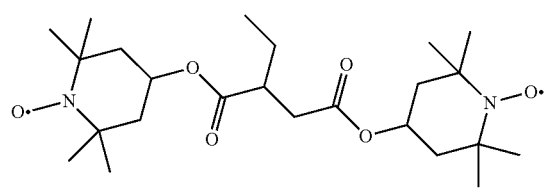

-continued
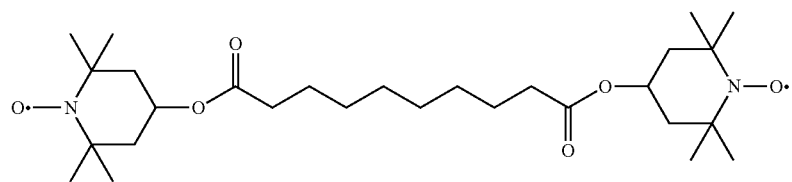
4
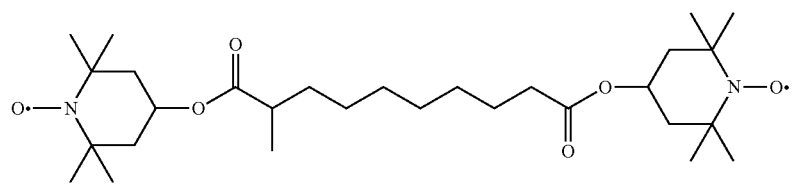
5
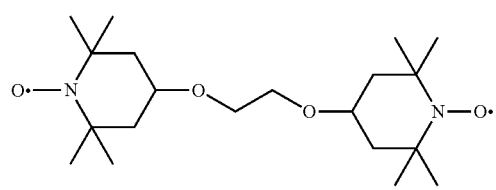
6
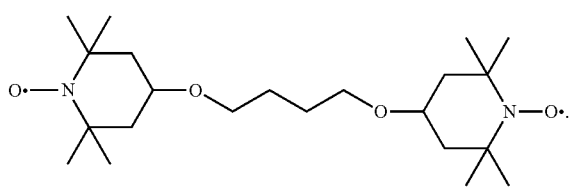
7
* * * * *

UNITED STATES PATENT AND TRADEMARK OFFICE
CERTIFICATE OF CORRECTION

PATENT NO. : 8,999,460 B2
APPLICATION NO. : 13/451749
DATED : April 7, 2015
INVENTOR(S) : Mark Goebel et al.

It is certified that error appears in the above-identified patent and that said Letters Patent is hereby corrected as shown below:

IN THE CLAIMS:

Column 99, lines 29-38 (Claim 8), the compound of formula III-2-2 presents as:

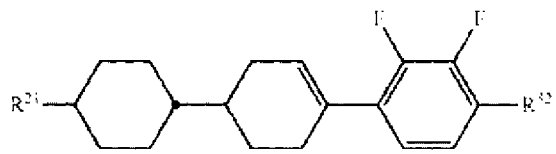

Should present as:

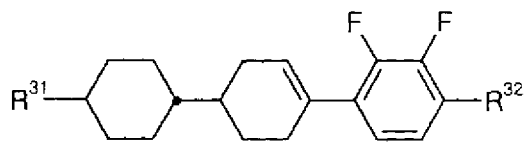

Signed and Sealed this
Eighteenth Day of August, 2015

Michelle K. Lee
*Director of the United States Patent and Trademark Office*